(12) United States Patent
Bovet

(10) Patent No.: US 9,528,118 B2
(45) Date of Patent: Dec. 27, 2016

(54) HEAVY METAL REDUCTION IN PLANTA

(75) Inventor: Lucien Bovet, La-chaux-de-Fonds (CH)

(73) Assignee: Philip Morris Products S.A., Neuchatel (CH)

( * ) Notice: Subject to any disclaimer, the term of this patent is extended or adjusted under 35 U.S.C. 154(b) by 72 days.

(21) Appl. No.: 13/819,063

(22) PCT Filed: Aug. 31, 2011

(86) PCT No.: PCT/EP2011/004383
§ 371 (c)(1),
(2), (4) Date: May 2, 2013

(87) PCT Pub. No.: WO2012/028309
PCT Pub. Date: Mar. 8, 2012

(65) Prior Publication Data
US 2015/0232867 A1 Aug. 20, 2015

(30) Foreign Application Priority Data
Sep. 3, 2010 (EP) .................................... 10009180

(51) Int. Cl.
C12N 15/82 (2006.01)
C12Q 1/68 (2006.01)
C07K 14/415 (2006.01)
C07K 16/16 (2006.01)
C12N 15/113 (2010.01)

(52) U.S. Cl.
CPC ......... *C12N 15/8218* (2013.01); *C07K 14/415* (2013.01); *C07K 16/16* (2013.01); *C12N 15/1138* (2013.01); *C12N 15/8242* (2013.01); *C12N 15/8271* (2013.01); *C12Q 1/6895* (2013.01); *C12Q 2600/158* (2013.01)

(58) Field of Classification Search
None
See application file for complete search history.

(56) References Cited

U.S. PATENT DOCUMENTS 6,166,290 A * 12/2000 Rea ...................... C07K 14/395
435/252.3
6,677,502 B1 1/2004 Allen

FOREIGN PATENT DOCUMENTS

WO 03/033705 4/2003
WO 2009/074325 6/2009
WO WO 2009/074325 A1 * 6/2009

OTHER PUBLICATIONS

Zientara et al., 2009, Journal of Biotechnology 139: 258-263.*
Rea, 1999, Journal of Experimental Botany 50: 895-913.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Vogel and Marcotte, 2012, Nature Reviews 13: 227-232.*
European Examination Report dated Jan. 8, 2014 for European Application No. 11752485.0-1406 (4 pages).
Chinese Examination Report for Application No. 201180052798.9 dated May 6, 2014 (5 pages).
PCT/EP2011/004383 International Preliminary Report on Patentability dated Mar. 5, 2013.
Chinese Second Examination Report for Application No. 2014111901332480 dated Nov. 24, 2014 (8 pages). English translation included.
European Examination Report for Application No. 11752485.0-1406 dated Dec. 8, 2014 (5 pages).
Database EMBL [Online], Oct. 27, 2009, XP002665516, Database Accession No. FH224591 (1 pg.).
Wojas, et al., "Ectopic Expression of Arabidopsis ABC Transporter MRP7 Modifies Cadmium Root-to-Shoot Transport and Accumulation", *Environmental Pollution*, vol. 157, No. 10, Oct. 1, 2009, pp. 2781-2789.
Klein et al., "Disruption of AtMRP4, a Guard Cell Plasma Membrane ABCC-Type ABC Transporter, Leads to Deregulation of Stomatal Opening and Increased Drought Susceptibility", *Plant Journal*, Jan. 1, 2004, pp. 219-236.
Sanchez-Fernandez, "Cloning and Expression Analyses of AtMRP4, a Novel MRP-Like Gene from Arabidopsis Thaliana", *Molecular and General Genetics*, Mar. 1, 1998, vol. 258, pp. 655-662.
Bovet al al., "Transcript Levels of AtMRPs After Cadmium Treatment: Induction of AtMRP3", *Plant, Cell and Environment*, Jan. 1, 2003, pp. 371-381.
Bovet et al., "Cadmium Accmulation Capacities of Arabis Alpina Under Environmental Conditions", *Environmental and Experimental Botany*, vol. 57, No. 1-2, Aug. 1, 2006, pp. 80-88.

(Continued)

*Primary Examiner* — David T Fox
*Assistant Examiner* — Bratislav Stankovic
(74) *Attorney, Agent, or Firm* — Mueting, Raasch & Gebhardt, P.A.

(57) ABSTRACT

There is described a mutant, non-naturally occurring or transgenic plant or plant cell comprising (a) a polynucleotide selected from the group consisting of: (i) a polynucleotide comprising, consisting or consisting essentially of a sequence having at least 71% sequence identity to SEQ ID NOs: 1, 2, 27, 28 or 29 or 51; or (ii) a polynucleotide comprising, consisting or consisting essentially of a sequence having at least 65% sequence identity to any of SEQ ID NOs: 3 to 23 or 30 to 50; or (iii) a polynucleotide encoding a NtMRP polypeptide comprising, consisting or consisting essentially of a sequence having at least 65% sequence identity to any of SEQ ID NOs. 24 to 26 or 52, and wherein the polypeptide has heavy metal transporter activity; or (b) a polynucleotide construct of at least 15 contiguous nucleotides in length that is at least 65% identical to a region of any of SEQ ID NOs: 1 to 23 or 27 to 51; or (c) a double-stranded RNA comprising at least two sequences that are at least partially complementary to each other and wherein a sense strand comprises a first sequence and an antisense strand comprises a second sequence and wherein at least one of the sequences comprises at least 10 contiguous nucleotides of NtMRP RNA; or (d) an expression vector comprising the polynucleotide as set forth in (i), (ii) or (iii) or the polynucleotide construct as set forth in (b).

8 Claims, 13 Drawing Sheets

(56) References Cited

OTHER PUBLICATIONS

Mizuno et al., "Isolation of Multidrug Resistance Associated Protein Like Gene from Lead Hyperaccumulator Common Buckwheat and its Lead Detoxification Ability", *Plant Biotechnology*, vol. 27, No. 1, Jan. 1, 2010, pp. 39-46.
Database EMBL [Online], Oct. 22, 2009, XP002672792, Database Accession No. ET786183.
Zientara et al., "Activity of the AtMRP3 Promoter in Transgenic Arabidopsis Thaliana and Nicotiana Tabacum Plants is Increased by Cadmium, Nickel, Arsenic, Cobalt and Lead but not by Zinc and Iron", *Journal of Biotechnology*, vol. 139, No. 3, Feb. 5, 2009, pp. 258-263.
Wang et al., "An ATP-Binding Cassette Transporter Related to Yeast Vacuolar ScYCF1 is Important for Cd Sequestration in Chlamydomonas Reinhardtii", *Plant Cell and Environment*, vol. 29, No. 10, Oct. 2006, pp. 1901-1912.
Chinese Office Action for Application No. 201180052798.9 dated Jul. 1, 2015 (6 pages). English translation included.
Chinese Office Action for Application No. 201180052798.9 dated Aug. 19, 2016 (13 pages). English translation included.
Canadian Office Action for Application No. 2,809,573 ated Aug. 19, 2016.
Indonesian Office Action for Application No. W-00201301402 dated Aug. 15, 2016 (6 pages). English translation included.

\* cited by examiner (b)  tcctagtactgtaagtgaaccagcaaggaaactgcaaagtagatttcttgttcatcaaat
aaatccttgagctgagagatatgattttttctaaggaatttctctttggctctctgtagt
ggtgagtttgattcatatttcaatctagttttttagctttgcttaaaagcttcttcttgcc
actagaccaaatccttttccttttttgcatgacactttttttgagtttcatttctcttattt
atagagaaaatcttttgatggggatggtttttttttctcttttgcattaatgattagaatt
tatcattgttaaatggtactccctcaataactttttgatttaaaaaaaaaactgtcctttt
cattcataatcatcatctcctttattatattactctaaactgttgctaaagttcctttttt
gtatatttccctacatgaacttttgctgtactgtgaaagttgatgaacttttattgtac
aatgttttggtccagtagctaacagccccttttatttaattctgagaggtctctttctctt
tctcttcacactttcacatgtttccgtttcctgtagatttctcctttctctttccttggt
tcttttttccaactcataatcttcatgtgatttcaattttttgtttgtttttattccatcct
ttgtctcttttgatatgggtgacaaacatcttctcttgctgaataaaaatttcacctttt
ttcagtgtatgcagattcagggggatataaagacataaaggatgaatcttttatggtataa
cATGGATATGAGGAACAGTATGTCTTCAGAATCTTGTTTAGCATCACTTTCTTGTTCTGC

FIG. 1

(b) CTCCACATTTCAATCGTCAGAGGATTCAGCAGTTGTTAAATGGTTAAGATTCATTTTCCT
CTCTCCATGTCCACAAAGGACTCTTCTATCTTCCATTGATGTGCTGCTTTTGCTTACTTT
CATTGTATTTGCAGTACAAAAGTTGTACTCAAAGTTGAGGTCCAATGAGCACTCTACTTC
TAGCATTGATAAGCCTCTAATTGCACACAACAGGACTTCTgttagaaccaatctttggtt
taagctgtctctgattttgtcagctattttagccttatcttctatagttttatgcatttt
ggttattgtgggaaattcccagTCGCCTTGGAAAGTCATAGATGGACTGTATTGGTTGTT
TCAGGCGATTACACATGTTGTAATCACTATACTAATAGTTCATGAGAAAAGATTTCACGC
TATTTCCCATCCACTGTCCCTGCGCGTGTTTTGGATTGCAAACTTTGTAGTTATGAGTTT
GTTCTTTGGTTGTGGGATCACAAGGCTTGTGTCACTTAAGGAAATTGATCCTAATTTAAG
AATGGATGATATAAGTTCATTAGTTTCATTTCCTATTTCTGTTGTTCTCTTCATTGTTGC
CATTAAAGGTTCGACCGGAGTTGCTGTAATTAGTGATTCTGAATCTCACTTAAGTGATGA
AACCAATGGTTATGAACTCCTGGATAAATCCAGTGTGAGTGGCTTTGCTTCAGCTTCTCT
AATATCGAAAGCCTTTTGGATTTGGATGAACCCTTTACTGCAAAAAGGTTACAAGTCACC
TCTCAAGATTGATGAAGTTCCTTCACTTTCCCCACTGCATAGAGCAGAGAAAATGTCTCA
ACTTTTCGAAAGAAATTGGCCTAAACCTGAAGAAATATCAAAGCATCCTGTCCGAACAAC
ATTGCTGCGTTGCTTTTGGAAGGAAGTTATTTTTACTGCCATTCTTGCAGTAATTAGGGT
ATGTGTTATGTATGTAGGGCCAACACTCATACAAAGATTTGTTGATTACACAGCAGGAAA
GAGGACATCTCCTTATGAAGGATACTACCTTATAGGAACTCTCCTAATAGCCAAATTTGT
GGAAGTTCTAACCTCTCATCAGTTCAACTTTAACTCCCAAAAGCTTGGCATGCTTATTCG
AGCGACACTTCTCACTTCTTTGTATAAGAAGGGGTTAAGGTTGTCATGCTCAGCTAGACA
GGCTCATGGTGTTGGACAGATTGTAAATTATATGGCCGTCGATGCTCAGCAGCTGTCCGA
TATGATGCTACAGCTACATTCCATTTGGCTCATGCCATTGCAAGTTTCTGTGGCTTTAGG
CATCCTTTATACTTACCTCGGTGCTTCAACTGTTGTAACGCTAGCTGGACTTGCAGCAGT
GATGGTATTTGTGGTGTTTGGAACTAAAAGAAACAACAGGTTTCAATTTAACATCATGAA
GAATCGTGATTCTAGAATGAAAGCGACAAATGAGATGCTTAATTATATGCGCGTTATAAA
GTTCCAGGCATGGGAAGAACATTTTAACAAAAGAATTGAATCCTTCCGCGAATCCGAGTA
TGGATGGTTGTCCAAGTTCTTGTACTCAATCGCTGGGAATATCATTGTCTTGTGGAGCAC
TCCTCTTCTAGTGGCTACACTCACTTTTGGAAGTGCAATCTTGTTGGGAATCCCGCTTGG
TGCAGGGACAGTGTTCACTGCAACATCTCTCTTCAAGATGTTGCAGGAACCGATCAGGGC
TTTCCCTCAATCCATGATCTCACTTTCACAAGCAATGATATCTCTTGATAGATTGGACAA
ATATATGATGAGTAAGGAGTTAGTGGATAAAGCTGTGGAAAGACTAGAAGGTTGTGGGGG
TACAATTGCTATGCAGGTGAAAGATGGAGCTTTTTGCTGGGATGATGAAAACAGTAAAGA
AGAATTGAAAAATGTAAACTTTGAGATTAGAAAAGGAGAGCTTGCAGCAGTAGTGGGGAC
AGTTGGGGCGGGGAAGTCTTCCCTCCTTGCATCTGTACTTGGTGAGATGCACAAGTTGTC
GGGTCAGgtatggctctcatccttctgtttgtttgattaatacaaactttgctgccaatt
acctttgccccttgttgctacctcttttctgtggtataaaaattaatgtaggctaatg
tgtagagtggaggtattatatgcagaacaattgcaatcaagcaattacctgtgagatact

FIG. 1(Cont'd)

(b) attttgttttcatattagtggactggtacattctcattggtgtatcgtttgatctccacc
aaagcagaggttttactggccgacagagtcaaactactgtgcttcactccttttactcca
atccttagtagtctttgcttctaatgaacttcaagcgtgtaatagaaacaccattatatt
attagctgattagttactttacaattccagagcatatttacattttctgcttggttgtct
attactctggataacagtcctaaatgcaagcaaaatcaactgtgttttcagtcttgagct
gaccaattagttcatgatgtcctcagcttgtccaagctggtgcctcaccggaattatgtg
ggaccttcgtacttaatcaactagttcaccttcttcttaaaaatattgaatgatttgatt
ggttaatagttccttaaatgtagtaattatttgctaacttactttaccaacccttgtcc
aacagGTCACAATTTGTGGTTCAACTGCCTATGTTGCACAAACATCGTGGATTCAGAATG
GCACGATACAAGAAAATATCCTGTTTGGTATGCCAATGAACAGAGACAGATACAAGGAAG
TGATCCGGGTTTGCTGCTTGGAGAAGGACTTGGAAATAATGGAGTTTGGAGACCAGACTG
AAATAGGAGAACGTGGCATCAACCTCAGTGGTGGTCAGAAGCAGCGAATCCAGCTTGCAA
GAGCTGTTTACCAGGACTGTGATATTTATCTTCTAGATGATGTATTCAGTGCAGTTGATG
CTCACACTGGCTCTGAAATCTTCAAGgttagaagtccacaatgtcatgtgtcattgaaga
tttaatttaagatagaaattacattgtttcattctgcaaattatggacctatcagagaaa
atcatggattttgaatggctactttccccagtgaagacacatatcatttcctgggagga
agatgtgaaagtggcaagctatttactccaaaaagtataatctaaaagactttttattaag
tttggaaggcttaatccatcatttgttatctgttgtctacttgtctttattaaaattctt
cttagtccaatcactttcgatgaagttgactagtcttagtcacctgaatactttaaatct
ttgccttggtgtctctatattttcagccatctcaattccgaagctcatatttgttttctc
tttgtaatgtccatctgaaagtttcatgcttttttgcagGAATGTGTGAGGGGAATTCTT
AAAGATAAAACCATTTTGCTTGTCACACACCAAGTTGACTTCTTGCATAATGTTGACCTG
ATCCTTgtaagtttcagagtgttttatcaaccccctttggaaccaagtgtcaagagtagtg
tttcttggttgttaaatgattcacatgtgtgttggtttctataaaacctgaactttatgt
tttatcagagtgttttgctttcttgaagGTCATGCGAGATGGGATGATCGTGCAATCTGG
CAAATATAATGAGATATTAGAAGCTGGAATGGATTTTAAAGAGCTAGTAGCTGCACATGA
GACCTCTTTAGAACTTGTTGACGTGGAAACAACCAAAGAGAGCAATGCCTCCCTTGAAGA
ATCAAAATCTTCTCGAAGATTATCTAAGGAAGAAAACGGAGATGATAAATCTCAACAGTC
TACATCTGATAGGGGGGATTCTAAACTTATAAAGGAAGAAGAAAGAGAAACTGGAAAAGT
CAGTCCTCGTGTGTACAAGCTATATATTACTGAAGCTTTTGGATGGTGGGGTGTAGTGCT
AGTTATCTTGTTTTCGTTCTTGTGGCAAAGTTCTCTAATGGCAAGTGATTATTGGCTGGC
ATATGAAACTTCAGCGGATCGTGCCATGTCCTTCAATCCTTCTCTGTTTATTGGGATATA
CGGTGTTATTGCAGTTGTTTCTTCGTTGCTGATAGTGATCAGGATGTATTTTGTGACACT
TATGGGGCTCAAGACTGCCCAAATATTTTTCGGACAGATTCTTTACAGCATACTGCATGC
TCCTATGTCATTTTTTGACACAACACCTTCCGGAAGAATTCTGAGTCGGgtaaatttctg
aggacaagttttccttttgcatgtaaattcaaactttgctgcttagatgattaaataat
gaaaaatatccattgcatgttttaatgtgtatgacatgttagaattttgaatagaagttc

FIG. 1(Cont'd)

(b) attcactgatgttgagatgttttgttttttttctgcag**GCATCTAATGATCAGACCAACA
TTGATGTCTTCCTCCCGTTTTTTATGAATCTCACTTTGGCCATGTTTATCACACTGCTCG
GCATCATCATCATCACATGCCAATATTCTTGGCCTACCGTACTACTTTTGATTCCTCTGG
GTTGGCTTAATATCTGGTACCGG**gtatgagcactgtttataacagccgtccttttttctt
ttcttgtctgaactcaaatttgaatcctttgtttagaggcaattagtctgctctgagcat
tttggctgacagttattatgtatattaaaaggcaacttttttattcgttctgtccagcta
aaacttttttacttaaaatgtggttaactgcatatttctgtgtctcctattttttgattat
ttgcaactctgatcaatctagatttggggaaggcttgttgttagttgatgactagatact
aagctcacatctacattggttgcaagtagaattttcaagttgtcattcacttatattgtt
tgaactaggagattagcattcttctgcaaggagccctgaatgcttgaaaagttaaacaga
aagaaaaagttcagggcagatagacataatgtgttaaagtaattcaattggagcacaga
tatatgacatgtgttatttgggagctacgaaaaagataaggactattatgtagactacaa
ttgaaataacaggtaattcatttctggtttacag**GGATATTATCTTGCAACATCTCGTGA
ATTGACTCGGCTTGACTCAATTACAAAAGCACCTGTTATTCATCATTTCTCTGAAAGCAT
CTCAGGTGTTATGACTATACGTTGCTTTAGGAAGCAGGAGATGTTTTGTAACGAGAATGT
AAACCGAGTGAATTCCAATCTGCGAATGGATTTCCACAACAATGGATCCAATGAATGGTT
GGGCTTTCGACTGGAATTGATGGGAAGCTTACTTCTTTGTGTTTCTGCAATGTTCATGAT
TGTCTTACCTAGCAGCATCATCAAGCCAG**gtataacaccgtccaatgctcatttatggga
attataaattctagtatttgataatccttctgtactttagatctacctgctctactgaaa
aatgaaatgagtatgaggaaatagaatatccgttgagcatttatgtctttctattaaaaa
tttgcattctatcttcttgtttcaagtcaaaatcttgaacaactatatctagagaattttt
ccttcttgtgaagtaatgcatatatacatcaagagaagtcagagttgctgaatgaaatag
tagatcaaatttaagtgttgtgcctataaagaattgtatggtgagattgaatatagtggt
catattatttttctcaatcttagtgattaaagtattccatacaaacagacaagcatttagt
cgtgcattcattggcactacaaaattatcaaccaagagtaatattctttcagcttttcctc
tgtatatgtgtgttctattctggagctgaagataactaatattcttttttatttctacag**AAAATGTTGGTTTGTCACTATCATATGGCTTGTCTCTTAATAGTGTCCTATTCTGGTCCA
TCTTTGTGAGTTGCTTTGTGGAAAATAAAATGGTTTCTGTCGAAAGATTAAAACAGTTCT
CAGAAATACCATCAGAAGCAGAGTGGAGAAAGATGGATTTTCTCCCACCTTCAAGTTGGC
CAAGCCGTGGGAATGTTGAGCTTGAAAACGTGCAG**gtaataattctaactaattctgtgg
ttgctatttgctagcatttgcacaaaaggaaaactataaaaagttcatagtaaggaagag
agggtagctgtattaacaagcctacagattctttaatttcaaatatgttacgttgaatct
ctatattgtttgttctactggtcaacag**GTTAGATATCGTCCGAACACTCCTCTAGTGCT
TAAAGGAGTTACTCTCAGCATTAGAGGGGGAGAGAAGATAGGTGTTGTTGGTCGTACAGG
GGGTGGAAAATCAACATTAATTCAAGTTTTCTTTCGTTTGGTGGAGCCTGCAGCTGGAAG
AATAATCATTGATGACGTAGATATATCCAGACTTGGGCTTCATGATCTTAGATCTCGCTT
CGGGATCATTCCCC*AAGAGCCAGTCCTTTTTGAAG*GAACTGTGAGAAGCAACATTGACCC**

FIG. 1(Cont'd)

(b) CATTGGACAATATTCAGATGATGAAATTTGGAAGgtaatctaacttgctgactgaaataa
tttacaaaaatctcaaaatatagtacagagttagccaaacatgtcttctgagtgctgaga
tcttttttggattataaattctgtaagagcaacatactatttgttagtgagaagaaaagca
tatactccagtgttttgttatctcccagaatgtctctaacatgaaatcgtgtacattgca
g**AGCCTCGAACGCTGCCAACTCAAAGATGTGGTGTCTTTAAAACCCGAAAAACTTGATTC
ACCAG**gtaaattttcctcctctacgtcatccttgtggttctttgcggaattatgcaacca
acttttatgtgtttcaaatatatactgataactgaatactgtcattggtaaatcata
g**TTGTTGATAACGGAGATAACTGGAGTGTCGGACAGAGGCAGCTTCTTTGCTTGGGAAGA
GTGATGCTAAAACGTAGCAGACTTCTATTTATGGATGAGGCAACTGCCTCTGTTGATTCA
CAGACAGATGCAGTGATTCAGAAAATCATCCGCGAGGACTTTGCGGCCTGTACTATAATC
AGCATTGCCCACAGAATACCAACAGTCATGGACTGTGATAGAGTTCTTGTTATAGATGCA
GGTGCTGATTTCTCTCCTTTTACTTTGTACCTTATTTTGAATCTGGTAAATGATTATTTA
TCTGTATGTGATGGTTTCCAACCAATCATAGTCAGTACCTTTATGAAGAAATTGCCTAAT
GTTAGCCAAGTAGTAGTAAATGCATGAagtcattagcctatttgttttggattttgtgag
tttcatacttcaaactggaagcttatgctatactatctgatcccttgtttgtatagattg
ctttcttttccttttctcggatttatcttatatataagcggacagagtaaaagaatgta
aacatgcgtaatttgacctattatagcagattatttgtcttattttccaggtcgctgatt
ccacttattaggagtagttacacgtatttatcttttaagtgaaataatagtgtaaagttt
cttttggcactgtcggtgtaaagaagttaaactcctttctttaaccccggcatttcttat
tcatgcaggaatagcaaaagagtttgacaaaccatctcgtttgcttgaaaggccttcact
ttttggggctttg~~gttcaagaatatgccaaccgat~~cctctgagctctaaccacactattt
tggctttcatgccttttgctgtaaattgcagctatcttggaggataggtgaaacaggaaa
aatacctatccaaatgttacatagatttccaaatagtgttatctcctactaagctatcca
gtagattttggaaatgtaacaatattgggattaacaattgtaattgatgaatctattaa
tcaaatacaatgattattctgttatagatgtagtctgtgcaatgttatatagactgattt c ccgtcaaccagtcttggccaccacacataaacacagctttgacttgtctctccctatttcaccacccttttca
atttcccacccttatattcattatattaatcaatcaaatcaaagttgaaaaaaaggagtaataatcaaatggagt
agtatatacataccagaacaatgaaagagcactcataagctaaagcccataattcatcacgaaccacaatatagaggaa
acctgacgtgtccctaaaatctaaccttgaacctctgagacctccaaaaaaacatc<u>ATGGAAATTCAAAGGCATGT</u>
<u>CTGTGTTCAATCTTTGAG</u>gtatgttggcgttgatgaatccctccgaaaccccattttcttacgtgtcattagttgttct
ttgcacctgggattgttccttgtaattcttgggttgtgtttggaatacaatcag<u>GAGGGACAATAATGCTGGCCACAA</u>
<u>CTTGTTTGTTGTACTACTACTGGAATGCTAGCTTCTTGTTGTTAGCTTGGTCAGACCCTGTTGTTCAGAATCAACCTTGTTTGCAATCGTAGCCATCTTTAGCT</u>
<u>TTGTGTGCTTAAGAGTTGTGTGTTAGCCTTGGTCGTGGGGGCTTCTTTCAATCTGTTTCTTTGTTATAGAAATGGTTGGTCACACCCAGTTCCTTGTTGTAATCTATAACCTTTGCATTT</u>
<u>GCATTAAGTTGCTAGCCTTGGTCGTGGGGCTTCTTTCAATCTGTTTCTTTGTTATAGACCTTGTTATGCCTTGTATGGCATGCTTGCCATTGCCATGCATCTTG</u>
<u>ICTGTGTTTAAGAGTCTTACCAACTGAATTCAATTTGTATACCTTATCCTCACTCTGATGTGTTAATACCCTCTTAAATGCTAACCTGATTTTAGTCTCTTCACTTGCCATGTCTAGAT</u>
<u>AGAACCAAATCTTACCCAACTGAATTCAATTTGTATACCTTATCCTCACTCTGATGTGTTAATACCCTCTTAAATGCTAACCTGATTTTAGTCTCTTCACTTGCCATGCTTATTCTGATGG</u>
<u>TTTATTGTTAAACAGAATGTAGGGCAACAAACTGTCACCCTTAAATGCTAACCATTAGACCCATTAGACCTTGAGGATGTGTGCGGGAATAGTGTCGCTACGTTGACTTGATAGTGCAA</u>
<u>AAAGAAGTCTACTGGGATCAAACTGTCACCCTTAAATGCTAACCATTAGACCCATTAGACCTTGAGGATGTCTGCCAATGCTAACTTACTGTCGCTACTTGATAGTGTCAA</u>
<u>GTCCCCTATAATTTCTGTTGGCAACAGAATGTAGGAACAGAAGCATTAGACCCCTGGGTTATGCCTCTCTGCCTCTTCGTGCCTCTTCGTGCTGCTCTTTTTG</u>
<u>GCCGAGTTCTTATTTTCACAGACAAGTTGGTGGAGTGTTGGCGAAAGGCATTGGTTTTCAGGTCAGCAACGAAACAACGAACGTGAAGGTTATGTCTTAGTC</u>
<u>GAAGGCCTTCGTTCCTAGCCTTCATTGCATCAGTTACCTTAGTTGGCGAAAGGCATTGGTTTGCGTGTGTAGTTGGCGAAAGGTTATGTCTTAGTC</u>
<u>GCTGCACCGGCAGCTTCGTTGCAATGCCTTCAATATTGGCGAAATCTACAACGCCTTTACCCTGCCTGTCAGTCAGTCAATCAAAGCAAGCCACTAGTC</u>

```
ggttaatttgttggtatgggttggtatatctgaaaacttttaatagGTCCGATATCCTCCTCACATCCCTCCTCGTGTTGC
GAGCCCTACAGCACTTCTTTCCGTGGAAATAGAGACTGGAATTGTCGGTAGGACAGCCAGCCGGTAATCTACTAATA
CAGACCCCTCTTCCGATAGTTGAAGCCAGCCTCCTGACANATANATAGATCGTATCACCATCCTCTCCTCATTGGTTTGCA
TGATCTACGGTCTAGATTGAGTATAATTGCACAGATATAAGTCCAACTATGTTGAGGAACAGTTCGCAGCAACTAGACCGTC
TTGAAGAGTATTCACAGACAGACATATATTCCCAGgtgacagcttggttttgcctattttttgattttattttgtttcagatag
gaaaatgacaaatttattgagaaactttgttgatgttatgcttcagGCCCTCGATAAGTGTCAGCTAGGAGAA
GAAGTGAGGAAGAAAGAAGGCAAACTTTATTCTACAGgtaacttcaagaaccacatcattttctgatgattccactttt
agagctgtaataatcatcttcattgcgttgctgcagTATCTGAGAATGGAGAGAACTGGAGTGTACCCAAAGGCAGCTG
GTCTGCCTTGGCCGTGTGCTACTGAAAAGAGGCAAGTCCTCGTCTCTCGATTCCAGGTTATAACCATTGCTCCACACTGCCAC
TGATAATCTTATTCAGCAAAACTCTAAGGCTCGACTCTACTATTAGATCATGgtaagaatcatcgtttatgttctggagcaagcggagaaaat
tcttggtagttaccttttttttatgctatgctgcagGCCTCATTCCTCGAATACCGTCCACCAGGTTGTTAGAGAC
GAATCCTCATTGTTGCTAACTCGTCTAAGTCCACTGCCAGTATAGTTGAGTCCAATTCAGTTTTCAGAATCTTCAGACATGTG
Agtctcagaaactaatcttcgttaataatgttacacgacgatgatgaaaattagggactctagactagtaccttag
tcgatagtgttttgagtttccatctgtggacatcctgttgacaagagaccagcgaaatgcgaggtcatgcctggctt
gagggaaactgcaacaatcctatgcaggaaagaaaacctacactcagtgatgcaatattgattgtgaagtggcatttgt
ttttgttagactttttgatgagaaaatgtatacgtaactttgtgtttaacataatttgaatgtatgttgagtcaagtga
ttagttagttaagagtgcacgatttgctactcctgggtaaaagaagtaaaccttgttgttgagagttgaaagtgaaat
tactagtgtcgaattttgccgcataagctaaatgaaacactttttacgataaactcctagtgcaacaaagggaaaattcat
tggcaagactagctgttttcacgac
```

FIG. 6(Cont'd)

SEQUENCE LISTING

<160> NUMBER OF SEQ ID NOS: 148

<210> SEQ ID NO 1
<211> LENGTH: 9001
<212> TYPE: DNA
<213> ORGANISM: Nicotiana tabacum

<400> SEQUENCE: 1

```
tcctagtact gtaagtgaac cagcaaggaa actgcaaagt agatttcttg ttcatcaaat        60
aaatccttga gctgagagat atgatttttt ctaaggaatt tctctttggc tctctgtagt       120
ggtgagtttg attcatattt caatctagtt tttagctttg cttaaaagct tcttcttgcc       180
actagaccaa atccttttcc tttttgcatg acacttttt gagtttcatt tctcttattt        240
atagagaaaa tcttttgatg gggatggttt ttttctctt ttgcattaat gattagaatt        300
tatcattgtt aaatggtact ccctcaataa cttttgatt taaaaaaaaa actgtccttt        360
cattcataat catcatctcc tttattatat tactctaaac tgttgctaaa gttccttttt       420
gtatattttc cctacatgaa cttttgctgt actgtgaaag ttgatgaact tttattgtac       480
aatgttttgg tccagtagct aacagccctt ttatttaatt ctgagaggtc tctttctctt       540
tctcttcaca ctttcacatg tttccgtttc ctgtagattt ctcctttctc tttccttggt       600 tcttttttcca actcataatc ttcatgtgat ttcaattttt gtttgttttt attccatcct      660
ttgtctcttt tgatatgggt gacaaacatc ttctcttgct gaataaaaat ttcaccttt        720 ttcagtgtat gcagattcag gggatataaa gacataaagg atgaatcttt tatggtataa       780
catggatatg aggaacagta tgtcttcaga atcttgttta gcatcacttt cttgttctgc       840
ctccacattt caatcgtcag aggattcagc agttgttaaa tggttaagat tcattttcct       900
ctctccatgt ccacaaagga ctcttctatc ttccattgat gtgctgcttt tgcttacttt       960
cattgtattt gcagtacaaa agttgtactc aaagttgagg tccaatgagc actctacttc      1020
tagcattgat aagcctctaa ttgcacacaa caggacttct gttagaacca atctttggtt      1080
taagctgtct ctgattttgt cagctatttt agccttatct tctatagttt tatgcatttt      1140
ggttattgtg ggaaattccc agtcgccttg gaaagtcata gatggactgt attggttgtt      1200
tcaggcgatt acacatgttg taatcactat actaatagtt catgagaaaa gatttcacgc      1260
tatttcccat ccactgtccc tgcgcgtgtt ttggattgca aactttgtag ttatgagttt      1320
gttctttggt tgtgggatca caaggcttgt gtcacttaag gaaattgatc ctaatttaag      1380
```

```
aatgatgat ataagttcat tagtttcatt tcctatttct gttgttctct tcattgttgc    1440
cattaaaggt tcgaccggag ttgctgtaat tagtgattct gaatctcact taagtgatga    1500
aaccaatggt tatgaactcc tggataaatc cagtgtgagt ggctttgctt cagcttctct    1560
aatatcgaaa gccttttgga tttggatgaa ccctttactg caaaaaggtt acaagtcacc    1620
tctcaagatt gatgaagttc cttcactttc cccactgcat agagcagaga aaatgtctca    1680
acttttcgaa agaaattggc ctaaacctga agaaatatca aagcatcctg tccgaacaac    1740
attgctgcgt tgcttttgga aggaagttat ttttactgcc attcttgcag taattagggt    1800
atgtgttatg tatgtagggc aacactcat acaaagattt gttgattaca cagcaggaaa     1860
gaggacatct ccttatgaag gatactacct tataggaact ctcctaatag ccaaatttgt    1920
ggaagttcta acctctcatc agttcaactt taactcccaa aagcttggca tgcttattcg    1980
agcgacactt ctcacttctt tgtataagaa ggggttaagg ttgtcatgct cagctagaca    2040
ggctcatggt gttggacaga ttgtaaatta tatggccgtc gatgctcagc agctgtccga    2100
tatgatgcta cagctacatt ccatttggct catgccattg caagtttctg tggctttagg    2160
catcctttat acttacctcg gtgcttcaac tgttgtaacg ctagctggac ttgcagcagt    2220
gatggtattt gtggtgtttg gaactaaaag aaacaacagg tttcaattta acatcatgaa    2280
gaatcgtgat tctagaatga aagcgacaaa tgagatgctt aattatatgc gcgttataaa    2340
gttccaggca tgggaagaac attttaacaa aagaattgaa tccttccgcg aatccgagta    2400
tggatggttg tccaagttct tgtactcaat cgctgggaat atcattgtct tgtggagcac    2460
tcctcttcta gtggctacac tcacttttgg aagtgcaatc ttgttgggaa tcccgcttgg    2520
tgcagggaca gtgttcactg caacatctct cttcaagatg ttgcaggaac cgatcagggc    2580
tttccctcaa tccatgatct cacttttcaca agcaatgata tctcttgata gattggacaa    2640
atatatgatg agtaaggagt tagtggataa agctgtggaa agactagaag ttgtggggg    2700 tacaattgct atgcaggtga agatggagc tttttgctgg gatgatgaaa acagtaaaga     2760
agaattgaaa aatgtaaact ttgagattag aaaaggagag cttgcagcag tagtggggac    2820
agttggggcg gggaagtctt ccctccttgc atctgtactt ggtgagatgc acaagttgtc    2880
gggtcaggta tggctctcat ccttctgttt gtttgattaa tacaaacttt gctgccaatt    2940 acctttgcc ccttgttgct acctcttttc tgtggtataa aaaattaatg taggctaatg     3000
tgtagagtgg aggtattata tgcagaacaa ttgcaatcaa gcaattacct gtgagatact    3060
attttgtttt catattagtg gactggtaca ttctcattgg tgtatcgttt gatctccacc    3120
aaagcagagg ttttactggc cgacagagtc aaactactgt gcttcactcc ttttactcca    3180
atccttagta gtctttgctt ctaatgaact tcaagcgtgt aatagaaaca ccattatatt    3240
attagctgat tagttacttt acaattccag agcatattta cattttctgc ttggttgtct    3300
attactctgg ataacagtcc taaatgcaag caaaatcaac tgtgttttca gtcttgagct    3360
gaccaattag ttcatgatgt cctcagcttg tccaagctgg tgcctcaccg gaattatgtg    3420
ggaccttcgt acttaatcaa ctagttcacc ttcttcttaa aaatattgaa tgatttgatt    3480
ggttaatagt tccttaaatg tagtaattat ttgctaactt actttaccaa cccccttgtcc   3540 aacaggtcac aatttgtggt tcaactgcct atgttgcaca acatcgtgg attcagaatg     3600 gcacgataca agaaaatatc ctgtttggta tgccaatgaa cagagacaga tacaaggaag    3660
tgatccgggt ttgctgcttg gagaaggact tggaaataat ggagtttgga gaccagactg    3720
aaataggaga acgtggcatc aacctcagtg gtggtcagaa gcagcgaatc cagcttgcaa    3780
```

```
gagctgttta ccaggactgt gatatttatc ttctagatga tgtattcagt gcagttgatg   3840
ctcacactgg ctctgaaatc ttcaaggtta gaagtccaca atgtcatgtg tcattgaaga   3900
tttaatttaa gatagaaatt acattgtttc attctgcaaa ttatggacct atcagagaaa   3960
aatcatggat tttgaatggc tactttcccc agtgaagaca catatcattt cctgggagga   4020
agatgtgaaa gtggcaagct atttactcca aaaagtataa tctaaaagac ttttattaag   4080
tttggaaggc ttaatccatc atttgttatc tgttgtctac ttgtctttat taaaattctt   4140
cttagtccaa tcactttcga tgaagttgac tagtcttagt cacctgaata ctttaaatct   4200
ttgccttggt gtctctatat tttcagccat ctcaattccg aagctcatat ttgttttctc   4260
tttgtaatgt ccatctgaaa gtttcatgct ttttttgcagg aatgtgtgag gggaattctt   4320
aaagataaaa ccattttgct tgtcacacac caagttgact tcttgcataa tgttgacctg   4380
atccttgtaa gtttcagagt gttttatcaa cccctttgga accaagtgtc aagagtagtg   4440
tttcttggtt gttaaatgat tcacatgtgt gttggtttct ataaaacctg aactttatgt   4500
tttatcagag tgttttgctt tcttgaaggt catgcgagat gggatgatcg tgcaatctgg   4560
caaatataat gagatattag aagctggaat ggattttaaa gagctagtag ctgcacatga   4620
gacctcttta gaacttgttg acgtggaaac aaccaaagag agcaatgcct cccttgaaga   4680
atcaaaatct tctcgaagat tatctaagga agaaaacgga gatgataaat ctcaacagtc   4740
tacatctgat aggggggatt ctaaacttat aaaggaagaa gaaagagaaa ctggaaaagt   4800
cagtcctcgt gtgtacaagc tatatattac tgaagctttt ggatggtggg gtgtagtgct   4860
agttatcttg ttttcgttct tgtggcaaag ttctctaatg gcaagtgatt attggctggc   4920
atatgaaact tcagcggatc gtgccatgtc cttcaatcct tctctgttta ttgggatata   4980
cggtgttatt gcagttgttt cttcgttgct gatagtgatc aggatgtatt ttgtgacact   5040 tatgggctc aagactgccc aaatattttt cggacagatt ctttacagca tactgcatgc   5100
tcctatgtca ttttttgaca aacaccttc cggaagaatt ctgagtcggg taaatttctg   5160
aggacaagtt tttccttttg catgtaaatt caaactttgc tgcttagatg attaaataat   5220
gaaaaatatc cattgcatgt tttaatgtgt atgacatgtt agaattttga atagaagttc   5280
attcactgat gttgagatgt tttgtttttt ttctgcaggc atctaatgat cagaccaaca   5340
ttgatgtctt cctcccgttt tttatgaatc tcacttggc catgtttatc acactgctcg   5400
gcatcatcat catcacatgc caatattctt ggcctaccgt actactttg attcctctgg   5460 gttggcttaa tatctggtac cgggtatgag cactgtttat aacagccgtc ctttttctct   5520
ttcttgtctg aactcaaatt tgaatccttt gtttagaggc aattagtctg ctctgagcat   5580
tttggctgac agttattatg tatattaaaa ggcaactttt ttattcgttc tgtccagcta   5640 aaactttta cttaaaatgt ggttaactgc atatttctgt gtctcctatt ttttgattat   5700
ttgcaactct gatcaatcta gatttgggga aggcttgttg ttagttgatg actagatact   5760
aagctcacat ctacattggt tgcaagtaga atttttcaagt tgtcattcac ttatattgtt   5820
tgaactagga gattagcatt cttctgcaag gagccctgaa tgcttgaaaa gttaaacaga   5880
aaagaaaaag ttcagggcag atagacataa tgtgttaaag taattcaatt ggagcacaga   5940
tatatgacat gtgttatttg ggagctacga aaaagataag gactattatg tagactacaa   6000
ttgaaataac aggtaattca tttctggttt acagggatat tatcttgcaa catctcgtga   6060
attgactcgg cttgactcaa ttacaaaagc acctgttatt catcatttct ctgaaagcat   6120
```

```
ctcaggtgtt atgactatac gttgctttag gaagcaggag atgttttgta acgagaatgt      6180
aaaccgagtg aattccaatc tgcgaatgga tttccacaac aatggatcca atgaatggtt      6240
gggctttcga ctggaattga tgggaagctt acttctttgt gtttctgcaa tgttcatgat      6300
tgtcttacct agcagcatca tcaagccagg tataacaccg tccaatgctc atttatggga      6360
attataaatt ctagtatttg ataatccttc tgtactttag atctacctgc tctactgaaa      6420
aatgaaatga gtatgaggaa atagaatatc cgttgagcat ttatgtcttt ctattaaaaa      6480
tttgcattct atcttcttgt ttcaagtcaa atcttgaac aactatatct agagaatttt       6540
ccttcttgtg aagtaatgca tatatacatc aagagaagtc agagttgctg aatgaaatag      6600
tagatcaaat ttaagtgttg tgcctataaa gaattgtatg gtgagattga atatagtggt      6660
catattattt tctcaatctt agtgattaaa gtattccata caaacagaca agcatttagt      6720
cgtgcattca ttggcactac aaaattatca accaagagta atattctttc agctttcctc      6780
tgtatatgtg tgttctattc tggagctgaa gataactaat attctttttt atttctacag      6840
aaaatgttgg tttgtcacta tcatatggct tgtctcttaa tagtgtccta ttctggtcca      6900
tctttgtgag ttgctttgtg gaaaataaaa tggtttctgt cgaaagatta aaacagttct      6960
cagaaatacc atcagaagca gagtggagaa agatggattt tctcccacct tcaagttggc      7020
caagccgtgg gaatgttgag cttgaaaacg tgcaggtaat aattctaact aattctgtgg      7080
ttgctatttg ctagcatttg cacaaaagga aaactataaa aagttcatag taaggaagag      7140
agggtagctg tattaacaag cctacagatt ctttaatttc aaatatgtta cgttgaatct      7200
ctatattgtt tgttctactg gtcaacaggt tagatatcgt ccgaacactc ctctagtgct      7260
taaaggagtt actctcagca ttagaggggg agagaagata ggtgttgttg gtcgtacagg      7320
gggtggaaaa tcaacattaa ttcaagtttt ctttcgtttg gtggagcctg cagctggaag      7380
aataatcatt gatgacgtag atatatccag acttgggctt catgatctta gatctcgctt      7440
cgggatcatt ccccaagagc cagtcctttt tgaaggaact gtgagaagca acattgaccc      7500
cattggacaa tattcagatg atgaaatttg gaaggtaatc taacttgctg actgaaataa      7560
tttacaaaaa tctcaaaata tagtacagag ttagccaaac atgtcttctg agtgctgaga      7620 tcttttttgga ttataaattc tgtaagagca acatactatt tgttagtgag aagaaaagca      7680
tatactccag tgttttgtta tctcccagaa tgtctctaac atgaaatcgt gtacattgca      7740
gagcctcgaa cgctgccaac tcaaagatgt ggtgtcttta aaacccgaaa aacttgattc      7800
accaggtaaa ttttcctcct ctacgtcatc cttgtggttc tttgcggaat tatgcaacca      7860 acttttatg tgtttcaaat atatatactg ataactgaat actgtcattg gtaaatcata       7920
gttgttgata acgagataa ctggagtgtc ggacagaggc agcttctttg cttgggaaga      7980
gtgatgctaa aacgtagcag acttctattt atggatgagg caactgcctc tgttgattca      8040
cagacagatg cagtgattca gaaaatcatc cgcgaggact ttgcggcctg tactataatc      8100
agcattgccc acagaatacc aacagtcatg gactgtgata gagttcttgt tatagatgca      8160
ggtgctgatt tctctccttt tactttgtac cttatttga atctggtaaa tgattattta     8220
tctgtatgtg atggtttcca accaatcata gtcagtacct ttatgaagaa attgcctaat      8280
gttagccaag tagtagtaaa tgcatgaagt cattagccta tttgttttgg attttgtgag      8340
tttcatactt caaactggaa gcttatgcta tactatctga tcccttgttt gtatagattg      8400 cttcttttc cttttctcg gatttatctt atatataagc ggacagagta aaagaatgta      8460
aacatgcgta atttgaccta ttatagcaga ttatttgtct tattttccag gtcgctgatt      8520
```

```
ccacttatta ggagtagtta cacgtatttta tcttttaagt gaaataatag tgtaaagttt    8580
cttttggcac tgtcggtgta aagaagttaa actcctttct ttaaccccgg catttcttat    8640
tcatgcagga atagcaaaag agtttgacaa accatctcgt ttgcttgaaa ggccttcact    8700
ttttggggct ttggttcaag aatatgccaa ccgatcctct gagctctaac cacactattt    8760
tggctttcat gccttttgct gtaaattgca gctatcttgg aggataggtg aaacaggaaa    8820
aataccatcc caaatgttac atagatttcc aaatagtgtt atctcctact aagctatcca    8880
gtagattttt ggaaatgtaa caatattggg attaacaatt gtaattgatg aatctattaa    8940
tcaaatacaa tgattattct gttatagatg tagtctgtgc aatgttatat agactgattt    9000
c                                                                   9001

<210> SEQ ID NO 2
<211> LENGTH: 7526
<212> TYPE: DNA
<213> ORGANISM: Nicotiana tabacum

<400> SEQUENCE: 2
atggatatga ggaacagtat gtcttcagaa tcttgtttag catcactttc ttgttctgcc      60
tccacatttc aatcgtcaga ggattcagca gttgttaaat ggttaagatt catttttcctc   120 tctccatgtc cacaaaggac tcttctatct tccattgatg tgctgctttt gcttactttc    180
attgtatttg cagtacaaaa gttgtactca aagttgaggt ccaatgagca ctctacttct    240
agcattgata agcctctaat tgcacacaac aggacttctg ttagaaccaa tctttggttt    300
aagctgtctc tgattttgtc agctatttta gccttatctt ctatagtttt atgcattttg    360
gttattgtgg gaaattccca gtcgccttgg aaagtcatag atggactgta ttggttgttt    420
caggcgatta cacatgttgt aatcactata ctaatagttc atgagaaaag atttcacgct    480
atttcccatc cactgtccct gcgcgtgttt tggattgcaa actttgtagt tatgagtttg    540
ttctttggtt gtgggatcac aaggcttgtg tcacttaagg aaattgatcc taatttaaga    600
atggatgata taagttcatt agtttcattt cctatttctg ttgttctctt cattgttgcc    660
attaaaggtt cgaccggagt tgctgtaatt agtgattctg aatctcactt aagtgatgaa    720
accaatggtt atgaactcct ggataaatcc agtgtgagtg ctttgcttc agcttctcta    780 atatcgaaag cctttggat ttggatgaac cctttactgc aaaaaggtta caagtcacct    840
ctcaagattg atgaagttcc ttcacttttcc ccactgcata gagcagagaa aatgtctcaa    900
cttttcgaaa gaaattggcc taaacctgaa gaaatatcaa agcatcctgt ccgaacaaca    960
ttgctgcgtt gcttttggaa ggaagttatt tttactgcca ttcttgcagt aattagggta   1020
tgtgttatgt atgtagggcc aacactcata caaagatttg ttgattacac agcaggaaag   1080
aggacatctc cttatgaagg atactacctt ataggaactc tcctaatagc caaatttgtg   1140
gaagttctaa cctctcatca gttcaacttt aactcccaaa agcttggcat gcttattcga   1200
gcgacacttc tcacttcttt gtataagaag gggttaaggt tgtcatgctc agctagacag   1260
gctcatggtg ttggacagat tgtaaattat atggccgtcg atgctcagca gctgtccgat   1320
atgatgctac agctacattc catttggctc atgccattgc aagtttctgt ggctttaggc   1380
atcctttata cttacctcgg tgcttcaact gttgtaacgc tagctggact tgcagcagtg   1440
atggtatttg tggtgtttgg aactaaaaga acaacaggt tcaatttaa catcatgaag   1500 aatcgtgatt ctagaatgaa agcgacaaat gagatgctta attatatgcg cgttataaag   1560
```

-continued

```
ttccaggcat gggaagaaca ttttaacaaa agaattgaat ccttccgcga atccgagtat   1620
ggatggttgt ccaagttctt gtactcaatc gctgggaata tcattgtctt gtggagcact   1680
cctcttctag tggctacact cacttttgga agtgcaatct tgttgggaat cccgcttggt   1740
gcagggacag tgttcactgc aacatctctc ttcaagatgt tgcaggaacc gatcagggct   1800
ttccctcaat ccatgatctc actttcacaa gcaatgatat ctcttgatag attggacaaa   1860
tatatgatga gtaaggagtt agtggataaa gctgtggaaa gactagaagg ttgtggggt    1920
acaattgcta tgcaggtgaa agatggagct ttttgctggg atgatgaaaa cagtaaagaa   1980
gaattgaaaa atgtaaactt tgagattaga aaaggagagc ttgcagcagt agtggggaca   2040
gttgggcgg ggaagtcttc cctccttgca tctgtacttg gtgagatgca caagttgtcg    2100
ggtcaggtat ggctctcatc cttctgtttg tttgattaat acaaactttg ctgccaatta   2160
cctttgccc cttgttgcta cctcttttct gtggtataaa aaattaatgt aggctaatgt    2220
gtagagtgga ggtattatat gcagaacaat tgcaatcaag caattacctg tgagatacta   2280
ttttgttttc atattagtgg actggtacat tctcattggt gtatcgtttg atctccacca   2340
aagcagaggt tttactggcc gacagagtca aactactgtg cttcactcct tttactccaa   2400
tccttagtag tctttgcttc taatgaactt caagcgtgta atagaaacac cattatatta   2460
ttagctgatt agttacttta caattccaga gcatatttac attttctgct tggttgtcta   2520
ttactctgga taacagtcct aaatgcaagc aaaatcaact gtgttttcag tcttgagctg   2580
accaattagt tcatgatgtc ctcagcttgt ccaagctggt gcctcaccgg aattatgtgg   2640
gaccttcgta cttaatcaac tagttcacct tcttcttaaa aatattgaat gatttgattg   2700
gttaatagtt ccttaaatgt agtaattatt tgctaactta ctttaccaac cccttgtcca   2760
acaggtcaca atttgtggtt caactgccta tgttgcacaa acatcgtgga ttcagaatgg   2820
cacgatacaa gaaaatatcc tgtttggtat gccaatgaac agagacagat acaaggaagt   2880
gatccgggtt tgctgcttgg agaaggactt ggaaataatg gagtttggag accagactga   2940
aataggagaa cgtggcatca acctcagtgg tggtcagaag cagcgaatcc agcttgcaag   3000
agctgtttac caggactgtg atatttatct tctagatgat gtattcagtg cagttgatgc   3060
tcacactggc tctgaaatct tcaaggttag aagtccacaa tgtcatgtgt cattgaagat   3120
ttaatttaag atagaaatta cattgtttca ttctgcaaat tatggaccta tcagagaaaa   3180
atcatggatt ttgaatggct actttcccca gtgaagacac atatcatttc ctgggaggaa   3240
gatgtgaaag tggcaagcta tttactccaa aaagtataat ctaaaagact tttattaagt   3300
ttggaaggct taatccatca tttgttatct gttgtctact tgtctttatt aaaattcttc   3360
ttagtccaat cactttcgat gaagttgact agtcttagtc acctgaatac tttaaatctt   3420
tgccttggtg tctctatatt ttcagccatc tcaattccga agctcatatt tgttttctct   3480
ttgtaatgtc catctgaaag tttcatgctt ttttgcagga atgtgtgagg ggaattctta   3540
aagataaaac cattttgctt gtcacacacc aagttgactt cttgcataat gttgacctga   3600
tccttgtaag tttcagagtg ttttatcaac cccttggaa ccaagtgtca agagtagtgt    3660
ttcttggttg ttaaatgatt cacatgtgtg ttggtttcta taaacctga actttatgtt    3720
ttatcagagt gttttgcttt cttgaaggtc atgcgagatg ggatgatcgt gcaatctggc   3780
aaatataatg agatattaga agctggaatg gatttaaag agctagtagc tgcacatgag    3840
acctctttag aacttgttga cgtggaaaca accaaagaga gcaatgcctc ccttgaagaa   3900
tcaaaatctt ctcgaagatt atctaaggaa gaaaacggag atgataaatc tcaacagtct   3960
```

```
acatctgata gggggattc taaacttata aggaagaag aaagagaaac tggaaaagtc    4020
agtcctcgtg tgtacaagct atatattact gaagcttttg gatggtgggg tgtagtgcta    4080
gttatcttgt tttcgttctt gtggcaaagt tctctaatgg caagtgatta ttggctggca    4140
tatgaaactt cagcggatcg tgccatgtcc ttcaatcctt ctctgtttat gggatatac    4200
ggtgttattg cagttgtttc ttcgttgctg atagtgatca ggatgtattt tgtgacactt    4260
atggggctca agactgccca aatatttttc ggacagattc tttacagcat actgcatgct    4320
cctatgtcat ttttgacac aacaccttcc ggaagaattc tgagtcgggt aaatttctga    4380
ggacaagttt ttccttttgc atgtaaattc aaactttgct gcttagatga ttaaataatg    4440
aaaaatatcc attgcatgtt ttaatgtgta tgacatgtta gaattttgaa tagaagttca    4500
ttcactgatg ttgagatgtt ttgttttttt tctgcaggca tctaatgatc agaccaacat    4560
tgatgtcttc ctcccgtttt ttatgaatct cactttggcc atgtttatca cactgctcgg    4620
catcatcatc atcacatgcc aatattcttg gcctaccgta ctactttga ttcctctggg    4680
ttggcttaat atctggtacc gggtatgagc actgtttata acagccgtcc ttttttcttt    4740
tcttgtctga actcaaattt gaatccttg tttagaggca attagtctgc tctgagcatt    4800
ttggctgaca gttattatgt atattaaaag gcaacttttt tattcgttct gtccagctaa    4860
aactttttac ttaaaatgtg gttaactgca tatttctgtg tctcctattt tttgattatt    4920
tgcaactctg atcaatctag atttggggaa ggcttgttgt tagttgatga ctagatacta    4980
agctcacatc tacattggtt gcaagtagaa ttttcaagtt gtcattcact tatattgttt    5040
gaactaggag attagcattc ttctgcaagg agccctgaat gcttgaaaag ttaaacagaa    5100
aagaaaaagt tcagggcaga tagacataat gtgttaaagt aattcaattg gagcacagat    5160
atatgacatg tgttatttgg gagctacgaa aaagataagg actattatgt agactacaat    5220
tgaaataaca ggtaattcat ttctggttta cagggatatt atcttgcaac atctcgtgaa    5280
ttgactcggc ttgactcaat tacaaaagca cctgttattc atcatttctc tgaaagcatc    5340
tcaggtgtta tgactatacg ttgctttagg aagcaggaga tgttttgtaa cgagaatgta    5400
aaccgagtga attccaatct gcgaatggat ttccacaaca atggatccaa tgaatggttg    5460
ggctttcgac tggaattgat gggaagctta cttctttgtg tttctgcaat gttcatgatt    5520
gtcttaccta gcagcatcat caagccaggt ataacaccgt ccaatgctca tttatgggaa    5580
ttataaattc tagtatttga taatccttct gtactttaga tctacctgct ctactgaaaa    5640
atgaaatgag tatgaggaaa tagaatatcc gttgagcatt tatgtctttc tattaaaaat    5700
ttgcattcta tcttcttgtt tcaagtcaaa atcttgaaca actatatcta gagaattttc    5760
cttcttgtga agtaatgcat atatacatca agagaagtca gagttgctga atgaaatagt    5820
agatcaaatt taagtgttgt gcctataaag aattgtatgg tgagattgaa tatagtggtc    5880
atattatttt ctcaatctta gtgattaaag tattccatac aaacagacaa gcatttagtc    5940
gtgcattcat tggcactaca aaattatcaa ccaagagtaa tattctttca gctttcctct    6000
gtatatgtgt gttctattct ggagctgaag ataactaata ttcttttta tttctacaga    6060
aaatgttggt ttgtcactat catatggctt gtctcttaat agtgtcctat tctggtccat    6120
ctttgtgagt tgctttgtgg aaaataaaat ggtttctgtc gaaagattaa aacagttctc    6180
agaaatacca tcagaagcag agtggagaaa gatggatttt ctcccacctt caagttggcc    6240
aagccgtggg aatgttgagc ttgaaaacgt gcaggtaata attctaacta attctgtggt    6300
```

-continued

```
tgctatttgc tagcatttgc acaaaaggaa aactataaaa agttcatagt aaggaagaga    6360
gggtagctgt attaacaagc ctacagattc tttaatttca aatatgttac gttgaatctc    6420
tatattgttt gttctactgg tcaacaggtt agatatcgtc cgaacactcc tctagtgctt    6480
aaaggagtta ctctcagcat tagagggga gagaagatag gtgttgttgg tcgtacaggg    6540
ggtggaaaat caacattaat tcaagttttc tttcgtttgg tggagcctgc agctggaaga    6600
ataatcattg atgacgtaga tatatccaga cttgggcttc atgatcttag atctcgcttc    6660
gggatcattc cccaagagcc agtccttttt gaaggaactg tgagaagcaa cattgacccc    6720
attggacaat attcagatga tgaaatttgg aaggtaatct aacttgctga ctgaaataat    6780
ttacaaaaat ctcaaaatat agtacagagt tagccaaaca tgtcttctga gtgctgagat    6840
cttttttggat tataaattct gtaagagcaa catactattt gttagtgaga agaaaagcat    6900
atactccagt gttttgttat ctcccagaat gtctctaaca tgaaatcgtg tacattgcag    6960
agcctcgaac gctgccaact caaagatgtg gtgtctttaa aacccgaaaa acttgattca    7020
ccaggtaaat tttcctcctc tacgtcatcc ttgtggttct ttgcggaatt atgcaaccaa    7080
cttttttatgt gtttcaaata tatactgaa taactgaata ctgtcattgg taaatcatag    7140
ttgttgataa cggagataac tggagtgtcg gacagaggca gcttctttgc ttgggaagag    7200
tgatgctaaa acgtagcaga cttctatttta tggatgaggc aactgcctct gttgattcac    7260
agacagatgc agtgattcag aaaatcatcc gcgaggactt tgcggcctgt actataatca    7320
gcattgccca cagaatacca acagtcatgg actgtgatag agttcttgtt atagatgcag    7380
gtgctgattt ctctccttttt actttgtacc ttattttgaa tctggtaaat gattattttat    7440
ctgtatgtga tggtttccaa ccaatcatag tcagtacctt tatgaagaaa ttgcctaatg    7500
ttagccaagt agtagtaaat gcatga                                          7526

<210> SEQ ID NO 3
<211> LENGTH: 102
<212> TYPE: DNA
<213> ORGANISM: Nicotiana tabacum

<400> SEQUENCE: 3
gttagaacca atctttggtt taagctgtct ctgattttgt cagctatttt agccttatct     60
tctatagttt tatgcatttt ggttattgtg ggaaattccc ag                       102

<210> SEQ ID NO 4
<211> LENGTH: 658
<212> TYPE: DNA
<213> ORGANISM: Nicotiana tabacum

<400> SEQUENCE: 4
gtatggctct catccttctg tttgtttgat taatacaaac tttgctgcca attacctttt     60
gccccttgtt gctacctctt ttctgtggta taaaaaatta atgtaggcta atgtgtagag    120
tggaggtatt atatgcagaa caattgcaat caagcaatta cctgtgagat actattttgt    180
tttcatatta gtggactggt acattctcat ggtgtatcg tttgatctcc accaaagcag    240
aggttttact ggccgacaga gtcaaactac tgtgcttcac tccttttact ccaatcctta    300
gtagtctttg cttctaatga acttcaagcg tgtaatagaa acaccattat attattagct    360
gattagttac tttacaattc cagagcatat ttacattttc tcttggttg tctattactc    420
tggataacag tcctaaatgc aagcaaaatc aactgtgttt tcagtcttga gctgaccaat    480
tagttcatga tgtcctcagc ttgtccaagc tggtgcctca ccggaattat gtgggacctt    540
```

```
cgtacttaat caactagttc accttcttct taaaaatatt gaatgatttg attggttaat    600
agttccttaa atgtagtaat tatttgctaa cttactttac caacccctg tccaacag      658

<210> SEQ ID NO 5
<211> LENGTH: 433
<212> TYPE: DNA
<213> ORGANISM: Nicotiana tabacum

<400> SEQUENCE: 5
gttagaagtc cacaatgtca tgtgtcattg aagatttaat ttaagataga aattacattg     60
tttcattctg caaattatgg acctatcaga gaaaaatcat ggattttgaa tggctacttt    120
ccccagtgaa gacacatatc atttcctggg aggaagatgt gaaagtggca agctatttac    180
tccaaaaagt ataatctaaa agactttat taagtttgga aggcttaatc catcatttgt     240
tatctgttgt ctacttgtct ttattaaaat tcttcttagt ccaatcactt tcgatgaagt    300
tgactagtct tagtcacctg aatactttaa atctttgcct tggtgtctct atattttcag    360
ccatctcaat tccgaagctc atatttgttt tctctttgta atgtccatct gaaagtttca    420 tgctttttg cag                                                       433

<210> SEQ ID NO 6
<211> LENGTH: 142
<212> TYPE: DNA
<213> ORGANISM: Nicotiana tabacum

<400> SEQUENCE: 6
gtaagtttca gagtgtttta tcaacccctt tggaaccaag tgtcaagagt agtgtttctt     60
ggttgttaaa tgattcacat gtgtgttggt ttctataaaa cctgaacttt atgttttatc    120
agagtgtttt gctttcttga ag                                            142

<210> SEQ ID NO 7
<211> LENGTH: 169
<212> TYPE: DNA
<213> ORGANISM: Nicotiana tabacum

<400> SEQUENCE: 7
gtaaatttct gaggacaagt ttttcctttt gcatgtaaat tcaaactttg ctgcttagat     60
gattaaataa tgaaaaatat ccattgcatg ttttaatgtg tatgacatgt tagaattttg    120
aatagaagtt cattcactga tgttgagatg ttttgttttt tttctgcag               169

<210> SEQ ID NO 8
<211> LENGTH: 551
<212> TYPE: DNA
<213> ORGANISM: Nicotiana tabacum

<400> SEQUENCE: 8
gtatgagcac tgtttataac agccgtcctt ttttcttttc ttgtctgaac tcaaatttga     60
atcctttgtt tagaggcaat tagtctgctc tgagcatttt ggctgacagt tattatgtat    120
attaaaaggc aacttttta ttcgttctgt ccagctaaaa cttttactt aaaatgtggt      180 taactgcata tttctgtgtc tcctattttt tgattatttg caactctgat caatctagat    240
ttggggaagg cttgttgtta gttgatgact agatactaag ctcacatcta cattggttgc    300
aagtagaatt ttcaagttgt cattcactta tattgtttga actaggagat tagcattctt    360
ctgcaaggag ccctgaatgc ttgaaaagtt aaacagaaaa gaaaaagttc agggcagata    420
```

```
gacataatgt gttaaagtaa ttcaattgga gcacagatat atgacatgtg ttatttggga    480
gctacgaaaa agataaggac tattatgtag actacaattg aaataacagg taattcattt    540
ctggtttaca g                                                          551

<210> SEQ ID NO 9
<211> LENGTH: 511
<212> TYPE: DNA
<213> ORGANISM: Nicotiana tabacum

<400> SEQUENCE: 9
gtataacacc gtccaatgct catttatggg aattataaat tctagtattt gataatcctt    60
ctgtacttta gatctacctg ctctactgaa aaatgaaatg agtatgagga aatagaatat    120
ccgttgagca tttatgtctt tctattaaaa atttgcattc tatcttcttg tttcaagtca    180
aaatcttgaa caactatatc tagagaattt tccttcttgt gaagtaatgc atatatacat    240
caagagaagt cagagttgct gaatgaaata gtagatcaaa tttaagtgtt gtgcctataa    300
agaattgtat ggtgagattg aatatagtgg tcatattatt ttctcaatct tagtgattaa    360
agtattccat acaaacagac aagcatttag tcgtgcattc attggcacta caaaattatc    420
aaccaagagt aatattcttt cagctttcct ctgtatatgt gtgttctatt ctggagctga    480
agataactaa tattcttttt tatttctaca g                                    511

<210> SEQ ID NO 10
<211> LENGTH: 173
<212> TYPE: DNA
<213> ORGANISM: Nicotiana tabacum

<400> SEQUENCE: 10
gtaataattc taactaattc tgtggttgct atttgctagc atttgcacaa aaggaaaact    60
ataaaaagtt catagtaagg aagagagggt agctgtatta acaagcctac agattcttta    120
atttcaaata tgttacgttg aatctctata ttgtttgttc tactggtcaa cag           173

<210> SEQ ID NO 11
<211> LENGTH: 207
<212> TYPE: DNA
<213> ORGANISM: Nicotiana tabacum

<400> SEQUENCE: 11
gtaatctaac ttgctgactg aaataattta caaaaatctc aaaatatagt acagagttag    60
ccaaacatgt cttctgagtg ctgagatctt tttggattat aaattctgta agagcaacat    120
actatttgtt agtgagaaga aaagcatata ctccagtgtt ttgttatctc ccagaatgtc    180
tctaacatga aatcgtgtac attgcag                                         207

<210> SEQ ID NO 12
<211> LENGTH: 116
<212> TYPE: DNA
<213> ORGANISM: Nicotiana tabacum

<400> SEQUENCE: 12
gtaaattttc ctcctctacg tcatccttgt ggttctttgc ggaattatgc aaccaacttt    60
ttatgtgttt caaatatata tactgataac tgaatactgt cattggtaaa tcatag        116

<210> SEQ ID NO 13
<211> LENGTH: 279
<212> TYPE: DNA
<213> ORGANISM: Nicotiana tabacum
```

<400> SEQUENCE: 13

```
atggatatga ggaacagtat gtcttcagaa tcttgtttag catcactttc ttgttctgcc    60
tccacatttc aatcgtcaga ggattcagca gttgttaaat ggttaagatt cattttcctc   120
tctccatgtc cacaaaggac tcttctatct tccattgatg tgctgctttt gcttactttc   180
attgtatttg cagtacaaaa gttgtactca aagttgaggt ccaatgagca ctctacttct   240
agcattgata agcctctaat tgcacacaac aggacttct                          279
```

<210> SEQ ID NO 14
<211> LENGTH: 1725
<212> TYPE: DNA
<213> ORGANISM: Nicotiana tabacum

<400> SEQUENCE: 14

```
tcgccttgga aagtcataga tggactgtat tggttgtttc aggcgattac acatgttgta    60
atcactatac taatagttca tgagaaaaga tttcacgcta tttcccatcc actgtccctg   120
cgcgtgtttt ggattgcaaa cttgtagtt atgagtttgt tctttggttg tgggatcaca   180
aggcttgtgt cacttaagga aattgatcct aatttaagaa tggatgatat aagttcatta   240
gtttcatttc ctatttctgt tgttctcttc attgttgcca ttaaaggttc gaccggagtt   300
gctgtaatta gtgattctga atctcactta agtgatgaaa ccaatggtta tgaactcctg   360
gataaatcca gtgtgagtgg cttttgcttca gcttctctaa tatcgaaagc cttttggatt   420
tggatgaacc ctttactgca aaaaggttac aagtcacctc tcaagattga tgaagttcct   480
tcactttccc cactgcatag agcagagaaa atgtctcaac ttttcgaaag aaattggcct   540
aaacctgaag aaatatcaaa gcatcctgtc cgaacaacat tgctgcgttg cttttggaag   600
gaagttattt ttactgccat tcttgcagta attagggtat gtgttatgta tgtagggcca   660
acactcatac aaagatttgt tgattacaca gcaggaaaga ggacatctcc ttatgaagga   720
tactaccta taggaactct cctaatagcc aaatttgtgg aagttctaac ctctcatcag   780
ttcaacttta actcccaaaa gcttggcatg cttattcgag cgacacttct cacttctttg   840
tataagaagg ggttaaggtt gtcatgctca gctagacagg ctcatggtgt tggacagatt   900
gtaaattata tggccgtcga tgctcagcag ctgtccgata tgatgctaca gctacattcc   960
atttggctca tgccattgca agtttctgtg gctttaggca tcctttatac ttacctcggt  1020
gcttcaactg ttgtaacgct agctggactt gcagcagtga tggtatttgt ggtgtttgga  1080
actaaaagaa acaacaggtt tcaatttaac atcatgaaga atcgtgattc tagaatgaaa  1140
gcgacaaatg agatgcttaa ttatatgcgc gttataaagt tccaggcatg gaagaacat   1200
tttaacaaaa gaattgaatc cttccgcgaa tccgagtatg gatggttgtc caagttcttg  1260
tactcaatcg ctgggaatat cattgtcttg tggagcactc ctcttctagt ggctacactc  1320
acttttggaa gtgcaatctt gttgggaatc ccgcttggtg cagggacagt gttcactgca  1380
acatctctct tcaagatgtt gcaggaaccg atcagggctt tccctcaatc catgatctca  1440
ctttcacaag caatgatatc tcttgataga ttggacaaat atatgatgag taaggagtta  1500
gtggataaag ctgtggaaag actagaaggt tgtgggggta caattgctat gcaggtgaaa  1560
gatggagctt tttgctggga tgatgaaaac agtaaagaag aattgaaaaa tgtaaacttt  1620
gagattagaa aggagagct tgcagcagta gtggggacag ttggggcggg gaagtcttcc  1680
ctccttgcat ctgtacttgg tgagatgcac aagttgtcgg gtcag              1725
```

<210> SEQ ID NO 15
<211> LENGTH: 320
<212> TYPE: DNA
<213> ORGANISM: Nicotiana tabacum

<400> SEQUENCE: 15

```
gtcacaattt gtggttcaac tgcctatgtt gcacaacatc gtggattcag aatggcacga      60
tacaagaaaa tatcctgttt ggtatgccaa tgaacagaga cagatacaag gaagtgatcc     120
gggtttgctg cttggagaag gacttggaaa taatggagtt tggagaccag actgaaatag     180
gagaacgtgg catcaacctc agtggtggtc agaagcagcg aatccagctt gcaagagctg     240
tttaccagga ctgtgatatt tatcttctag atgatgtatt cagtgcagtt gatgctcaca     300
ctggctctga aatcttcaag                                                 320
```

<210> SEQ ID NO 16
<211> LENGTH: 87
<212> TYPE: DNA
<213> ORGANISM: Nicotiana tabacum

<400> SEQUENCE: 16

```
gaatgtgtga ggggaattct taaagataaa accattttgc ttgtcacaca ccaagttgac      60
ttcttgcata atgttgacct gatcctt                                          87
```

<210> SEQ ID NO 17
<211> LENGTH: 621
<212> TYPE: DNA
<213> ORGANISM: Nicotiana tabacum

<400> SEQUENCE: 17

```
gtcatgcgag atgggatgat cgtgcaatct ggcaaatata atgagatatt agaagctgga      60
atggatttta aagagctagt agctgcacat gagacctctt tagaacttgt tgacgtggaa     120
acaaccaaag agagcaatgc ctcccttgaa gaatcaaaat cttctcgaag attatctaag     180
gaagaaaacg gagatgataa atctcaacag tctacatctg ataggggga ttctaaactt      240
ataaaggaag aagaaagaga aactggaaaa gtcagtcctc gtgtgtacaa gctatatatt     300
actgaagctt ttggatggtg gggtgtagtg ctagttatct tgttttcgtt cttgtggcaa     360
agttctctaa tggcaagtga ttattggctg gcatatgaaa cttcagcgga tcgtgccatg     420
tccttcaatc cttctctgtt tattgggata tacggtgtta ttgcagttgt tcttcgttg     480
ctgatagtga tcaggatgta ttttgtgaca cttatgggc tcaagactgc ccaaatattt     540
ttcggacaga ttctttacag catactgcat gctcctatgt cattttttga cacaacacct     600
tccggaagaa ttctgagtcg g                                               621
```

<210> SEQ ID NO 18
<211> LENGTH: 165
<212> TYPE: DNA
<213> ORGANISM: Nicotiana tabacum

<400> SEQUENCE: 18

```
gcatctaatg atcagaccaa cattgatgtc ttcctcccgt tttttatgaa tctcactttg      60
gccatgtttta tcacactgct cggcatcatc atcatcacat gccaatattc ttggcctacc    120
gtactacttt tgattcctct gggttggctt aatatctggt accgg                     165
```

<210> SEQ ID NO 19
<211> LENGTH: 295

<212> TYPE: DNA
<213> ORGANISM: Nicotiana tabacum

<400> SEQUENCE: 19

```
ggatattatc ttgcaacatc tcgtgaattg actcggcttg actcaattac aaaagcacct      60
gttattcatc atttctctga aagcatctca ggtgttatga ctatacgttg ctttaggaag     120
caggagatgt tttgtaacga gaatgtaaac cgagtgaatt ccaatctgcg aatggatttc     180
cacaacaatg gatccaatga atggttgggc tttcgactgg aattgatggg aagcttactt     240
ctttgtgttt ctgcaatgtt catgattgtc ttacctagca gcatcatcaa gccag          295
```

<210> SEQ ID NO 20
<211> LENGTH: 215
<212> TYPE: DNA
<213> ORGANISM: Nicotiana tabacum

<400> SEQUENCE: 20

```
aaaatgttgg tttgtcacta tcatatggct tgtctcttaa tagtgtccta ttctggtcca      60
tctttgtgag ttgctttgtg gaaaataaaa tggtttctgt cgaaagatta aaacagttct     120
cagaaatacc atcagaagca gagtggagaa agatggattt tctcccacct tcaagttggc     180
caagccgtgg gaatgttgag cttgaaaacg tgcag                                 215
```

<210> SEQ ID NO 21
<211> LENGTH: 306
<212> TYPE: DNA
<213> ORGANISM: Nicotiana tabacum

<400> SEQUENCE: 21

```
gttagatatc gtccgaacac tcctctagtg cttaaaggag ttactctcag cattagaggg      60
ggagagaaga taggtgttgt tggtcgtaca gggggtggaa aatcaacatt aattcaagtt     120
ttctttcgtt tggtggagcc tgcagctgga agaataatca ttgatgacgt agatatatcc     180
agacttgggc ttcatgatct tagatctcgc ttcgggatca ttccccaaga gccagtcctt     240
tttgaaggaa ctgtgagaag caacattgac cccattggac aatattcaga tgatgaaatt     300
tggaag                                                                 306
```

<210> SEQ ID NO 22
<211> LENGTH: 64
<212> TYPE: DNA
<213> ORGANISM: Nicotiana tabacum

<400> SEQUENCE: 22

```
agcctcgaac gctgccaact caaagatgtg gtgtctttaa aacccgaaaa acttgattca      60
ccag                                                                    64
```

<210> SEQ ID NO 23
<211> LENGTH: 1281
<212> TYPE: DNA
<213> ORGANISM: Nicotiana tabacum

<400> SEQUENCE: 23

```
aagagccagt ccttttgaa ggaactgtga gaagcaacat tgaccccatt ggacaatatt       60
cagatgatga atttggaag gtaatctaac ttgctgactg aaataattta caaaaatctc      120
aaaatatagt acagagttag ccaaacatgt cttctgagtg ctgagatctt tttggattat     180
aaattctgta agagcaacat actatttgtt agtgagaaga aaagcatata ctccagtgtt     240
```

-continued

```
ttgttatctc ccagaatgtc tctaacatga aatcgtgtac attgcagagc ctcgaacgct    300
gccaactcaa agatgtggtg tcttaaaaac ccgaaaaact tgattcacca ggtaaatttt    360
cctcctctac gtcatccttg tggttctttg cggaattatg caaccaactt tttatgtgtt    420
tcaaatatat atactgataa ctgaatactg tcattggtaa atcatagttg ttgataacgg    480
agataactgg agtgtcggac agaggcagct tctttgcttg ggaagagtga tgctaaaacg    540
tagcagactt ctatttatgg atgaggcaac tgcctctgtt gattcacaga cagatgcagt    600
gattcagaaa atcatccgcg aggactttgc ggcctgtact ataatcagca ttgcccacag    660
aataccaaca gtcatggact gtgatagagt tcttgttata gatgcaggtg ctgatttctc    720
tccttttact ttgtacctta ttttgaatct ggtaaatgat tatttatctg tatgtgatgg    780
tttccaacca atcatagtca gtaccttat gaagaaattg cctaatgtta gccaagtagt    840
agtaaatgca tgaagtcatt agcctatttg ttttggattt tgtgagtttc atacttcaaa    900
ctggaagctt atgctatact atctgatccc ttgtttgtat agattgcttt cttttccttt    960
ttctcggatt tatcttatat ataagcggac agagtaaaag aatgtaaaca tgcgtaattt   1020
gacctattat agcagattat ttgtcttatt ttccaggtcg ctgattccac ttattaggag   1080
tagttacacg tatttatctt ttaagtgaaa taatagtgta aagtttcttt tggcactgtc   1140
ggtgtaaaga agttaaactc ctttctttaa ccccggcatt tcttattcat gcaggaatag   1200
caaaagagtt tgacaaacca tctcgtttgc ttgaaaggcc ttcactttt ggggctttgg    1260
ttcaagaata tgccaaccga t                                             1281
```

<210> SEQ ID NO 24
<211> LENGTH: 1474
<212> TYPE: PRT
<213> ORGANISM: Nicotiana tabacum

<400> SEQUENCE: 24

```
Met Asp Met Arg Asn Ser Met Ser Ser Glu Ser Cys Leu Ala Ser Leu
1               5                   10                  15

Ser Cys Ser Ala Ser Thr Phe Gln Ser Ser Glu Asp Ser Ala Val Val
            20                  25                  30

Lys Trp Leu Arg Phe Ile Phe Leu Ser Pro Cys Pro Gln Arg Thr Leu
        35                  40                  45

Leu Ser Ser Ile Asp Val Leu Leu Leu Thr Phe Ile Val Phe Ala
    50                  55                  60

Val Gln Lys Leu Tyr Ser Lys Leu Arg Ser Asn Glu His Ser Thr Ser
65                  70                  75                  80

Ser Ile Asp Lys Pro Leu Ile Ala His Asn Arg Thr Ser Ser Pro Trp
                85                  90                  95

Lys Val Ile Asp Gly Leu Tyr Trp Leu Phe Gln Ala Ile Thr His Val
            100                 105                 110

Val Ile Thr Ile Leu Ile Val His Glu Lys Arg Phe His Ala Ile Ser
        115                 120                 125

His Pro Leu Ser Leu Arg Val Phe Trp Ile Ala Asn Phe Val Val Met
    130                 135                 140

Ser Leu Phe Phe Gly Cys Gly Ile Thr Arg Leu Val Ser Leu Lys Glu
145                 150                 155                 160

Ile Asp Pro Asn Leu Arg Met Asp Asp Ile Ser Ser Leu Val Ser Phe
                165                 170                 175

Pro Ile Ser Val Val Leu Phe Ile Val Ala Ile Lys Gly Ser Thr Gly
            180                 185                 190
```

```
Val Ala Val Ile Ser Asp Ser Glu Ser His Leu Ser Asp Glu Thr Asn
        195                 200                 205

Gly Tyr Glu Leu Leu Asp Lys Ser Ser Val Ser Gly Phe Ala Ser Ala
    210                 215                 220

Ser Leu Ile Ser Lys Ala Phe Trp Ile Trp Met Asn Pro Leu Leu Gln
225                 230                 235                 240

Lys Gly Tyr Lys Ser Pro Leu Lys Ile Asp Glu Val Pro Ser Leu Ser
                245                 250                 255

Pro Leu His Arg Ala Glu Lys Met Ser Gln Leu Phe Glu Arg Asn Trp
                260                 265                 270

Pro Lys Pro Glu Glu Ile Ser Lys His Pro Val Arg Thr Thr Leu Leu
                275                 280                 285

Arg Cys Phe Trp Lys Glu Val Ile Phe Thr Ala Ile Leu Ala Val Ile
        290                 295                 300

Arg Val Cys Val Met Tyr Val Gly Pro Thr Leu Ile Gln Arg Phe Val
305                 310                 315                 320

Asp Tyr Thr Ala Gly Lys Arg Thr Ser Pro Tyr Glu Gly Tyr Tyr Leu
                325                 330                 335

Ile Gly Thr Leu Leu Ile Ala Lys Phe Val Glu Val Leu Thr Ser His
                340                 345                 350

Gln Phe Asn Phe Asn Ser Gln Lys Leu Gly Met Leu Ile Arg Ala Thr
        355                 360                 365

Leu Leu Thr Ser Leu Tyr Lys Lys Gly Leu Arg Leu Ser Cys Ser Ala
370                 375                 380

Arg Gln Ala His Gly Val Gly Gln Ile Val Asn Tyr Met Ala Val Asp
385                 390                 395                 400

Ala Gln Gln Leu Ser Asp Met Met Leu Gln Leu His Ser Ile Trp Leu
                405                 410                 415

Met Pro Leu Gln Val Ser Val Ala Leu Gly Ile Leu Tyr Thr Tyr Leu
                420                 425                 430

Gly Ala Ser Thr Val Val Thr Leu Ala Gly Leu Ala Ala Val Met Val
        435                 440                 445

Phe Val Val Phe Gly Thr Lys Arg Asn Asn Arg Phe Gln Phe Asn Ile
    450                 455                 460

Met Lys Asn Arg Asp Ser Arg Met Lys Ala Thr Asn Glu Met Leu Asn
465                 470                 475                 480

Tyr Met Arg Val Ile Lys Phe Gln Ala Trp Glu Glu His Phe Asn Lys
                485                 490                 495

Arg Ile Glu Ser Phe Arg Glu Ser Glu Tyr Gly Trp Leu Ser Lys Phe
                500                 505                 510

Leu Tyr Ser Ile Ala Gly Asn Ile Ile Val Leu Trp Ser Thr Pro Leu
                515                 520                 525

Leu Val Ala Thr Leu Thr Phe Gly Ser Ala Ile Leu Leu Gly Ile Pro
530                 535                 540

Leu Gly Ala Gly Thr Val Phe Thr Ala Thr Ser Leu Phe Lys Met Leu
545                 550                 555                 560

Gln Glu Pro Ile Arg Ala Phe Pro Gln Ser Met Ile Ser Leu Ser Gln
                565                 570                 575

Ala Met Ile Ser Leu Asp Arg Leu Asp Lys Tyr Met Met Ser Lys Glu
                580                 585                 590

Leu Val Asp Lys Ala Val Glu Arg Leu Glu Gly Cys Gly Gly Thr Ile
                595                 600                 605
```

```
Ala Met Gln Val Lys Asp Gly Ala Phe Cys Trp Asp Glu Asn Ser
610                 615                 620

Lys Glu Glu Leu Lys Asn Val Asn Phe Glu Ile Arg Lys Gly Glu Leu
625                 630                 635                 640

Ala Ala Val Val Gly Thr Val Gly Ala Gly Lys Ser Ser Leu Leu Ala
                645                 650                 655

Ser Val Leu Gly Glu Met His Lys Leu Ser Gly Gln Val Thr Ile Cys
            660                 665                 670

Gly Ser Thr Ala Tyr Val Ala Gln Thr Ser Trp Ile Gln Asn Gly Thr
        675                 680                 685

Ile Gln Glu Asn Ile Leu Phe Gly Met Pro Met Asn Arg Asp Arg Tyr
690                 695                 700

Lys Glu Val Ile Arg Val Cys Cys Leu Glu Lys Asp Leu Glu Ile Met
705                 710                 715                 720

Glu Phe Gly Asp Gln Thr Glu Ile Gly Glu Arg Gly Ile Asn Leu Ser
                725                 730                 735

Gly Gly Gln Lys Gln Arg Ile Gln Leu Ala Arg Ala Val Tyr Gln Asp
            740                 745                 750

Cys Asp Ile Tyr Leu Leu Asp Asp Val Phe Ser Ala Val Asp Ala His
        755                 760                 765

Thr Gly Ser Glu Ile Phe Lys Glu Cys Val Arg Gly Ile Leu Lys Asp
    770                 775                 780

Lys Thr Ile Leu Leu Val Thr His Gln Val Asp Phe Leu His Asn Val
785                 790                 795                 800

Asp Leu Ile Leu Val Met Arg Asp Gly Met Ile Val Gln Ser Gly Lys
                805                 810                 815

Tyr Asn Glu Ile Leu Glu Ala Gly Met Asp Phe Lys Glu Leu Val Ala
            820                 825                 830

Ala His Glu Thr Ser Leu Glu Leu Val Asp Val Glu Thr Thr Lys Glu
        835                 840                 845

Ser Asn Ala Ser Leu Glu Glu Ser Lys Ser Ser Arg Arg Leu Ser Lys
    850                 855                 860

Glu Glu Asn Gly Asp Asp Lys Ser Gln Gln Ser Thr Ser Asp Arg Gly
865                 870                 875                 880

Asp Ser Lys Leu Ile Lys Glu Glu Arg Glu Thr Gly Lys Val Ser
                885                 890                 895

Pro Arg Val Tyr Lys Leu Tyr Ile Thr Glu Ala Phe Gly Trp Trp Gly
            900                 905                 910

Val Val Leu Val Ile Leu Phe Ser Phe Leu Trp Gln Ser Ser Leu Met
        915                 920                 925

Ala Ser Asp Tyr Trp Leu Ala Tyr Glu Thr Ser Ala Asp Arg Ala Met
    930                 935                 940

Ser Phe Asn Pro Ser Leu Phe Ile Gly Ile Tyr Gly Val Ile Ala Val
945                 950                 955                 960

Val Ser Ser Leu Leu Ile Val Ile Arg Met Tyr Phe Val Thr Leu Met
                965                 970                 975

Gly Leu Lys Thr Ala Gln Ile Phe Phe Gly Gln Ile Leu Tyr Ser Ile
            980                 985                 990

Leu His Ala Pro Met Ser Phe Asp Thr Thr Pro Ser Gly Arg Ile
        995                 1000                1005

Leu Ser Arg Ala Ser Asn Asp Gln Thr Asn Ile Asp Val Phe Leu
        1010                1015                1020

Pro Phe Phe Met Asn Leu Thr Leu Ala Met Phe Ile Thr Leu Leu
```

```
              1025                1030                1035
Gly Ile Ile Ile Ile Thr Cys Gln Tyr Ser Trp Pro Thr Val Leu
              1040                1045                1050
Leu Leu Ile Pro Leu Gly Trp Leu Asn Ile Trp Tyr Arg Gly Tyr
              1055                1060                1065
Tyr Leu Ala Thr Ser Arg Glu Leu Thr Arg Leu Asp Ser Ile Thr
              1070                1075                1080
Lys Ala Pro Val Ile His His Phe Ser Glu Ser Ile Ser Gly Val
              1085                1090                1095
Met Thr Ile Arg Cys Phe Arg Lys Gln Glu Met Phe Cys Asn Glu
              1100                1105                1110
Asn Val Asn Arg Val Asn Ser Asn Leu Arg Met Asp Phe His Asn
              1115                1120                1125
Asn Gly Ser Asn Glu Trp Leu Gly Phe Arg Leu Glu Leu Met Gly
              1130                1135                1140
Ser Leu Leu Leu Cys Val Ser Ala Met Phe Met Ile Val Leu Pro
              1145                1150                1155
Ser Ser Ile Ile Lys Pro Glu Asn Val Gly Leu Ser Leu Ser Tyr
              1160                1165                1170
Gly Leu Ser Leu Asn Ser Val Leu Phe Trp Ser Ile Phe Val Ser
              1175                1180                1185
Cys Phe Val Glu Asn Lys Met Val Ser Val Glu Arg Leu Lys Gln
              1190                1195                1200
Phe Ser Glu Ile Pro Ser Glu Ala Glu Trp Arg Lys Met Asp Phe
              1205                1210                1215
Leu Pro Pro Ser Ser Trp Pro Ser Arg Gly Asn Val Glu Leu Glu
              1220                1225                1230
Asn Val Gln Val Arg Tyr Arg Pro Asn Thr Pro Leu Val Leu Lys
              1235                1240                1245
Gly Val Thr Leu Ser Ile Arg Gly Gly Glu Lys Ile Gly Val Val
              1250                1255                1260
Gly Arg Thr Gly Gly Gly Lys Ser Thr Leu Ile Gln Val Phe Phe
              1265                1270                1275
Arg Leu Val Glu Pro Ala Ala Gly Arg Ile Ile Ile Asp Asp Val
              1280                1285                1290
Asp Ile Ser Arg Leu Gly Leu His Asp Leu Arg Ser Arg Phe Gly
              1295                1300                1305
Ile Ile Pro Gln Glu Pro Val Leu Phe Glu Gly Thr Val Arg Ser
              1310                1315                1320
Asn Ile Asp Pro Ile Gly Gln Tyr Ser Asp Asp Glu Ile Trp Lys
              1325                1330                1335
Glu Pro Arg Thr Leu Pro Thr Gln Arg Cys Gly Val Phe Lys Thr
              1340                1345                1350
Arg Lys Thr Phe Thr Ser Cys Arg Arg Leu Glu Cys Arg Thr Glu
              1355                1360                1365
Ala Ala Ser Leu Leu Gly Lys Ser Asp Ala Lys Thr Gln Thr Ser
              1370                1375                1380
Ile Tyr Gly Gly Asn Cys Leu Cys Phe Thr Asp Arg Cys Ser Asp
              1385                1390                1395
Ser Glu Asn His Pro Arg Gly Leu Cys Gly Leu Tyr Tyr Asn Gln
              1400                1405                1410
His Cys Pro Gln Asn Thr Asn Ser His Gly Leu Ser Ser Cys Tyr
              1415                1420                1425
```

-continued

Arg Cys Arg Cys Phe Leu Ser Phe Tyr Phe Val Pro Tyr Phe Glu
1430                1435                1440

Ser Gly Lys Leu Phe Ile Cys Met Trp Phe Pro Thr Asn His Ser
1445                1450                1455

Gln Tyr Leu Tyr Glu Glu Ile Ala Cys Pro Ser Ser Ser Lys Cys
1460                1465                1470

Met

<210> SEQ ID NO 25
<211> LENGTH: 1404
<212> TYPE: PRT
<213> ORGANISM: Nicotiana tabacum

<400> SEQUENCE: 25

Trp Ile Gly Thr Val Cys Leu Gln Asn Leu Val His Phe Leu Val
1               5                   10                  15

Leu Pro Pro His Phe Asn Arg Gln Arg Ile Gln Gln Leu Leu Asn Gly
                20                  25                  30

Asp Ser Phe Ser Ser Leu His Val His Lys Gly Leu Phe Tyr Leu Pro
            35                  40                  45

Leu Met Cys Cys Phe Cys Leu Leu Ser Leu Tyr Leu Gln Tyr Lys Ser
        50                  55                  60

Cys Thr Gln Ser Gly Pro Met Ser Thr Leu Leu Ala Leu Ile Ser
65                  70                  75                  80

Leu Leu His Thr Thr Gly Leu Leu Arg Leu Gly Lys Ser Met Asp Cys
                85                  90                  95

Ile Gly Cys Phe Arg Arg Leu His Met Leu Ser Leu Tyr Phe Met Arg
            100                 105                 110

Lys Asp Phe Thr Leu Phe Pro Ile His Cys Pro Cys Ala Cys Phe Gly
        115                 120                 125

Leu Gln Thr Leu Leu Val Cys Ser Leu Val Val Gly Ser Gln Gly Leu
    130                 135                 140

Cys His Leu Arg Lys Leu Ile Leu Ile Glu Trp Met Ile Val His Phe
145                 150                 155                 160

His Phe Leu Phe Leu Leu Phe Ser Ser Leu Leu Pro Leu Lys Val Arg
                165                 170                 175

Pro Glu Leu Leu Leu Val Ile Leu Asn Leu Thr Val Met Lys Pro Met
            180                 185                 190

Val Met Asn Ser Trp Ile Asn Pro Val Val Ala Leu Leu Gln Leu Leu
        195                 200                 205

Tyr Arg Lys Pro Phe Gly Phe Gly Thr Leu Tyr Cys Lys Lys Val Thr
    210                 215                 220

Ser His Leu Ser Arg Leu Met Lys Phe Leu His Phe Pro His Cys Ile
225                 230                 235                 240

Glu Gln Arg Lys Cys Leu Asn Phe Ser Lys Glu Ile Gly Leu Asn Leu
                245                 250                 255

Lys Lys Tyr Gln Ser Ile Leu Ser Glu Gln His Cys Cys Val Ala Phe
            260                 265                 270

Gly Arg Lys Leu Phe Leu Leu Pro Phe Leu Gln Leu Gly Tyr Val Leu
        275                 280                 285

Cys Met Gly Gln His Ser Tyr Lys Asp Leu Leu Ile Thr Gln Gln Glu
    290                 295                 300

Arg Gly His Leu Leu Met Lys Asp Thr Thr Leu Glu Leu Ser Pro Asn
305                 310                 315                 320

```
Leu Trp Lys Phe Pro Leu Ile Ser Ser Thr Leu Thr Pro Lys Ser Leu
            325                 330                 335

Ala Cys Leu Phe Glu Arg His Phe Ser Leu Leu Cys Ile Arg Arg Gly
            340                 345                 350

Gly Cys His Ala Gln Leu Asp Arg Leu Met Val Leu Asp Arg Leu Ile
            355                 360                 365

Ile Trp Pro Ser Met Leu Ser Ser Cys Pro Ile Cys Tyr Ser Tyr Ile
            370                 375                 380

Pro Phe Gly Ser Cys His Cys Lys Phe Leu Trp Leu Ala Ser Phe Ile
385                 390                 395                 400

Leu Thr Ser Val Leu Gln Leu Leu Arg Leu Asp Leu Gln Gln Trp Tyr
            405                 410                 415

Leu Trp Cys Leu Glu Leu Lys Glu Thr Thr Gly Phe Asn Leu Thr Ser
            420                 425                 430

Arg Ile Val Ile Leu Glu Lys Arg Gln Met Arg Cys Leu Ile Ile Cys
            435                 440                 445

Ala Leu Ser Ser Arg His Gly Lys Asn Ile Leu Thr Lys Glu Leu Asn
            450                 455                 460

Pro Ser Ala Asn Pro Ser Met Asp Gly Cys Pro Ser Ser Cys Thr Gln
465                 470                 475                 480

Ser Leu Gly Ile Ser Leu Ser Cys Gly Ala Leu Leu Phe Trp Leu His
            485                 490                 495

Ser Leu Leu Glu Val Gln Ser Cys Trp Glu Ser Arg Leu Val Gln Gly
            500                 505                 510

Gln Cys Ser Leu Gln His Leu Ser Arg Cys Cys Arg Asn Arg Ser
            515                 520                 525

Gly Leu Ser Leu Asn Pro Ser His Phe His Lys Gln Tyr Leu Leu Ile
            530                 535                 540

Asp Trp Thr Asn Ile Val Arg Ser Trp Ile Lys Leu Trp Lys Asp Lys
545                 550                 555                 560

Val Val Gly Val Gln Leu Leu Cys Arg Lys Met Glu Leu Phe Ala Gly
            565                 570                 575

Met Met Lys Thr Val Lys Lys Asn Lys Met Thr Leu Arg Leu Glu Lys
            580                 585                 590

Glu Ser Leu Gln Gln Trp Gly Gln Leu Gly Arg Gly Ser Leu Pro Ser
            595                 600                 605

Leu His Leu Tyr Leu Val Arg Cys Thr Ser Cys Arg Val Arg Ser Gln
            610                 615                 620

Phe Val Val Gln Leu Pro Met Leu His Lys His Arg Gly Phe Arg Met
625                 630                 635                 640

Ala Arg Tyr Lys Lys Ile Ser Cys Leu Val Cys Gln Thr Glu Thr Asp
            645                 650                 655

Thr Arg Lys Ser Gly Phe Ala Ala Trp Arg Arg Thr Trp Lys Trp Ser
            660                 665                 670

Leu Glu Thr Arg Leu Lys Glu Asn Val Ala Ser Thr Ser Val Val Val
            675                 680                 685

Arg Ser Ser Glu Ser Ser Leu Gln Glu Leu Phe Thr Arg Thr Val Ile
            690                 695                 700

Phe Ile Phe Met Met Tyr Ser Val Gln Leu Met Leu Thr Leu Ala Leu
705                 710                 715                 720

Lys Ser Ser Arg Asn Val Gly Glu Phe Leu Lys Ile Lys Pro Phe Cys
            725                 730                 735
```

```
Leu Ser His Thr Lys Leu Thr Ser Cys Ile Met Leu Thr Ser Leu Ser
            740                 745                 750

Cys Glu Met Gly Ser Cys Asn Leu Ala Asn Ile Met Arg Tyr Lys Leu
            755                 760                 765

Glu Trp Ile Leu Lys Ser Leu His Met Arg Pro Leu Asn Leu Leu Thr
770                 775                 780

Trp Lys Gln Pro Lys Arg Ala Met Pro Leu Lys Asn Gln Asn Leu
785                 790                 795                 800

Leu Glu Asp Tyr Leu Arg Lys Lys Thr Glu Met Ile Asn Leu Asn Ser
                805                 810                 815

Leu His Leu Ile Gly Gly Ile Leu Asn Leu Arg Lys Lys Lys Glu Lys
            820                 825                 830

Leu Glu Lys Ser Val Leu Val Cys Thr Ser Tyr Ile Leu Leu Lys Leu
            835                 840                 845

Leu Asp Gly Gly Val Cys Leu Ser Cys Phe Arg Ser Cys Gly Lys Val
            850                 855                 860

Leu Trp Gln Val Ile Ile Gly Trp His Met Lys Leu Gln Arg Ile Val
865                 870                 875                 880

Pro Cys Pro Ser Ile Leu Leu Cys Leu Leu Gly Tyr Thr Val Leu Leu
                885                 890                 895

Gln Leu Phe Leu Arg Cys Ser Gly Cys Ile Leu His Leu Trp Gly Ser
                900                 905                 910

Arg Leu Pro Lys Tyr Phe Ser Asp Arg Phe Phe Thr Ala Tyr Cys Met
                915                 920                 925

Leu Leu Cys His Phe Leu Thr Gln His Leu Pro Glu Glu Phe Val Gly
            930                 935                 940

His Leu Met Ile Arg Pro Thr Leu Met Ser Ser Ser Arg Phe Leu Ile
945                 950                 955                 960

Ser Leu Trp Pro Cys Leu Ser His Cys Ser Ala Ser Ser Ser Ser His
                965                 970                 975

Ala Asn Ile Leu Gly Leu Pro Tyr Tyr Phe Leu Trp Val Gly Leu
            980                 985                 990

Ile Ser Gly Thr Gly Asp Ile Ile Leu Gln His Leu Val Asn Leu Gly
            995                 1000                1005

Leu Thr Gln Leu Gln Lys His Leu Leu Phe Ile Ile Ser Leu Lys
    1010                1015                1020

Ala Ser Gln Val Leu Leu Tyr Val Ala Leu Gly Ser Arg Arg Cys
    1025                1030                1035

Phe Val Thr Arg Met Thr Glu Ile Pro Ile Cys Glu Trp Ile Ser
    1040                1045                1050

Thr Thr Met Asp Pro Met Asn Gly Trp Ala Phe Asp Trp Asn Trp
    1055                1060                1065

Glu Ala Tyr Phe Phe Val Phe Leu Gln Cys Ser Leu Ser Tyr Leu
    1070                1075                1080

Ala Ala Ser Ser Ser Gln Lys Met Leu Val Cys His Tyr His Met
    1085                1090                1095

Ala Cys Leu Leu Ile Val Ser Tyr Ser Gly Pro Ser Leu Val Ala
    1100                1105                1110

Leu Trp Lys Ile Lys Trp Phe Leu Ser Lys Asp Asn Ser Ser Gln
    1115                1120                1125

Lys Tyr His Gln Lys Gln Ser Gly Glu Arg Trp Ile Phe Ser His
    1130                1135                1140

Leu Gln Val Gly Gln Ala Val Gly Met Leu Ser Leu Lys Thr Cys
```

-continued

```
            1145                1150                1155

Arg Leu Asp Ile Val Arg Thr Leu Leu Cys Leu Lys Glu Leu Leu
        1160                1165                1170

Ser Ala Leu Glu Gly Glu Arg Arg Val Leu Leu Val Val Gln Gly
        1175                1180                1185

Val Glu Asn Gln His Phe Lys Phe Ser Phe Val Trp Trp Ser Leu
        1190                1195                1200

Gln Leu Glu Glu Ser Leu Met Thr Ile Tyr Pro Asp Leu Gly Phe
        1205                1210                1215

Met Ile Leu Asp Leu Ala Ser Gly Ser Phe Pro Lys Ser Gln Ser
        1220                1225                1230

Phe Leu Lys Glu Leu Glu Ala Thr Leu Thr Pro Leu Asp Asn Ile
        1235                1240                1245

Gln Met Met Lys Phe Gly Arg Ser Leu Glu Arg Cys Gln Leu Lys
        1250                1255                1260

Asp Val Val Ser Leu Lys Pro Glu Lys Leu Asp Ser Pro Val Val
        1265                1270                1275

Asp Asn Gly Asp Asn Trp Ser Val Gly Gln Arg Gln Leu Leu Cys
        1280                1285                1290

Leu Gly Arg Val Met Leu Lys Arg Ser Arg Leu Leu Phe Met Asp
        1295                1300                1305

Glu Ala Thr Ala Ser Val Asp Ser Gln Thr Asp Ala Val Ile Gln
        1310                1315                1320

Lys Ile Ile Arg Glu Asp Phe Ala Ala Cys Thr Ile Ile Ser Ile
        1325                1330                1335

Ala His Arg Ile Pro Thr Val Met Asp Cys Asp Arg Val Leu Val
        1340                1345                1350

Ile Asp Ala Gly Ala Asp Phe Ser Pro Phe Thr Leu Tyr Leu Ile
        1355                1360                1365

Leu Asn Leu Val Asn Asp Tyr Leu Ser Val Cys Asp Gly Phe Gln
        1370                1375                1380

Pro Ile Ile Val Ser Thr Phe Met Lys Lys Leu Pro Asn Val Ser
        1385                1390                1395

Gln Val Val Val Asn Ala
        1400
```

<210> SEQ ID NO 26
<211> LENGTH: 1373
<212> TYPE: PRT
<213> ORGANISM: Nicotiana tabacum

<400> SEQUENCE: 26

```
Gly Tyr Glu Glu Gln Tyr Val Phe Arg Ile Leu Phe Ser Ile Thr Phe
1               5                   10                  15

Leu Phe Cys Leu His Ile Ser Ile Val Arg Gly Phe Ser Ser Cys Met
            20                  25                  30

Val Lys Ile His Phe Pro Leu Ser Met Ser Thr Lys Asp Ser Ser Ile
        35                  40                  45

Phe His Cys Ala Ala Phe Ala Tyr Phe His Cys Ile Cys Ser Thr Lys
    50                  55                  60

Val Val Leu Lys Val Glu Val Gln Ala Leu Tyr Phe His Ala Ser Asn
65                  70                  75                  80

Cys Thr Gln Gln Asp Phe Phe Ala Leu Glu Ser His Arg Trp Thr Val
            85                  90                  95
```

-continued

```
Leu Val Val Ser Gly Asp Tyr Thr Cys Cys Asn His Tyr Thr Asn Ser
            100                 105                 110

Ser Glu Lys Ile Ser Arg Tyr Phe Pro Ser Thr Val Pro Ala Arg Val
        115                 120                 125

Leu Asp Cys Lys Leu Cys Ser Tyr Glu Phe Val Leu Trp Leu Trp Asp
    130                 135                 140

His Lys Ala Cys Val Thr Gly Asn Ser Phe Lys Asn Gly Tyr Lys Phe
145                 150                 155                 160

Ile Ser Phe Ile Ser Tyr Phe Cys Cys Ser Leu His Cys His Arg
            165                 170                 175

Phe Asp Arg Ser Cys Cys Asn Phe Ile Ser Leu Lys Asn Gln Trp Leu
        180                 185                 190

Thr Pro Gly Ile Gln Cys Glu Trp Leu Cys Phe Ser Phe Ser Asn Ile
    195                 200                 205

Glu Ser Leu Leu Asp Leu Asp Glu Pro Phe Thr Ala Lys Arg Leu Gln
    210                 215                 220

Val Thr Ser Gln Asp Ser Ser Phe Thr Phe Pro Thr Ala Ser Arg Glu
225                 230                 235                 240

Asn Val Ser Thr Phe Arg Lys Lys Leu Ala Thr Arg Asn Ile Lys Ala
            245                 250                 255

Ser Cys Pro Asn Asn Ile Ala Ala Leu Leu Leu Glu Gly Ser Tyr Phe
        260                 265                 270

Tyr Cys His Ser Cys Ser Asn Gly Met Cys Tyr Val Cys Arg Ala Asn
    275                 280                 285

Thr His Thr Lys Ile Cys Leu His Ser Arg Lys Glu Asp Ile Ser Leu
    290                 295                 300

Arg Ile Leu Pro Tyr Arg Asn Ser Pro Asn Ser Gln Ile Cys Gly Ser
305                 310                 315                 320

Ser Asn Leu Ser Ser Val Gln Leu Leu Pro Lys Ala Trp His Ala Tyr
            325                 330                 335

Ser Ser Asp Thr Ser His Phe Phe Val Glu Gly Val Lys Val Val Met
        340                 345                 350

Leu Ser Thr Gly Ser Trp Cys Trp Thr Asp Cys Lys Leu Tyr Gly Arg
    355                 360                 365

Arg Cys Ser Ala Ala Val Arg Tyr Asp Ala Thr Ala Thr Phe His Leu
370                 375                 380

Ala His Ala Ile Ala Ser Phe Cys Gly Phe Arg His Pro Leu Tyr Leu
385                 390                 395                 400

Pro Arg Cys Phe Asn Cys Cys Asn Ala Ser Trp Thr Cys Ser Ser Asp
            405                 410                 415

Gly Ile Cys Gly Val Trp Asn Lys Lys Gln Val Ser Ile His His
        420                 425                 430

Glu Glu Ser Phe Asn Glu Ser Asp Lys Asp Ala Leu Tyr Ala Arg Tyr
    435                 440                 445

Lys Val Pro Gly Met Gly Arg Thr Phe Gln Lys Asn Ile Leu Pro Arg
    450                 455                 460

Ile Arg Val Trp Met Val Val Gln Val Leu Val Leu Asn Arg Trp Glu
465                 470                 475                 480

Tyr His Cys Leu Val Glu His Ser Ser Ser Gly Tyr Thr His Phe
            485                 490                 495

Trp Lys Cys Asn Leu Val Gly Asn Pro Ala Trp Cys Arg Asp Ser Val
        500                 505                 510

His Cys Asn Ile Ser Leu Gln Asp Val Ala Gly Thr Asp Gln Gly Phe
```

```
              515                 520                 525
Pro Ser Ile His Asp Leu Thr Phe Thr Ser Asn Asp Ile Ser Ile Gly
            530                 535                 540

Gln Ile Tyr Asp Glu Gly Val Ser Gly Ser Cys Gly Lys Thr Arg Arg
545                 550                 555                 560

Leu Trp Gly Tyr Asn Cys Tyr Ala Gly Glu Arg Trp Ser Phe Leu Leu
                565                 570                 575

Gly Lys Gln Arg Arg Ile Glu Lys Cys Lys Leu Asp Lys Arg Arg Ala
            580                 585                 590

Cys Ser Ser Gly Asp Ser Trp Gly Gly Glu Val Phe Pro Pro Cys
                595                 600                 605

Ile Cys Thr Trp Asp Ala Gln Val Val Gly Ser Gly His Asn Leu Trp
            610                 615                 620

Phe Asn Cys Leu Cys Cys Thr Asn Ile Val Asp Ser Glu Trp His Asp
625                 630                 635                 640

Thr Arg Lys Tyr Pro Val Trp Tyr Ala Asn Glu Gln Arg Gln Ile Gln
                645                 650                 655

Gly Ser Asp Pro Gly Leu Leu Leu Gly Glu Gly Leu Gly Asn Asn Gly
                660                 665                 670

Val Trp Arg Pro Asp Asn Arg Arg Thr Trp His Gln Pro Gln Trp Trp
            675                 680                 685

Ser Glu Ala Ala Asn Pro Ala Cys Lys Ser Cys Leu Pro Gly Leu Tyr
            690                 695                 700

Leu Ser Ser Arg Cys Ile Gln Cys Ser Cys Ser His Trp Leu Asn Leu
705                 710                 715                 720

Gln Gly Met Cys Glu Gly Asn Ser Arg Asn His Phe Ala Cys His Thr
                725                 730                 735

Pro Ser Leu Leu Ala Cys Pro Asp Pro Cys His Ala Arg Trp Asp Asp
                740                 745                 750

Arg Ala Ile Trp Gln Ile Asp Ile Arg Ser Trp Asn Gly Phe Arg Ala
            755                 760                 765

Ser Ser Cys Thr Asp Leu Phe Arg Thr Cys Arg Gly Asn Asn Gln Arg
            770                 775                 780

Glu Gln Cys Leu Pro Arg Ile Lys Ile Phe Ser Lys Ile Ile Gly Arg
785                 790                 795                 800

Lys Arg Arg Ile Ser Thr Val Tyr Ile Gly Gly Phe Thr Tyr Lys Gly
                805                 810                 815

Arg Arg Lys Arg Asn Trp Lys Ser Gln Ser Ser Cys Val Gln Ala Ile
                820                 825                 830

Tyr Tyr Ser Phe Trp Met Val Gly Cys Ser Ala Ser Tyr Leu Val Phe
            835                 840                 845

Val Leu Val Ala Lys Phe Ser Asn Gly Lys Leu Leu Ala Gly Ile Asn
            850                 855                 860

Phe Ser Gly Ser Cys His Val Leu Gln Ser Phe Ser Val Tyr Trp Asp
865                 870                 875                 880

Ile Arg Cys Tyr Cys Ser Cys Phe Phe Val Ala Asp Ser Asp Gln Asp
                885                 890                 895

Val Phe Cys Asp Thr Tyr Gly Ala Gln Asp Cys Pro Asn Ile Phe Arg
            900                 905                 910

Thr Asp Ser Leu Gln His Thr Ala Cys Ser Tyr Val Ile Phe His Asn
            915                 920                 925

Thr Phe Arg Lys Asn Ser Glu Ser Gly Ile Ser Asp Gln His Cys Leu
            930                 935                 940
```

-continued

Pro Pro Val Phe Tyr Glu Ser His Phe Gly His Val Tyr His Thr Ala
945                 950                 955                 960

Arg His His His His Met Pro Ile Phe Leu Ala Tyr Arg Thr Thr
            965                 970                 975

Phe Asp Ser Ser Gly Leu Ala Tyr Leu Val Pro Gly Ile Leu Ser Cys
            980                 985                 990

Asn Ile Ser Ile Asp Ser Ala Leu Asn Tyr Lys Ser Thr Cys Tyr Ser
        995                 1000                1005

Ser Phe Leu Lys His Leu Arg Cys Tyr Asp Tyr Thr Leu Leu Glu
    1010                1015                1020

Ala Gly Asp Val Leu Arg Glu Cys Lys Pro Ser Glu Phe Gln Ser
    1025                1030                1035

Ala Asn Gly Phe Pro Gln Gln Trp Ile Gln Met Val Gly Leu Ser
    1040                1045                1050

Thr Gly Ile Asp Gly Lys Leu Thr Ser Leu Cys Phe Cys Asn Val
    1055                1060                1065

His Asp Cys Leu Thr Gln His Gln Ala Arg Lys Cys Trp Phe
    1070                1075                1080

Val Thr Ile Ile Trp Leu Val Ser Cys Pro Ile Leu Val His Leu
    1085                1090                1095

Cys Glu Leu Leu Cys Gly Lys Asn Gly Phe Cys Arg Lys Ile Lys
    1100                1105                1110

Thr Val Leu Arg Asn Thr Ile Arg Ser Arg Val Glu Lys Asp Gly
    1115                1120                1125

Phe Ser Pro Thr Phe Lys Leu Ala Lys Pro Trp Glu Cys Ala Lys
    1130                1135                1140

Arg Ala Gly Ile Ser Ser Glu His Ser Ser Ser Ala Arg Ser Tyr
    1145                1150                1155

Ser Gln His Arg Gly Arg Glu Asp Arg Cys Cys Trp Ser Tyr Arg
    1160                1165                1170

Gly Trp Lys Ile Asn Ile Asn Ser Ser Phe Leu Ser Phe Gly Gly
    1175                1180                1185

Ala Cys Ser Trp Lys Asn Asn His Arg Arg Tyr Ile Gln Thr Trp
    1190                1195                1200

Ala Ser Ser Ile Ser Leu Arg Asp His Ser Pro Arg Ala Ser Pro
    1205                1210                1215

Phe Arg Asn Cys Glu Lys Gln His Pro His Trp Thr Ile Phe Arg
    1220                1225                1230

Asn Leu Glu Gly Ala Ser Asn Ala Ala Asn Ser Lys Met Trp Cys
    1235                1240                1245

Leu Asn Pro Lys Asn Leu Ile His Gln Leu Leu Ile Thr Glu Ile
    1250                1255                1260

Thr Gly Val Ser Asp Arg Gly Ser Phe Phe Ala Trp Glu Glu Cys
    1265                1270                1275

Asn Val Ala Asp Phe Tyr Leu Trp Met Arg Gln Leu Pro Leu Leu
    1280                1285                1290

Ile His Arg Gln Met Gln Phe Arg Lys Ser Ser Ala Arg Thr Leu
    1295                1300                1305

Arg Pro Val Leu Ser Ala Leu Pro Thr Glu Tyr Gln Gln Ser Trp
    1310                1315                1320

Thr Val Ile Glu Phe Leu Leu Met Gln Val Leu Ile Ser Leu Leu
    1325                1330                1335

| Leu | Leu | Cys | Thr | Leu | Phe | Ile | Trp | Met | Ile | Ile | Tyr | Leu | Tyr | Val |
|---|---|---|---|---|---|---|---|---|---|---|---|---|---|---|
| 1340 | | | | | 1345 | | | | | 1350 | | | | |

| Met | Val | Ser | Asn | Gln | Ser | Ser | Val | Pro | Leu | Arg | Asn | Cys | Leu | Met |
|---|---|---|---|---|---|---|---|---|---|---|---|---|---|---|
| 1355 | | | | | 1360 | | | | | 1365 | | | | |

| Leu | Ala | Lys | Met | His |
|---|---|---|---|---|
| 1370 | | | | |

<210> SEQ ID NO 27
<211> LENGTH: 4521
<212> TYPE: DNA
<213> ORGANISM: Nicotiana tabacum

<400> SEQUENCE: 27

| | |
|---|---|
| atggatatga ggaacagtat gtcttcagaa tcttgtttag catcactttc ttgttctgcc | 60 |
| tccacatttc aatcgtcaga ggattcagca gttgttaaat ggttaagatt cattttcctc | 120 |
| tctccatgtc cacaaaggac tcttctatct tccattgatg tgctgctttt gcttactttc | 180 |
| attgtatttg cagtacaaaa gttgtactca aagttgaggt ccaatgagca ctctacttct | 240 |
| agcattgata agcctctaat tgcacacaac aggacttctg ttagaaccaa tctttggttt | 300 |
| aagctgtctc tgattttgtc agctatttta gccttatctt ctatagtttt atgcattttg | 360 |
| gttattgtgg gaaattccca gtcgccttgg aaagtcatag atggactgta ttggttgttt | 420 |
| caggcgatta cacatgttgt aatcactata ctaatagttc atgagaaaag atttcacgct | 480 |
| atttcccatc cactgtccct gcgcgtgttt tggattgcaa actttgtagt tatgagtttg | 540 |
| ttctttggtt gtgggatcac aaggcttgtg tcacttaagg aaattgatcc taatttaaga | 600 |
| atggatgata taagttcatt agtttcattt cctatttctg ttgttctctt cattgttgcc | 660 |
| attaaaggtt cgaccggagt tgctgtaatt agtgattctg aatctcactt aagtgatgaa | 720 |
| accaatggtt atgaactcct ggataaatcc agtgtgagtg gctttgcttc agcttctcta | 780 |
| atatcgaaag cctttggat ttggatgaac cctttactgc aaaaaggtta caagtcacct | 840 |
| ctcaagattg atgaagttcc ttcactttcc ccactgcata gagcagagaa aatgtctcaa | 900 |
| cttttcgaaa gaaattggcc taaacctgaa gaaatatcaa agcatcctgt ccgaacaaca | 960 |
| tgctgcgtt gcttttggaa ggaagttatt tttactgcca ttcttgcagt aattaggta | 1020 |
| tgtgttatgt atgtagggcc aacactcata caaagatttg ttgattacac agcaggaaag | 1080 |
| aggacatctc cttatgaagg atactacctt ataggaactc tcctaatagc caaatttgtg | 1140 |
| gaagttctaa cctctcatca gttcaacttt aactcccaaa agcttggcat gcttattcga | 1200 |
| gcgacacttc tcacttcttt gtataagaag gggttaaggt tgtcatgctc agctagacag | 1260 |
| gctcatggtg ttggacagat tgtaaattat atggccgtcg atgctcagca gctgtccgat | 1320 |
| atgatgctac agctacattc catttggctc atgccattgc aagttctgt ggctttaggc | 1380 |
| atcctttata cttacctcgg tgcttcaact gttgtaacgc tagctggact tgcagcagtg | 1440 |
| atggtatttg tggtgtttgg aactaaaaga acaacaggtt tcaatttaa catcatgaag | 1500 |
| aatcgtgatt ctagaatgaa agcgacaaat gagatgctta attatatgcg cgttataaag | 1560 |
| ttccaggcat gggaagaaca ttttaacaaa agaattgaat ccttccgcga atccgagtat | 1620 |
| ggatggttgt ccaagttctt gtactcaatc gctgggaata tcattgtctt gtggagcact | 1680 |
| cctcttctag tggctacact cactttggga agtgcaatct tgtgggaat cccgcttggt | 1740 |
| gcagggacag tgttcactgc aacatctctc ttcaagatgt tgcaggaacc gatcagggct | 1800 |
| ttccctcaat ccatgatctc actttcacaa gcaatgatat ctcttgatag attggacaaa | 1860 |

```
tatatgatga gtaaggagtt agtggataaa gctgtggaaa gactagaagg ttgtgggggt      1920
acaattgcta tgcaggtgaa agatggagct ttttgctggg atgatgaaaa cagtaaagaa      1980
gaattgaaaa atgtaaactt tgagattaga aaaggagagc ttgcagcagt agtggggaca      2040
gttggggcgg ggaagtcttc cctccttgca tctgtacttg gtgagatgca caagttgtcg      2100
ggtcaggtca caatttgtgg ttcaactgcc tatgttgcac aaacatcgtg gattcagaat      2160
ggcacgatac aagaaaatat cctgtttggt atgccaatga acagagacag atacaaggaa      2220
gtgatccggg tttgctgctt ggagaaggac ttggaaataa tggagtttgg agaccagact      2280
gaaataggag aacgtggcat caacctcagt ggtggtcaga agcagcgaat ccagcttgca      2340
agagctgttt accaggactg tgatatttat cttctagatg atgtattcag tgcagttgat      2400
gctcacactg gctctgaaat cttcaaggaa tgtgtgaggg gaattcttaa agataaaacc      2460
attttgcttg tcacacacca agttgacttc ttgcataatg ttgacctgat ccttgtcatg      2520
cgagatggga tgatcgtgca atctggcaaa tataatgaga tattagaagc tggaatggat      2580
tttaaagagc tagtagctgc acatgagacc tctttagaac ttgttgacgt ggaaacaacc      2640
aaagagagca atgcctccct tgaagaatca aaatcttctc gaagattatc taaggaagaa      2700
aacggagatg ataaatctca acagtctaca tctgataggg gggattctaa acttataaag      2760
gaagaagaaa gagaaactgg aaaagtcagt cctcgtgtgt acaagctata tattactgaa      2820
gcttttggat ggtggggtgt agtgctagtt atcttgtttt cgttcttgtg gcaaagttct      2880
ctaatggcaa gtgattattg gctggcatat gaaacttcag cggatcgtgc catgtccttc      2940
aatccttctc tgtttattgg gatatacggt gttattgcag ttgtttcttc gttgctgata      3000
gtgatcagga tgtatttgt gacacttatg gggctcaaga ctgcccaaat attttttcgga     3060
cagattcttt acagcatact gcatgctcct atgtcatttt ttgacacaac ccttccggaa      3120
agaattctga gtcgggcatc taatgatcag accaacattg atgtcttcct cccgtttttt      3180
atgaatctca ctttggccat gtttatcaca ctgctcggca tcatcatcat cacatgccaa      3240
tattcttggc ctaccgtact acttttgatt cctctgggtt ggcttaatat ctggtaccgg      3300
ggatattatc ttgcaacatc tcgtgaattg actcggcttg actcaattac aaaagcaccct     3360
gttattcatc atttctctga aagcatctca ggtgttatga ctatacgttg ctttaggaag      3420
caggagatgt tttgtaacga gaatgtaaac cgagtgaatt ccaatctgcg aatggatttc      3480
cacaacaatg gatccaatga atggttgggc tttcgactgg aattgatggg aagcttactt      3540
ctttgtgttt ctgcaatgtt catgattgtc ttacctagca gcatcatcaa gccagaaaat      3600
gttggtttgt cactatcata tggcttgtct cttaatagtg tcctattctg gtccatcttt      3660
gtgagttgct ttgtgaaaaa taaaatggtt tctgtcgaaa gattaaaaca gttctcagaa      3720
ataccatcag aagcagagtg gagaaagatg gattttctcc caccttcaag ttggccaagc      3780
cgtgggaatg ttgagcttga aaacgtgcag gttagatatc gtccgaacac tcctctagtg      3840
cttaaaggag ttactctcag cattagaggg ggagagaaga taggtgttgt tggtcgtaca      3900
gggggtggaa aatcaacatt aattcaagtt ttctttcgtt tggtggagcc tgcagctgga      3960
agaataatca ttgatgacgt agatatatcc agacttgggc ttcatgatct tagatctcgc      4020
ttcgggatca ttccccaaga gccagtcctt tttgaaggaa ctgtgagaag caacattgac      4080
cccattggac aatattcaga tgatgaaatt tggaagagcc tcgaacgctg ccaactcaaa      4140
gatgtggtgt ctttaaaacc cgaaaaactt gattcaccag ttgttgataa cggagataac      4200
tggagtgtcg gacagaggca gcttctttgc ttgggaagag tgatgctaaa acgtagcaga      4260
```

```
cttctattta tggatgaggc aactgcctct gttgattcac agacagatgc agtgattcag   4320
aaaatcatcc gcgaggactt tgcggcctgt actataatca gcattgccca cagaatacca   4380
acagtcatgg actgtgatag agttcttgtt atagatgcag gaatagcaaa agagtttgac   4440
aaaccatctc gtttgcttga aaggccttca cttttgggg ctttggttca agaatatgcc    4500
aaccgatcct ctgagctcta a                                              4521

<210> SEQ ID NO 28
<211> LENGTH: 6190
<212> TYPE: DNA
<213> ORGANISM: Nicotiana tabacum

<400> SEQUENCE: 28
ccgtcaaccc agtcttggcc accacataaa cacagctttg acttgtctct cccttttccc     60
tattttcacc acccttttca atttcccacc ttatattcat tattatattt aatcaatcaa    120
atcaaagttg gaaaaaaagg gagtaataat caaatggagt agtatataca taccagaaca    180
atgaaagagc actcataagc taaagcccat aattcatcac gaaaccacaa tatagaggaa    240
acctgacgtg tcccttaaaa tctaaccttg aacctctgag acctccaaaa aaaacatcat    300
ggaaattgca aagggcatgt ctgtgtttca atctttgagg tatgttggcg ttgatgaatc    360
cctccgaaac cccattttct tacgtgtcat tagttgttct ttgcacctgg gattgttcct    420
tgtaattctt gggttgtgtt gttggaatac aatcaggagg acaataatg  ctggccacaa    480 acagagtagt actaggaatg ctaggttctt gtactacaaa tcaaccttgt tttgttcaat    540
aggtctagcc atctttagct ttgtgttatg tttgttagct cattttatt ggtatagaaa     600 tggttggtca gaagaaaaaa ttataaccct tttggatttt gcattaaagt tgctagcttg    660
gttgtcaatc tctgttttct tgcacaccca gttcctaat tcttgtgaaa ccaaataccc     720
tcttgtttta agagtttggt gggggctttt cttctttgtt tcttgttatt gccttgttat    780
agaccttgtt tatggggaaa agaaccaatc tttaccaact caattttgta tacctgatgt    840
tgttttcact cttatggggt tattcttctg ttttgttggg tttattgtta aaacagagag    900
tgaggagaat atgcttcagg aaccctctt aaatggtagt gttgccaatg gcatggactc     960
aaagaagtct actggggatc aaactgtcac cccttatgcc aatgctaaca tttttagtct   1020 cttactttc tcttggatgg gtcccctaat ttctgttggc aacaagaaac cattagacct    1080
tgaggatgtt cctcagcttc actttgatga tagtgtcaaa gggagttttc ctattttag   1140 agaaaaacta gaatcgtgtg gtgggggaaa tagtaaccgt gtgactacct tcatgctggt   1200
gaaggctttg gttttcacag cacggaagga gatagtgtta tcggctctct tcgtgcttct   1260
ttacgctctg gcgtcttttg ttggcccgta cctcattgat accttagttc agtatctgaa   1320
tggaaaacga gactttgata tgaaggtta tgtcttagtg gctgcattct tcgttgcaaa    1380
gttggtggag tgtttggcgc aaaggcattg gttttcaag gtgcagcagg agggtatcg     1440 ggcacgggca gcactggttt ccaaaatcta caacaagggt ttaaccctct cctgtcagtc   1500
aaagcaaagc cacactagtg gagagatcat caattttatg acagttgatg ccgagaggat   1560
tggtgacttc ggttggtata tgcatgatcc ttggatggta atcatacaag ttgctctggc   1620
attggtgata ctctataaaa atcttggcct agctgctatc gccgcgtttg ttgctacaat   1680
aatagtgatg ttggcaaaca tcccttagg gagtttgcag gagaagtttc aggagaaact   1740
catggaatcg aaagatagaa ggatgaaggc tacatctgaa gtcttaagga atatgagaat   1800
```

```
actcaagctt caagcttggg agatgaagtt tctgtctagg atcttggacc tcaggactac   1860
agaggcagga tggttgatga aatatgtgta cacatcagct atgactactt ttgtcttctg   1920
ggttgctcct acatttgttt ctgtgacgac cttttggcgct gcaatgctta tgggaatccc   1980
acttgaatct gggaagatat tgtctgcact tgcgacattt agaattcttc aagagcccat   2040
ctacaatctc ccagatacaa tttcaatgat tgctcaaacc aaagtttctc ttgatcgtat   2100
tgcatctttc ctttctcttg atgacttgca gcctgatgtc atagagaagc ttccaaaagg   2160
tagttctgat gaagcaattg agattgtagg tgggaacttc gcttgggatg catccacctc   2220
gactccactt ctaaaggatg taaatcttag agtgcttaat ggcatgagag ttgccatttg   2280
tggtacagtt ggttcaggaa atcaagcttc actgtctagc attttaggag agatgcccaa   2340
attatcaggg actattaaac ttagtggaac gaaggcttat gttgcacagt cgccctggat   2400
acagagtgga aagatagagg agaacatatt atttggtaaa gagatgcaga gggagaagta   2460
tgataaagtt cttgaagcgt gctccttaaa gaaagacctg gaaattctct cttttggcga   2520
tcaaacagaa atagggggaga ggggcattaa tttgagcggt ggacagaagc agagaataca   2580
gattgctcgt gctctttacc aagatgctga tgtttaccta tttgatgatc cgttcagtgc   2640
tgtggatgct cataccggat cccatctctt cagtgtaagt cctttcatat atatgcttta   2700
ttttcatgct tgatatattt tacctagcca cttgattgac ccatcccttta attgcaggaa   2760 tgtataatgg ggctattgaa ttcaaaaaca gttttatatg ttacacatca agtggagttt   2820
ttgcctgctg cggatttgat cttggtactc tttccttttca gtaattatgg tttgcttaat   2880
atcatatata gacttaactc atttaactat gatatttctc ttcaggtcat gaaagatgga   2940
aggatcagtg aaactgggaa atacaatgat cttctcaaat taggtagtga cttcatggaa   3000
cttgtgggtg ctcaccaaga agctttaaca gcaattgaca cagttaaggg agaagcattg   3060
agaaagagtg aggaaatgac tggtgataat acaaatgtac agaaggataa aaatatttca   3120
gatggccaaa atggtaaagt ggatgatatt gttggaacaa agggacaaat tgttcaggag   3180
gaggaaagag agaaaggtag tgttggtttt tcagtttact ggaaatatat aacaactgca   3240
tatgagggtc tcttgtgcc atttatgctg ttggcacaag ttggttttca gctccttcaa   3300
attggaagca attattggat ggcgtgggca actcccgtct caaagagtga gccacctcct   3360
gttgggagtt ctactctcat cattgtctat gttgctttag gaattgcaag tgctttatgc   3420
atccttgcta gaaccatgtt tcttgttacc gctggatata agacagcctc tttgcttttc   3480
cataaaatgc atctttgcat tttccgtgct ccaatgtcct tcttcgatgc cacaccgagt   3540
gggcggattc taaacagagt aagtgaatga ttacattttc tttatttagc cccttttttt   3600
tccttattag tgtcaatctt tctgttacat gactaatcaa tgttttgtga aaattagcta   3660
gtaatttcag aattaactca aatgtacttt ggtatgaaaa caggcatcga cagatcaaag   3720
tgcaattgat ctgaatgttc ccattcaagt tggatccttt gccttcacaa taatacagct   3780
tttagggatt attggagtaa tgtcacaagt tgcatggcag tcttcattg tctttattcc   3840 ggtcattgca gtttgcatct ggttggaggt tgctacgacc acctttttcg tgttctttgc   3900
cttcacaatt attctactat atgcttttc acaaagtgag tcataacttt agcgacattc   3960
ataaacgtga gttacattta agtggtgagt ttgttttcat tgcagcaata ttacatacca   4020
tcagcacgag aactggcacg gctaaatggg acatgcaaag ctccagtaat acagcacttt   4080
gccgagacaa tttcaggatc aagcacaatt agaagtttcg atcaggaatc tagattccag   4140
gacacaagta tgaaattgat agacaattat tctcggccta agtttcacat cgctgctgca   4200
```

```
atggagtggc tttgtttgcg tttggatatg ttatctctga tcacttttgc tttctcttta    4260
attttcttga tctctcttcc tgttggaaca attgacccaa gtaagttctc tatcttcatg    4320
ttttctttcc ttgaagtttg ttgtgttgaa taactcttaa gagcacattt tctccgtttc    4380
ttgatttaca ggtgttgctg gcttagctgt tacatatggg cttaatctga acataataca    4440
agctcgggtt gtttggaatc tttgtatgat ggaaaataaa attatttctg ttgaaagaat    4500
acttcagtat actgctcttc caagtgaatc tcctcttatc atagaatcca acagaccaga    4560
ccctaactgg ccatcttgtg gagaggttga ttttagcaat cttcaggtaa attaagttat    4620
tctctggtgt taattatgca ggttaatttg ttggtatggg ttggtatatc tgaaaacttt    4680
taataggtcc gatatgctcc tcacatgcct ctcgtgttgc gaggccttac atgcactttc    4740
tttggtggaa agaagactgg aattgtcggt aggacaggca gcggtaaatc tactctaata    4800
cagaccctct tccgcatagt tgaaccagct gctggacaaa taaaaataga tggtatcagc    4860
atctcctcaa ttggtttgca tgatctacgg tctagattga gtataattcc acaggatcca    4920
actatgtttg agggaacagt tcgcagcaac ctagacccgc ttgaagagta ttcagatgaa    4980
caaatttggg aggtgacagc ttggttttgc ctattttttgg attattttg tttcagatag    5040
gaaaatgaca aattttattt tattgagaaa ctttgtttga tgttatgctt caggcgctcg    5100
ataagtgtca gctaggagaa gaagtgagga agaaagaagg caaactttat tctacaggta    5160
acttcaagaa ccacatcatt ttctgatgat ttccactttt agagctgtaa taatcatctt    5220
cattgcgttg ctgcagtatc tgagaatgga gagaactgga gtgtaggcca aaggcagctg    5280
gtctgccttg gccgtgtgct actgaaaaag agcaaggtcc tggtccttga cgaggctaca    5340
gcatctgtcg acactgcaac tgataatctt attcagcaaa ctctaaggct gcacttctct    5400
gattccacgg ttataaccat tgctcatagg attacatctg tgcttgacag tgatatggtc    5460
ctactattag atcatggtaa gaatcatcgt ttatgttctg gagcaagcgg agaaggaaat    5520
tcttggtagt tacctttttt ttatgctatg ctgcagggct cattgctgaa tacggcactc    5580
cagccaggtt gttagagaac gaatcctcat tgtttgctaa gctcgtggca gagtatagta    5640
tgaggtcaaa ttcaagtttt gagaatgttt cagacatgtg agtctcagaa actaatcttc    5700
gttaataatg ttcacgacg atgatgatga aaattagggg actctagact agtaccttag    5760
tcgatagtgt tttgagtttc catctgtgga caccatagct gaacaagaa ccagcgaaat    5820
gcaggtcatg cctgtggctt gagggaaact gcaacaatcc tatggcaggg aaagaaacct    5880
acatctagta tgcaatatt gattgtgaag tggcatttgt ttttgtttag acttttttgat    5940
gagaaaatgt atacgtaact ttgtgtttac aataatttga atgtatgttg agtcaagtga    6000
ttagttagtt aagagtgcac ggattttgct acttctgggt aaaagaagta aaccttgttg    6060
ttgagagttg aaagtgaaat tactagtgtc gaattttgcc gcataagcta aatgaaacac    6120
ttttacgata aactcctagt gcaacaaagg aaaaattcat tggcaagact agctgtttat    6180
gtttcacgac                                                            6190
```

<210> SEQ ID NO 29
<211> LENGTH: 5383
<212> TYPE: DNA
<213> ORGANISM: Nicotiana tabacum

<400> SEQUENCE: 29

```
atggaaattg caagggcat gtctgtgttt caatctttga ggtatgttgg cgttgatgaa    60
```

```
tccctccgaa accccatttt cttacgtgtc attagttgtt ctttgcacct gggattgttc      120
cttgtaattc ttgggttgtg ttgttggaat acaatcagga gggacaataa tgctggccac      180
aaacagagta gtactaggaa tgctaggttc ttgtactaca aatcaacctt gttttgttca      240
ataggtctag ccatctttag cttttgtgtta tgtttgttag ctcattttta ttggtataga      300
aatggttggt cagaagaaaa aattataacc cttttggatt ttgcattaaa gttgctagct      360
tggttgtcaa tctctgtttt cttgcacacc cagttcctta attcttgtga aaccaaatac      420
cctcttgttt taagagtttg gtgggggctt ttcttctttg tttcttgtta ttgccttgtt      480
atagaccttg tttatgggga aaagaaccaa tctttaccaa ctcaattttg tatacctgat      540
gttgttttca ctcttatggg gttattcttc tgttttgttg ggtttattgt taaaacagag      600
agtgaggaga atatgcttca ggaacccctc ttaaatggta gtgttgccaa tggcatggac      660
tcaaagaagt ctactgggga tcaaactgtc accccttatg ccaatgctaa cattttttagt     720 ctctttactt tctcttggat gggtccccta atttctgttg caacaagaa accattagac       780 cttgaggatg ttcctcagct tcactttgat gatagtgtca aagggagttt tcctattttt      840
agagaaaaac tagaatctgt gggtggggga aatagtaacc gtgtgactac cttcatgctg      900
gtgaaggctt tggttttcac agcacggaag agatagtgt tatcggctct cttcgtgctt       960
ctttacgctc tggcgtcttt tgttggcccg tacctcattg ataccttagt tcagtatctg     1020
aatgaaaaac gagactttga taatgaaggt tatgtcttag tggctgcatt cttcgttgca     1080
aagttggtgg agtgtttggc gcaaaggcat tggttttca aggtgcagca gggagggtat     1140
cgggcacggg cagcactggt ttccaaaatc tacaacaagg gtttaaccct ctcctgtcag     1200
tcaaagcaaa gccacactag tggagagatc atcaattta tgacagttga tgccgagagg     1260
attggtgact tcgttggta tatgcatgat ccttggatgg taatcataca agttgctctg     1320
gcattggtga tactctataa aaatcttggc ctagctgcta tcgccgcgtt tgttgctaca     1380
ataatagtga tgttggcaaa catccctta gggagtttgc aggagaagtt tcaggagaaa     1440
ctcatggaat cgaaagatag aaggatgaag gctacatctg aagtcttaag gaatatgaga     1500
atactcaagc ttcaagcttg ggagatgaag tttctgtcta ggatcttgga cctcaggact     1560
acagaggcag gatggttgat gaaatatgtg tacacatcag ctatgactac ttttgtcttc     1620
tgggttgctc ctacatttgt ttctgtgacg acctttggcg ctgcaatgct tatgggaatc     1680
ccacttgaat ctgggaagat attgtctgca cttgcgacat ttagaattct tcaagagccc     1740
atctacaatc tcccagatac aatttcaatg attgctcaaa ccaaagtttc tcttgatcgt     1800
attgcatctt tcctttctct tgatgacttg cagcctgatg tcatagagaa gcttccaaaa     1860
ggtagttctg atgaagcaat tgagattgta ggtgggaact tcgcttggga tgcatccacc     1920
tcgactccac ttctaaagga tgtaaatctt agagtgctta atggcatgag agttgccatt     1980
tgtggtacag ttggttcagg aaaatcaagc ttactgtcta gcattttagg agagatgccc     2040
aaattatcag ggactattaa acttagtgga acgaaggctt atgttgcaca gtcgccctgg     2100
atacagagtg gaaagataga ggagaacata ttatttggta agagatgca gagggagaag     2160 tatgataaag ttcttgaagc gtgctcctta aagaaagacc tggaaattct ctcttttggc     2220
gatcaaacag aaatagggga gagggcatt aatttgagcg gtggacagaa gcagagaata     2280
cagattgctc gtgctcttta ccaagatgct gatgtttacc tatttgatga tccgttcagt     2340
gctgtggatg ctcataccgg atcccatctc ttcagtgtaa gtccttttcat atatatgctt     2400 tattttcatg cttgatatat tttacctagc cacttgattg acccatcctt taattgcagg     2460
```

```
aatgtataat ggggctattg aattcaaaaa cagttttata tgttacacat caagtggagt   2520
ttttgcctgc tgcggatttg atcttggtac tctttccttt cagtaattat ggtttgctta   2580
atatcatata tagacttaac tcatttaact atgatatttc tcttcaggtc atgaaagatg   2640
gaaggatcag tgaaactggg aaatacaatg atcttctcaa attaggtagt gacttcatgg   2700
aacttgtggg tgctcaccaa gaagctttaa cagcaattga cacagttaag ggagaagcat   2760
tgagaaagag tgaggaaatg actggtgata atacaaatgt acagaaggat aaaaatattt   2820
cagatggcca aaatggtaaa gtggatgata ttgttggaac aaagggacaa attgttcagg   2880
aggaggaaag agaaaaggt agtgttggtt tttcagttta ctggaaatat ataacaactg   2940
catatggagg tgctcttgtg ccatttatgc tgttggcaca agttggtttt cagctccttc   3000
aaattggaag caattattgg atggcgtggg caactcccgt ctcaaagagt gagccacctc   3060
ctgttgggag ttctactctc atcattgtct atgttgcttt aggaattgca agtgctttat   3120
gcatccttgc tagaaccatg tttcttgtta ccgctggata taagacagcc tctttgcttt   3180
tccataaaat gcatctttgc attttccgtg ctccaatgtc cttcttcgat gccacaccga   3240
gtgggcggat tctaaacaga gtaagtgaat gattacattt tctttattta gccccttttt   3300
tttccttatt agtgtcaatc tttctgttac atgactaatc aatgttttgt gaaaattagc   3360
tagtaatttc agaattaact caaatgtact ttggtatgaa acaggcatc gacagatcaa    3420 agtgcaattg atctgaatgt tcccattcaa gttggatcct tgccttcac aataatacag    3480 cttttaggga ttattggagt aatgtcacaa gttgcatggc aggtcttcat tgtctttatt   3540
ccggtcattg cagtttgcat ctggttggag gttgctacga ccacctttttt cgtgttctttt   3600 gccttcacaa ttattctact atatgctttt tcacaaagtg agtcataact ttagcgacat   3660
tcataaacgt gagttacatt taagtggtga gtttgttttc attgcagcaa tattacatac   3720
catcagcacg agaactggca cggctaaatg ggacatgcaa agctccagta atacagcact   3780
ttgccgagac aatttcagga tcaagcacaa ttagaagttt cgatcaggaa tctagattcc   3840
aggacacaag tatgaaattg atagacaatt attctcggcc taagtttcac atcgctgctg   3900
caatggagtg gctttgtttg cgtttggata tgttatctct gatcactttt gctttctctt   3960
taattttctt gatctctctt cctgttggaa caattgaccc aagtaagttc tctatcttca   4020
tgttttcttt ccttgaagtt tgttgtgttg ataactctt aagagcacat tttctccgtt   4080
tcttgattta caggtgttgc tggcttagct gttacatatg gcttaatct gaacataata    4140 caagctcggg ttgtttggaa tctttgtatg atggaaaata aaattatttc tgttgaaaga   4200
atacttcagt atactgctct tccaagtgaa tctcctctta tcatagaatc caacagacca   4260
gaccctaact ggccatcttg tggagaggtt gattttagca atcttcaggt aaattaagtt   4320
attctctggt gttaattatg caggttaatt tgttggtatg ggttggtata tctgaaaact   4380
tttaataggt ccgatatgct cctcacatgc ctctcgtgtt gcgaggcctt acatgcactt   4440
tctttggtgg aaagaagact ggaattgtcg gtaggacagg cagcggtaaa tctactctaa   4500
tacagaccct cttccgcata gttgaaccag ctgctgaca aataaaaata gatggtatca   4560
gcatctcctc aattggtttg catgatctac ggtctagatt gagtataatt ccacaggatc   4620
caactatgtt tgagggaaca gttcgcagca acctagaccc gcttgaagag tattcagatg   4680
aacaaatttg ggaggtgaca gcttggtttt gcctattttt ggatttattt tgtttcagat   4740
aggaaaatga caaattttat tttattgaga aacttttgttt gatgttatgc ttcaggcgct   4800
```

| | |
|---|---|
| cgataagtgt cagctaggag aagaagtgag gaagaaagaa ggcaaacttt attctacagg | 4860 |
| taacttcaag aaccacatca tttttctgatg atttccactt ttagagctgt aataatcatc | 4920 |
| ttcattgcgt tgctgcagta tctgagaatg gagagaactg gagtgtaggc caaaggcagc | 4980 |
| tggtctgcct tggccgtgtg ctactgaaaa agagcaaggt cctggtcctt gacgaggcta | 5040 |
| cagcatctgt cgacactgca actgataatc ttattcagca aactctaagg ctgcacttct | 5100 |
| ctgattccac ggttataacc attgctcata ggattacatc tgtgcttgac agtgatatgg | 5160 |
| tcctactatt agatcatggt aagaatcatc gtttatgttc tggagcaagc ggagaaggaa | 5220 |
| attcttggta gttacctttt ttttatgcta tgctgcaggg ctcattgctg aatacggcac | 5280 |
| tccagccagg ttgttagaga acgaatcctc attgtttgct aagctcgtgg cagagtatag | 5340 |
| tatgaggtca aattcaagtt ttgagaatgt ttcagacatg tga | 5383 |

<210> SEQ ID NO 30
<211> LENGTH: 117
<212> TYPE: DNA
<213> ORGANISM: Nicotiana tabacum

<400> SEQUENCE: 30

| | |
|---|---|
| gtatgttggc gttgatgaat ccctccgaaa ccccatttc ttacgtgtca ttagttgttc | 60 |
| tttgcacctg ggattgttcc ttgtaattct tgggttgtgt tgttggaata caatcag | 117 |

<210> SEQ ID NO 31
<211> LENGTH: 83
<212> TYPE: DNA
<213> ORGANISM: Nicotiana tabacum

<400> SEQUENCE: 31

| | |
|---|---|
| gtaagtcctt tcatatatat gctttatttt catgcttgat atattttacc tagccacttg | 60 |
| attgacccat cctttaattg cag | 83 |

<210> SEQ ID NO 32
<211> LENGTH: 81
<212> TYPE: DNA
<213> ORGANISM: Nicotiana tabacum

<400> SEQUENCE: 32

| | |
|---|---|
| gtactctttc ctttcagtaa ttatggtttg cttaatatca tatatagact taactcattt | 60 |
| aactatgata tttctcttca g | 81 |

<210> SEQ ID NO 33
<211> LENGTH: 145
<212> TYPE: DNA
<213> ORGANISM: Nicotiana tabacum

<400> SEQUENCE: 33

| | |
|---|---|
| gtaagtgaat gattacattt tctttatta gcccctttt tttccttatt agtgtcaatc | 60 |
| tttctgttac atgactaatc aatgttttgt gaaaattagc tagtaatttc agaattaact | 120 |
| caaatgtact ttggtatgaa aacag | 145 |

<210> SEQ ID NO 34
<211> LENGTH: 137
<212> TYPE: DNA
<213> ORGANISM: Nicotiana tabacum

<400> SEQUENCE: 34

| | |
|---|---|
| gttgctacga ccaccttttt cgtgttcttt gccttcacaa ttattctact atatgctttt | 60 |

```
tcacaaagtg agtcataact ttagcgacat tcataaacgt gagttacatt taagtggtga      120
gtttgttttc attgcag                                                    137

<210> SEQ ID NO 35
<211> LENGTH: 91
<212> TYPE: DNA
<213> ORGANISM: Nicotiana tabacum

<400> SEQUENCE: 35
gtaagttctc tatcttcatg ttttctttcc ttgaagtttg ttgtgttgaa taactcttaa       60
gagcacattt tctccgtttc ttgatttaca g                                     91

<210> SEQ ID NO 36
<211> LENGTH: 80
<212> TYPE: DNA
<213> ORGANISM: Nicotiana tabacum

<400> SEQUENCE: 36
gtaaattaag ttattctctg gtgttaatta tgcaggttaa tttgttggta tgggttggta       60
tatctgaaaa cttttaatag                                                  80

<210> SEQ ID NO 37
<211> LENGTH: 101
<212> TYPE: DNA
<213> ORGANISM: Nicotiana tabacum

<400> SEQUENCE: 37
gtgacagctt ggttttgcct atttttggat ttattttgtt tcagatagga aaatgacaaa       60
ttttatttta ttgagaaact ttgtttgatg ttatgcttca g                          101

<210> SEQ ID NO 38
<211> LENGTH: 79
<212> TYPE: DNA
<213> ORGANISM: Nicotiana tabacum

<400> SEQUENCE: 38
gtaacttcaa gaaccacatc attttctgat gatttccact tttagagctg taataatcat       60
cttcattgcg ttgctgcag                                                   79

<210> SEQ ID NO 39
<211> LENGTH: 80
<212> TYPE: DNA
<213> ORGANISM: Nicotiana tabacum

<400> SEQUENCE: 39
gtaagaatca tcgtttatgt tctggagcaa gcggagaagg aaattcttgg tagttacctt       60
ttttttatgc tatgctgcag                                                  80

<210> SEQ ID NO 40
<211> LENGTH: 41
<212> TYPE: DNA
<213> ORGANISM: Nicotiana tabacum

<400> SEQUENCE: 40
atggaaattg caaagggcat gtctgtgttt caatctttga g                          41

<210> SEQ ID NO 41
<211> LENGTH: 2218
<212> TYPE: DNA
```

<213> ORGANISM: Nicotiana tabacum

<400> SEQUENCE: 41

```
gagggacaat aatgctggcc acaaacagag tagtactagg aatgctaggt tcttgtacta        60
caaatcaacc ttgttttgtt caataggtct agccatcttt agctttgtgt tatgtttgtt       120
agctcatttt tattggtata gaaatggttg gtcagaagaa aaaattataa ccttttgga        180
ttttgcatta aagttgctag cttggttgtc aatctctgtt ttcttgcaca cccagttcct       240
taattcttgt gaaaccaaat accctcttgt tttaagagtt tggtgggggc ttttcttctt       300
tgtttcttgt tattgccttg ttatagacct tgtttatggg gaaaagaacc aatctttacc       360
aactcaattt tgtatacctg atgttgtttt cactcttatg gggttattct tctgttttgt       420
tgggtttatt gttaaaacag agagtgagga gaatatgctt caggaacccc tcttaaatgg       480
tagtgttgcc aatggcatgg actcaaagaa gtctactggg gatcaaactg tcacccctta       540
tgccaatgct aacattttta gtctctttac tttctcttgg atgggtcccc taatttctgt       600
tggcaacaag aaaccattag accttgagga tgttcctcag cttcactttg atgatagtgt       660
caaagggagt tttcctattt ttagagaaaa actagaatct gtgggtgggg gaaatagtaa       720
ccgtgtgact accttcatgc tggtgaaggc tttggttttc acagcacgga aggagatagt       780
gttatcggct ctcttcgtgc ttctttacgc tctggcgtct tttgttggcc cgtacctcat       840
tgataccttg gttcagtatc tgaatggaaa acgagacttt gataatgaag ttatgtctt        900
agtggctgca ttcttcgttg caaagttggt ggagtgtttg gcgcaaaggc attggttttt       960
caaggtgcag cagggagggt atcgggcacg ggcagcactg gtttccaaaa tctacaacaa      1020
gggtttaacc ctctcctgtc agtcaaagca aagccacact agtggagaga tcatcaattt      1080
tatgacagtt gatgccgaga ggattggtga cttcggttgg tatatgcatg atccttggat      1140
ggtaatcata caagttgctc tggcattggt gatactctat aaaaatcttg gcctagctgc      1200
tatcgccgcg tttgttgcta caataatagt gatgttggca acatcccctt tagggagttt      1260
gcaggagaag tttcaggaga aactcatgga atcgaaagat agaaggatga aggctacatc      1320
tgaagtctta aggaatatga gaatactcaa gcttcaagct tgggagatga gtttctgtc       1380
taggatcttg gacctcagga ctacagaggc aggatggttg atgaaatatg tgtacacatc      1440
agctatgact acttttgtct ctgggttgc tcctacattt gtttctgtga cgacctttgg       1500
cgctgcaatg cttatgggaa tcccacttga atctgggaag atattgtctg cacttgcgac      1560
atttagaatt cttcaagagc ccatctacaa tctcccagat acaatttcaa tgattgctca      1620
aaccaaagtt tctcttgatc gtattgcatc tttcctttct cttgatgact gcagcctga       1680
tgtcatagag aagcttccaa aaggtagttc tgatgaagca attgagattg taggtgggaa      1740
cttcgcttgg gatgcatcca cctcgactcc acttctaaag gatgtaaatc ttagagtgct      1800
taatggcatg agagttgcca tttgtggtac agttggttca ggaaaatcaa gcttactgtc      1860
tagcattta ggagagatgc ccaaattatc agggactatt aaacttagtg gaacgaaggc       1920
ttatgttgca cagtcgccct ggatacagag tggaaagata gaggagaaca tattatttgg      1980
taaagagatg cagagggaga agtatgataa agttcttgaa gcgtgctcct aaagaaaga       2040
cctggaaatt ctctcttttg gcgatcaaac agaaataggg gagaggggca ttaatttgag      2100
cggtggacag aagcagagaa tacagattgc tcgtgctctt taccaagatg ctgatgttta      2160
cctatttgat gatccgttca gtgctgtgga tgctcatacc ggatcccatc tcttcagt       2218
```

```
<210> SEQ ID NO 42
<211> LENGTH: 87
<212> TYPE: DNA
<213> ORGANISM: Nicotiana tabacum

<400> SEQUENCE: 42
gaatgtataa tggggctatt gaattcaaaa acagttttat atgttacaca tcaagtggag      60
tttttgcctg ctgcggattt gatcttg                                         87

<210> SEQ ID NO 43
<211> LENGTH: 633
<212> TYPE: DNA
<213> ORGANISM: Nicotiana tabacum

<400> SEQUENCE: 43
gtcatgaaag atggaaggat cagtgaaact gggaaataca atgatcttct caaattaggt      60
agtgacttca tggaacttgt gggtgctcac caagaagctt taacagcaat tgacacagtt     120
aagggagaag cattgagaaa gagtgaggaa atgactggtg ataatacaaa tgtacagaag     180
gataaaaata tttcagatgg ccaaaatggt aaagtggatg atattgttgg aacaaaggga     240
caaattgttc aggaggagga aagagagaaa ggtagtgttg ttttttcagt ttactggaaa     300
tatataacaa ctgcatatgg aggtgctctt gtgccattta tgctgttggc acaagttggt     360
tttcagctcc ttcaaattgg aagcaattat tggatggcgt gggcaactcc cgtctcaaag     420
agtgagccac ctcctgttgg gagttctact ctcatcattg tctatgttgc tttaggaatt     480
gcaagtgctt tatgcatcct tgctagaacc atgtttcttg ttaccgctgg atataagaca     540
gcctctttgc ttttccataa aatgcatctt tgcatttttcc gtgctccaat gtccttcttc     600
gatgccacac cgagtgggcg gattctaaac aga                                  633

<210> SEQ ID NO 44
<211> LENGTH: 165
<212> TYPE: DNA
<213> ORGANISM: Nicotiana tabacum

<400> SEQUENCE: 44
gcatcgacag atcaaagtgc aattgatctg aatgttccca ttcaagttgg atcctttgcc      60
ttcacaataa tacagctttt agggattatt ggagtaatgt cacaagttgc atggcaggtc     120
ttcattgtct ttattccggt cattgcagtt tgcatctggt tggag                     165

<210> SEQ ID NO 45
<211> LENGTH: 295
<212> TYPE: DNA
<213> ORGANISM: Nicotiana tabacum

<400> SEQUENCE: 45
caatattaca taccatcagc acgagaactg gcacggctaa atgggacatg caaagctcca      60
gtaatacagc actttgccga gacaatttca ggatcaagca caattagaag tttcgatcag     120
gaatctagat tccaggacac aagtatgaaa ttgatagaca attattctcg gcctaagttt     180
cacatcgctg ctgcaatgga gtggcttttgt ttgcgtttgg atatgttatc tctgatcact     240
tttgctttct ctttaatttt cttgatctct cttcctgttg gaacaattga cccaa          295

<210> SEQ ID NO 46
<211> LENGTH: 215
<212> TYPE: DNA
<213> ORGANISM: Nicotiana tabacum
```

<400> SEQUENCE: 46
gtgttgctgg cttagctgtt acatatgggc ttaatctgaa cataatacaa gctcggttg    60 tttggaatct ttgtatgatg gaaaataaaa ttatttctgt tgaaagaata cttcagtata   120
ctgctcttcc aagtgaatct cctcttatca tagaatccaa cagaccagac cctaactggc   180
catcttgtgg agaggttgat tttagcaatc ttcag                               215

<210> SEQ ID NO 47
<211> LENGTH: 306
<212> TYPE: DNA
<213> ORGANISM: Nicotiana tabacum

<400> SEQUENCE: 47
gtccgatatg ctcctcacat gcctctcgtg ttgcgaggcc ttacatgcac tttctttggt    60
ggaaagaaga ctggaattgt cggtaggaca ggcagcggta aatctactct aatacagacc   120
ctcttccgca tagttgaacc agctgctgga caaataaaaa tagatggtat cagcatctcc   180
tcaattggtt tgcatgatct acggtctaga ttgagtataa ttccacagga tccaactatg   240
tttgagggaa cagttcgcag caacctagac ccgcttgaag agtattcaga tgaacaaatt   300
tgggag                                                               306

<210> SEQ ID NO 48
<211> LENGTH: 64
<212> TYPE: DNA
<213> ORGANISM: Nicotiana tabacum

<400> SEQUENCE: 48
gcgctcgata agtgtcagct aggagaagaa gtgaggaaga agaaggcaa actttattct     60 acag                                                                  64

<210> SEQ ID NO 49
<211> LENGTH: 240
<212> TYPE: DNA
<213> ORGANISM: Nicotiana tabacum

<400> SEQUENCE: 49
tatctgagaa tggagagaac tggagtgtag gccaaaggca gctggtctgc cttggccgtg    60
tgctactgaa aaagagcaag gtcctggtcc ttgacgaggc tacagcatct gtcgacactg   120
caactgataa tcttattcag caaactctaa ggctgcactt ctctgattcc acggttataa   180
ccattgctca taggattaca tctgtgcttg acagtgatat ggtcctacta ttagatcatg   240

<210> SEQ ID NO 50
<211> LENGTH: 125
<212> TYPE: DNA
<213> ORGANISM: Nicotiana tabacum

<400> SEQUENCE: 50
ggctcattgc tgaatacggc actccagcca ggttgttaga gaacgaatcc tcattgtttg    60
ctaagctcgt ggcagagtat agtatgaggt caaattcaag ttttgagaat gtttcagaca   120
tgtga                                                                125

<210> SEQ ID NO 51
<211> LENGTH: 4389
<212> TYPE: DNA
<213> ORGANISM: Nicotiana tabacum

<400> SEQUENCE: 51

```
atggaaattg caaagggcat gtctgtgttt caatctttga ggagggacaa taatgctggc    60
cacaaacaga gtagtactag gaatgctagg ttcttgtact acaaatcaac cttgttttgt   120
tcaataggtc tagccatctt tagctttgtg ttatgtttgt tagctcattt ttattggtat   180
agaaatggtt ggtcagaaga aaaaattata acccttttgg attttgcatt aaagttgcta   240
gcttggttgt caatctctgt tttcttgcac acccagttcc ttaattcttg tgaaaccaaa   300
taccctcttg ttttaagagt ttggtggggg cttttcttct ttgtttcttg ttattgcctt   360
gttatagacc ttgtttatgg ggaaaagaac caatctttac caactcaatt ttgtatacct   420
gatgttgttt tcactcttat ggggttattc ttctgttttg ttgggtttat tgttaaaaca   480
gagagtgagg agaatatgct tcaggaaccc ctcttaaatg gtagtgttgc caatggcatg   540
gactcaaaga gtctactggg gatcaaact gtcacccctt atgccaatgc taacattttt   600
agtctcttta ctttctcttg gatgggtccc ctaatttctg ttggcaacaa gaaaccatta   660
gaccttgagg atgttcctca gcttcacttt gatgatagtg tcaaagggag ttttcctatt   720
tttagagaaa aactagaatc tgtgggtggg ggaaatagta accgtgtgac taccttcatg   780
ctggtgaagg ctttggtttt cacagcacgg aaggagatag tgttatcggc tctcttcgtg   840
cttctttacg ctctggcgtc ttttgttggc ccgtacctca ttgataccctt agttcagtat   900
ctgaatggaa aacgagactt tgataatgaa ggttatgtct tagtggctgc attcttcgtt   960
gcaaagttgg tggagtgttt ggcgcaaagg cattggtttt tcaaggtgca gcagggaggg  1020
tatcgggcac gggcagcact ggtttccaaa atctacaaca agggtttaac cctctcctgt  1080
cagtcaaagc aaagccacac tagtggagag atcatcaatt ttatgacagt tgatgccgag  1140
aggattggtg acttcggttg gtatatgcat gatccttgga tggtaatcat acaagttgct  1200
ctggcattgg tgatactcta taaaaatctt ggcctagctg ctatcgccgc gtttgttgct  1260
acaataatag tgatgttggc aaacatccct ttagggagtt tgcaggagaa gtttcaggag  1320
aaactcatgg aatcgaaaga tagaaggatg aaggctacat ctgaagtctt aaggaatatg  1380
agaatactca agcttcaagc ttgggagatg aagtttctgt ctaggatctt ggacctcagg  1440
actacagagg caggatggtt gatgaaatat gtgtacacat cagctatgac tactttgtc   1500
ttctggttg ctcctacatt tgtttctgtg acgacctttg gcgctgcaat gcttatggga  1560
atcccacttg aatctgggaa gatattgtct gcacttgcga catttagaat tcttcaagag  1620
cccatctaca atctcccaga tacaatttca atgattgctc aaaccaaagt ttctcttgat  1680
cgtattgcat ctttccttc tcttgatgac ttgcagcctg atgtcataga gaagcttcca  1740
aaaggtagtt ctgatgaagc aattgagatt gtaggtggga cttcgcttg gatgcatcc   1800
acctcgactc cacttctaaa ggatgtaaat cttagagtgc ttaatggcat gagagttgcc  1860
atttgtggta cagttggttc aggaaaatca gcttactgt ctagcatttt aggagagatg  1920
cccaaattat cagggactat taaacttagt ggaacgaagg cttatgttgc acagtcgccc  1980
tggatacaga gtgaaagat agaggagaac atattatttg gtaaagagat gcagagggag  2040
aagtatgata agttcttga agcgtgctcc ttaaagaaag acctggaaat tctctctttt  2100
ggcgatcaaa cagaaatagg ggagaggggc attaatttga gcggtggaca gaagcagaga  2160
atacagattg ctcgtgctct ttaccaagat gctgatgttt acctatttga tgatccgttc  2220
agtgctgtgg atgctcatac cggatcccat ctcttcagtg aatgtataat ggggctattg  2280
aattcaaaaa cagttttata tgttacacat caagtggagt ttttgcctgc tgcggatttg  2340
```

```
                                               -continued
atcttggtca tgaaagatgg aaggatcagt gaaactggga aatacaatga tcttctcaaa    2400
ttaggtagtg acttcatgga acttgtgggt gctcaccaag aagctttaac agcaattgac    2460
acagttaagg gagaagcatt gagaaagagt gaggaaatga ctggtgataa tacaaatgta    2520
cagaaggata aaatatttc agatggccaa aatggtaaag tggatgatat tgttggaaca     2580
aagggacaaa ttgttcagga ggaggaaaga gagaaggta gtgttggttt ttcagtttac      2640
tggaaatata taacaactgc atatggaggt gctcttgtgc catttatgct gttggcacaa    2700
gttggttttc agctccttca aattggaagc aattattgga tggcgtgggc aactcccgtc    2760
tcaaagagtg agccacctcc tgttgggagt tctactctca tcattgtcta tgttgcttta    2820
ggaattgcaa gtgctttatg catccttgct agaaccatgt ttcttgttac cgctggatat    2880 aagcagcct ctttgctttt ccataaaatg catctttgca ttttccgtgc tccaatgtcc      2940
ttcttcgatg ccacaccgag tgggcggatt ctaaacagag catcgacaga tcaaagtgca    3000
attgatctga atgttcccat tcaagttgga tcctttgcct tcacaataat acagctttta    3060
gggattattg gagtaatgtc acaagttgca tggcaggtct tcattgtctt tattccggtc    3120
attgcagttt gcatctggtt ggagcaatat tacataccat cagcacgaga actggcacgg    3180
ctaaatggga catgcaaagc tccagtaata cagcactttg ccgagacaat tcaggatca    3240 agcacaatta gaagtttcga tcaggaatct agattccagg acacaagtat gaaattgata    3300
gacaattatt ctcggcctaa gtttcacatc gctgctgcaa tggagtggct ttgtttgcgt    3360
ttggatatgt tatctctgat cacttttgct ttctctttaa ttttcttgat ctctcttcct    3420
gttgaaacaa ttgacccaag tgttgctggc ttagctgtta catatgggct taatctgaac    3480
ataatacaag ctcgggttgt ttggaatctt tgtatgatgg aaaataaat tatttctgtt     3540 gaaagaatac ttcagtatac tgctcttcca agtgaatctc ctcttatcat agaatccaac    3600
agaccagacc ctaactggcc atcttgtgga gaggttgatt ttagcaatct tcaggtccga    3660
tatgctcctc acatgcctct cgtgttgcga ggccttacat gcactttctt tggtggaaag    3720
aagactggaa ttgtcggtag gacaggcagc ggtaaatcta ctctaataca gaccctcttc    3780
cgcatagttg aaccagctgc tggacaaata aaaatagatg gtatcagcat ctcctcaatt    3840 ggttttgcatg atctacggtc tagattgagt ataattccac aggatccaac tatgtttgag   3900
ggaacagttc gcagcaacct agacccgctt gaagagtatt cagatgaaca aatttgggag    3960
gcgctcgata agtgtcagct aggagaagaa gtgaggaaga aagaaggcaa actttattct   4020
acagtatctg agaatggaga gaactggagt gtaggccaaa ggcagctggt ctgccttggc   4080
cgtgtgctac tgaaaaagag caaggtcctg gtccttgacg aggctacagc atctgtcgac   4140
actgcaactg ataatcttat tcagcaaact ctaaggctgc acttctctga ttccacggtt   4200
ataaccattg ctcataggat tacatctgtg cttgacagtg atatggtcct actattagat   4260
catgggctca ttgctgaata cggcactcca gccaggttgt tagagaacga atcctcattg   4320
tttgctaagc tcgtggcaga gtatagtatg aggtcaaatt caagttttga gaatgtttca   4380
gacatgtga                                                           4389

<210> SEQ ID NO 52
<211> LENGTH: 1462
<212> TYPE: PRT
<213> ORGANISM: Nicotiana tabacum

<400> SEQUENCE: 52

Met Glu Ile Ala Lys Gly Met Ser Val Phe Gln Ser Leu Arg Arg Asp
```

-continued

```
1               5                   10                  15
Asn Asn Ala Gly His Lys Gln Ser Ser Thr Arg Asn Ala Arg Phe Leu
                20                  25                  30
Tyr Tyr Lys Ser Thr Leu Phe Cys Ser Ile Gly Leu Ala Ile Phe Ser
                35                  40                  45
Phe Val Leu Cys Leu Leu Ala His Phe Tyr Trp Tyr Arg Asn Gly Trp
 50                  55                  60
Ser Glu Glu Lys Ile Ile Thr Leu Leu Asp Phe Ala Leu Lys Leu Leu
 65                  70                  75                  80
Ala Trp Leu Ser Ile Ser Val Phe Leu His Thr Gln Phe Leu Asn Ser
                85                  90                  95
Cys Glu Thr Lys Tyr Pro Leu Val Leu Arg Val Trp Trp Gly Leu Phe
               100                 105                 110
Phe Phe Val Ser Cys Tyr Cys Leu Val Ile Asp Leu Val Tyr Gly Glu
               115                 120                 125
Lys Asn Gln Ser Leu Pro Thr Gln Phe Cys Ile Pro Asp Val Val Phe
       130                 135                 140
Thr Leu Met Gly Leu Phe Phe Cys Phe Val Gly Phe Ile Val Lys Thr
145                 150                 155                 160
Glu Ser Glu Glu Asn Met Leu Gln Glu Pro Leu Leu Asn Gly Ser Val
               165                 170                 175
Ala Asn Gly Met Asp Ser Lys Lys Ser Thr Gly Asp Gln Thr Val Thr
               180                 185                 190
Pro Tyr Ala Asn Ala Asn Ile Phe Ser Leu Phe Thr Phe Ser Trp Met
               195                 200                 205
Gly Pro Leu Ile Ser Val Gly Asn Lys Lys Pro Leu Asp Leu Glu Asp
       210                 215                 220
Val Pro Gln Leu His Phe Asp Asp Ser Val Lys Gly Ser Phe Pro Ile
225                 230                 235                 240
Phe Arg Glu Lys Leu Glu Ser Val Gly Gly Asn Ser Asn Arg Val
               245                 250                 255
Thr Thr Phe Met Leu Val Lys Ala Leu Val Phe Thr Ala Arg Lys Glu
               260                 265                 270
Ile Val Leu Ser Ala Leu Phe Val Leu Leu Tyr Ala Leu Ala Ser Phe
       275                 280                 285
Val Gly Pro Tyr Leu Ile Asp Thr Leu Val Gln Tyr Leu Asn Gly Lys
       290                 295                 300
Arg Asp Phe Asp Asn Glu Gly Tyr Val Leu Val Ala Ala Phe Phe Val
305                 310                 315                 320
Ala Lys Leu Val Glu Cys Leu Ala Gln Arg His Trp Phe Phe Lys Val
               325                 330                 335
Gln Gln Gly Gly Tyr Arg Ala Arg Ala Ala Leu Val Ser Lys Ile Tyr
               340                 345                 350
Asn Lys Gly Leu Thr Leu Ser Cys Gln Ser Lys Gln Ser His Thr Ser
       355                 360                 365
Gly Glu Ile Ile Asn Phe Met Thr Val Asp Ala Glu Arg Ile Gly Asp
       370                 375                 380
Phe Gly Trp Tyr Met His Asp Pro Trp Met Val Ile Gln Val Ala
385                 390                 395                 400
Leu Ala Leu Val Ile Leu Tyr Lys Asn Leu Gly Leu Ala Ala Ile Ala
               405                 410                 415
Ala Phe Val Ala Thr Ile Ile Val Met Leu Ala Asn Ile Pro Leu Gly
               420                 425                 430
```

```
Ser Leu Gln Glu Lys Phe Gln Glu Lys Leu Met Glu Ser Lys Asp Arg
        435                 440                 445

Arg Met Lys Ala Thr Ser Glu Val Leu Arg Asn Met Arg Ile Leu Lys
    450                 455                 460

Leu Gln Ala Trp Glu Met Lys Phe Leu Ser Arg Ile Leu Asp Leu Arg
465                 470                 475                 480

Thr Thr Glu Ala Gly Trp Leu Met Lys Tyr Val Tyr Thr Ser Ala Met
                485                 490                 495

Thr Thr Phe Val Phe Trp Val Ala Pro Thr Phe Val Ser Val Thr Thr
            500                 505                 510

Phe Gly Ala Ala Met Leu Met Gly Ile Pro Leu Glu Ser Gly Lys Ile
        515                 520                 525

Leu Ser Ala Leu Ala Thr Phe Arg Ile Leu Gln Glu Pro Ile Tyr Asn
    530                 535                 540

Leu Pro Asp Thr Ile Ser Met Ile Ala Gln Thr Lys Val Ser Leu Asp
545                 550                 555                 560

Arg Ile Ala Ser Phe Leu Ser Leu Asp Asp Leu Gln Pro Asp Val Ile
                565                 570                 575

Glu Lys Leu Pro Lys Gly Ser Ser Asp Glu Ala Ile Glu Ile Val Gly
            580                 585                 590

Gly Asn Phe Ala Trp Asp Ala Ser Thr Ser Thr Pro Leu Leu Lys Asp
        595                 600                 605

Val Asn Leu Arg Val Leu Asn Gly Met Arg Val Ala Ile Cys Gly Thr
    610                 615                 620

Val Gly Ser Gly Lys Ser Ser Leu Leu Ser Ser Ile Leu Gly Glu Met
625                 630                 635                 640

Pro Lys Leu Ser Gly Thr Ile Lys Leu Ser Gly Thr Lys Ala Tyr Val
                645                 650                 655

Ala Gln Ser Pro Trp Ile Gln Ser Gly Lys Ile Glu Glu Asn Ile Leu
            660                 665                 670

Phe Gly Lys Glu Met Gln Arg Glu Lys Tyr Asp Lys Val Leu Glu Ala
        675                 680                 685

Cys Ser Leu Lys Lys Asp Leu Glu Ile Leu Ser Phe Gly Asp Gln Thr
    690                 695                 700

Glu Ile Gly Glu Arg Gly Ile Asn Leu Ser Gly Gly Gln Lys Gln Arg
705                 710                 715                 720

Ile Gln Ile Ala Arg Ala Leu Tyr Gln Asp Ala Asp Val Tyr Leu Phe
                725                 730                 735

Asp Asp Pro Phe Ser Ala Val Asp Ala His Thr Gly Ser His Leu Phe
            740                 745                 750

Ser Glu Cys Ile Met Gly Leu Leu Asn Ser Lys Thr Val Leu Tyr Val
        755                 760                 765

Thr His Gln Val Glu Phe Leu Pro Ala Ala Asp Leu Ile Leu Val Met
    770                 775                 780

Lys Asp Gly Arg Ile Ser Glu Thr Gly Lys Tyr Asn Asp Leu Leu Lys
785                 790                 795                 800

Leu Gly Ser Asp Phe Met Glu Leu Val Gly Ala His Gln Glu Ala Leu
                805                 810                 815

Thr Ala Ile Asp Thr Val Lys Gly Glu Ala Leu Arg Lys Ser Glu Glu
            820                 825                 830

Met Thr Gly Asp Asn Thr Asn Val Gln Lys Asp Lys Asn Ile Ser Asp
        835                 840                 845
```

```
Gly Gln Asn Gly Lys Val Asp Asp Ile Val Gly Thr Lys Gly Gln Ile
    850                 855                 860

Val Gln Glu Glu Glu Arg Glu Lys Gly Ser Val Gly Phe Ser Val Tyr
865                 870                 875                 880

Trp Lys Tyr Ile Thr Thr Ala Tyr Gly Gly Ala Leu Val Pro Phe Met
                885                 890                 895

Leu Leu Ala Gln Val Gly Phe Gln Leu Leu Gln Ile Gly Ser Asn Tyr
            900                 905                 910

Trp Met Ala Trp Ala Thr Pro Val Ser Lys Ser Glu Pro Pro Val
        915                 920                 925

Gly Ser Ser Thr Leu Ile Ile Val Tyr Val Ala Leu Gly Ile Ala Ser
    930                 935                 940

Ala Leu Cys Ile Leu Ala Arg Thr Met Phe Leu Val Thr Ala Gly Tyr
945                 950                 955                 960

Lys Thr Ala Ser Leu Leu Phe His Lys Met His Leu Cys Ile Phe Arg
                965                 970                 975

Ala Pro Met Ser Phe Phe Asp Ala Thr Pro Ser Gly Arg Ile Leu Asn
            980                 985                 990

Arg Ala Ser Thr Asp Gln Ser Ala Ile Asp Leu Asn Val Pro Ile Gln
        995                 1000                1005

Val Gly Ser Phe Ala Phe Thr Ile Ile Gln Leu Leu Gly Ile Ile
    1010                1015                1020

Gly Val Met Ser Gln Val Ala Trp Gln Val Phe Ile Val Phe Ile
    1025                1030                1035

Pro Val Ile Ala Val Cys Ile Trp Leu Glu Gln Tyr Tyr Ile Pro
    1040                1045                1050

Ser Ala Arg Glu Leu Ala Arg Leu Asn Gly Thr Cys Lys Ala Pro
    1055                1060                1065

Val Ile Gln His Phe Ala Glu Thr Ile Ser Gly Ser Ser Thr Ile
    1070                1075                1080

Arg Ser Phe Asp Gln Glu Ser Arg Phe Gln Asp Thr Ser Met Lys
    1085                1090                1095

Leu Ile Asp Asn Tyr Ser Arg Pro Lys Phe His Ile Ala Ala Ala
    1100                1105                1110

Met Glu Trp Leu Cys Leu Arg Leu Asp Met Leu Ser Leu Ile Thr
    1115                1120                1125

Phe Ala Phe Ser Leu Ile Phe Leu Ile Ser Leu Pro Val Gly Thr
    1130                1135                1140

Ile Asp Pro Ser Val Ala Gly Leu Ala Val Thr Tyr Gly Leu Asn
    1145                1150                1155

Leu Asn Ile Ile Gln Ala Arg Val Val Trp Asn Leu Cys Met Met
    1160                1165                1170

Glu Asn Lys Ile Ile Ser Val Glu Arg Ile Leu Gln Tyr Thr Ala
    1175                1180                1185

Leu Pro Ser Glu Ser Pro Leu Ile Ile Glu Ser Asn Arg Pro Asp
    1190                1195                1200

Pro Asn Trp Pro Ser Cys Gly Glu Val Asp Phe Ser Asn Leu Gln
    1205                1210                1215

Val Arg Tyr Ala Pro His Met Pro Leu Val Leu Arg Gly Leu Thr
    1220                1225                1230

Cys Thr Phe Phe Gly Gly Lys Lys Thr Gly Ile Val Gly Arg Thr
    1235                1240                1245

Gly Ser Gly Lys Ser Thr Leu Ile Gln Thr Leu Phe Arg Ile Val
```

```
      1250                1255                1260
Glu Pro Ala Ala Gly Gln Ile Lys Ile Asp Gly Ile Ser Ile Ser
      1265                1270                1275

Ser Ile Gly Leu His Asp Leu Arg Ser Arg Leu Ser Ile Ile Pro
      1280                1285                1290

Gln Asp Pro Thr Met Phe Glu Gly Thr Val Arg Ser Asn Leu Asp
      1295                1300                1305

Pro Leu Glu Glu Tyr Ser Asp Glu Gln Ile Trp Glu Ala Leu Asp
      1310                1315                1320

Lys Cys Gln Leu Gly Glu Val Arg Lys Lys Glu Gly Lys Leu
      1325                1330                1335

Tyr Ser Thr Val Ser Glu Asn Gly Glu Asn Trp Ser Val Gly Gln
      1340                1345                1350

Arg Gln Leu Val Cys Leu Gly Arg Val Leu Leu Lys Lys Ser Lys
      1355                1360                1365

Val Leu Val Leu Asp Glu Ala Thr Ala Ser Val Asp Thr Ala Thr
      1370                1375                1380

Asp Asn Leu Ile Gln Gln Thr Leu Arg Leu His Phe Ser Asp Ser
      1385                1390                1395

Thr Val Ile Thr Ile Ala His Arg Ile Thr Ser Val Leu Asp Ser
      1400                1405                1410

Asp Met Val Leu Leu Leu Asp His Gly Leu Ile Ala Glu Tyr Gly
      1415                1420                1425

Thr Pro Ala Arg Leu Leu Glu Asn Glu Ser Ser Leu Phe Ala Lys
      1430                1435                1440

Leu Val Ala Glu Tyr Ser Met Arg Ser Asn Ser Ser Phe Glu Asn
      1445                1450                1455

Val Ser Asp Met
      1460

<210> SEQ ID NO 53
<211> LENGTH: 386
<212> TYPE: DNA
<213> ORGANISM: Nicotiana tabacum

<400> SEQUENCE: 53
ttgttgataa cggagataac tggagtgtcg gacagaggca gcttctttgc ttgggaagag    60
tgatgctaaa acgtagcaga cttctatttta tggatgaggc aactgcctct gttgattcac  120
agacagatgc agtgattcag aaaatcatcc gcgaggactt tgcggcctgt actataatca  180
gcattgccca cagaatacca acagtcatgg actgtgatag agttcttgtt atagatgcag  240
gtgctgattt ctctcctttt actttgtacc ttattttgaa tctggtaaat gattatttat  300
ctgtatgtga tggtttccaa ccaatcatag tcagtacctt tatgaagaaa ttgcctaatg  360
ttagccaagt agtagtaaat gcatga                                        386

<210> SEQ ID NO 54
<211> LENGTH: 24
<212> TYPE: DNA
<213> ORGANISM: Artificial sequence
<220> FEATURE:
<223> OTHER INFORMATION: Synthetic sequence: Oligonucleotide
      NtMRP4Exon1FW

<400> SEQUENCE: 54
catctcctta cgaaggatac tacc                                           24
```

<210> SEQ ID NO 55
<211> LENGTH: 22
<212> TYPE: DNA
<213> ORGANISM: Artificial sequence
<220> FEATURE:
<223> OTHER INFORMATION: Synthetic sequence: Oligonucleotide NtMRP4Exon1REV

<400> SEQUENCE: 55
gctgcaagct ctcctttct aa                                              22

<210> SEQ ID NO 56
<211> LENGTH: 24
<212> TYPE: DNA
<213> ORGANISM: Artificial sequence
<220> FEATURE:
<223> OTHER INFORMATION: Synthetic sequence: Oligonucleotide NtMRP4Exon2FW

<400> SEQUENCE: 56
gtgcaatctg gcaaatatag tgag                                           24

<210> SEQ ID NO 57
<211> LENGTH: 24
<212> TYPE: DNA
<213> ORGANISM: Artificial sequence
<220> FEATURE:
<223> OTHER INFORMATION: Synthetic sequence: Oligonucleotide NtMRP4Exon2REV

<400> SEQUENCE: 57
aaaatgacat aggagcatgc agta                                           24

<210> SEQ ID NO 58
<211> LENGTH: 12
<212> TYPE: DNA
<213> ORGANISM: Nicotiana tabacum

<400> SEQUENCE: 58
gaagctggaa tg                                                        12

<210> SEQ ID NO 59
<211> LENGTH: 11
<212> TYPE: DNA
<213> ORGANISM: Nicotiana tabacum

<400> SEQUENCE: 59
attttaaaga g                                                         11

<210> SEQ ID NO 60
<211> LENGTH: 10
<212> TYPE: DNA
<213> ORGANISM: Nicotiana tabacum

<400> SEQUENCE: 60
gatcgacact                                                           10

<210> SEQ ID NO 61
<211> LENGTH: 11
<212> TYPE: DNA
<213> ORGANISM: Nicotiana tabacum

<400> SEQUENCE: 61
aggttgtcat g                                                         11

<210> SEQ ID NO 62
<211> LENGTH: 10
<212> TYPE: DNA
<213> ORGANISM: Nicotiana tabacum

<400> SEQUENCE: 62
tcagctagac                                                          10

<210> SEQ ID NO 63
<211> LENGTH: 10
<212> TYPE: DNA
<213> ORGANISM: Nicotiana tabacum

<400> SEQUENCE: 63
tgctcagcta                                                          10

<210> SEQ ID NO 64
<211> LENGTH: 11
<212> TYPE: DNA
<213> ORGANISM: Nicotiana tabacum

<400> SEQUENCE: 64
acaggctcat g                                                        11

<210> SEQ ID NO 65
<211> LENGTH: 10
<212> TYPE: DNA
<213> ORGANISM: Nicotiana tabacum

<400> SEQUENCE: 65
tgttggacag                                                          10

<210> SEQ ID NO 66
<211> LENGTH: 10
<212> TYPE: DNA
<213> ORGANISM: Nicotiana tabacum

<400> SEQUENCE: 66
caggctcatg                                                          10

<210> SEQ ID NO 67
<211> LENGTH: 12
<212> TYPE: DNA
<213> ORGANISM: Nicotiana tabacum

<400> SEQUENCE: 67
attgtaaatt at                                                       12

<210> SEQ ID NO 68
<211> LENGTH: 11
<212> TYPE: DNA
<213> ORGANISM: Nicotiana tabacum

<400> SEQUENCE: 68
ccgtagatgc t                                                        11

<210> SEQ ID NO 69
<211> LENGTH: 10
<212> TYPE: DNA
<213> ORGANISM: Nicotiana tabacum

<400> SEQUENCE: 69
agcagctttc                                                          10

<210> SEQ ID NO 70
<211> LENGTH: 10
<212> TYPE: DNA
<213> ORGANISM: Nicotiana tabacum

<400> SEQUENCE: 70
gcagctgtcc                                                              10

<210> SEQ ID NO 71
<211> LENGTH: 11
<212> TYPE: DNA
<213> ORGANISM: Nicotiana tabacum

<400> SEQUENCE: 71
atatgatgct a                                                            11

<210> SEQ ID NO 72
<211> LENGTH: 10
<212> TYPE: DNA
<213> ORGANISM: Nicotiana tabacum

<400> SEQUENCE: 72
gctacagcta                                                              10

<210> SEQ ID NO 73
<211> LENGTH: 10
<212> TYPE: DNA
<213> ORGANISM: Nicotiana tabacum

<400> SEQUENCE: 73
attccatttg                                                              10

<210> SEQ ID NO 74
<211> LENGTH: 11
<212> TYPE: DNA
<213> ORGANISM: Nicotiana tabacum

<400> SEQUENCE: 74
ctcatgccat t                                                            11

<210> SEQ ID NO 75
<211> LENGTH: 11
<212> TYPE: DNA
<213> ORGANISM: Nicotiana tabacum

<400> SEQUENCE: 75
tgccattgca a                                                            11

<210> SEQ ID NO 76
<211> LENGTH: 10
<212> TYPE: DNA
<213> ORGANISM: Nicotiana tabacum

<400> SEQUENCE: 76
tttctgtggc                                                              10

<210> SEQ ID NO 77
<211> LENGTH: 11
<212> TYPE: DNA
<213> ORGANISM: Nicotiana tabacum

<400> SEQUENCE: 77

```
ctttagccat c                                                    11

<210> SEQ ID NO 78
<211> LENGTH: 10
<212> TYPE: DNA
<213> ORGANISM: Nicotiana tabacum

<400> SEQUENCE: 78
tttatactta                                                      10

<210> SEQ ID NO 79
<211> LENGTH: 10
<212> TYPE: DNA
<213> ORGANISM: Nicotiana tabacum

<400> SEQUENCE: 79
ttcaactgtt                                                      10

<210> SEQ ID NO 80
<211> LENGTH: 10
<212> TYPE: DNA
<213> ORGANISM: Nicotiana tabacum

<400> SEQUENCE: 80
taacactagc                                                      10

<210> SEQ ID NO 81
<211> LENGTH: 10
<212> TYPE: DNA
<213> ORGANISM: Nicotiana tabacum

<400> SEQUENCE: 81
tggacttgca                                                      10

<210> SEQ ID NO 82
<211> LENGTH: 11
<212> TYPE: DNA
<213> ORGANISM: Nicotiana tabacum

<400> SEQUENCE: 82
cagtgatggt a                                                    11

<210> SEQ ID NO 83
<211> LENGTH: 11
<212> TYPE: DNA
<213> ORGANISM: Nicotiana tabacum

<400> SEQUENCE: 83
aggcaacaaa t                                                    11

<210> SEQ ID NO 84
<211> LENGTH: 10
<212> TYPE: DNA
<213> ORGANISM: Nicotiana tabacum

<400> SEQUENCE: 84
ttataaagtt                                                      10

<210> SEQ ID NO 85
<211> LENGTH: 10
<212> TYPE: DNA
<213> ORGANISM: Nicotiana tabacum

<400> SEQUENCE: 85
```
caggcatggg                                                                   10

<210> SEQ ID NO 86
<211> LENGTH: 11
<212> TYPE: DNA
<213> ORGANISM: Nicotiana tabacum

<400> SEQUENCE: 86
caggcatggg a                                                                 11

<210> SEQ ID NO 87
<211> LENGTH: 11
<212> TYPE: DNA
<213> ORGANISM: Nicotiana tabacum

<400> SEQUENCE: 87
attgaatctt t                                                                 11

<210> SEQ ID NO 88
<211> LENGTH: 11
<212> TYPE: DNA
<213> ORGANISM: Nicotiana tabacum

<400> SEQUENCE: 88
cgcgagtccg a                                                                 11

<210> SEQ ID NO 89
<211> LENGTH: 11
<212> TYPE: DNA
<213> ORGANISM: Nicotiana tabacum

<400> SEQUENCE: 89
aatctttccg c                                                                 11

<210> SEQ ID NO 90
<211> LENGTH: 10
<212> TYPE: DNA
<213> ORGANISM: Nicotiana tabacum

<400> SEQUENCE: 90
agtacggatg                                                                   10

<210> SEQ ID NO 91
<211> LENGTH: 11
<212> TYPE: DNA
<213> ORGANISM: Nicotiana tabacum

<400> SEQUENCE: 91
ttgtccaagt t                                                                 11

<210> SEQ ID NO 92
<211> LENGTH: 12
<212> TYPE: DNA
<213> ORGANISM: Nicotiana tabacum

<400> SEQUENCE: 92
agttcttgta ct                                                                12

<210> SEQ ID NO 93
<211> LENGTH: 10
<212> TYPE: DNA
<213> ORGANISM: Nicotiana tabacum

```
<400> SEQUENCE: 93
aatagctggt                                                          10

<210> SEQ ID NO 94
<211> LENGTH: 11
<212> TYPE: DNA
<213> ORGANISM: Nicotiana tabacum

<400> SEQUENCE: 94
cattgtcttg t                                                        11

<210> SEQ ID NO 95
<211> LENGTH: 10
<212> TYPE: DNA
<213> ORGANISM: Nicotiana tabacum

<400> SEQUENCE: 95
gagcactcct                                                          10

<210> SEQ ID NO 96
<211> LENGTH: 10
<212> TYPE: DNA
<213> ORGANISM: Nicotiana tabacum

<400> SEQUENCE: 96
ttgtcttgtg                                                          10

<210> SEQ ID NO 97
<211> LENGTH: 10
<212> TYPE: DNA
<213> ORGANISM: Nicotiana tabacum

<400> SEQUENCE: 97
agcactcctc                                                          10

<210> SEQ ID NO 98
<211> LENGTH: 10
<212> TYPE: DNA
<213> ORGANISM: Nicotiana tabacum

<400> SEQUENCE: 98
tggagcactc                                                          10

<210> SEQ ID NO 99
<211> LENGTH: 11
<212> TYPE: DNA
<213> ORGANISM: Nicotiana tabacum

<400> SEQUENCE: 99
tcttctagtt g                                                        11

<210> SEQ ID NO 100
<211> LENGTH: 11
<212> TYPE: DNA
<213> ORGANISM: Nicotiana tabacum

<400> SEQUENCE: 100
tacgctcact t                                                        11

<210> SEQ ID NO 101
<211> LENGTH: 10
<212> TYPE: DNA
<213> ORGANISM: Nicotiana tabacum
```

```
<400> SEQUENCE: 101
atcccgcttg                                                              10

<210> SEQ ID NO 102
<211> LENGTH: 10
<212> TYPE: DNA
<213> ORGANISM: Nicotiana tabacum

<400> SEQUENCE: 102
cgcaggaaca                                                              10

<210> SEQ ID NO 103
<211> LENGTH: 10
<212> TYPE: DNA
<213> ORGANISM: Nicotiana tabacum

<400> SEQUENCE: 103
gaaccgatca                                                              10

<210> SEQ ID NO 104
<211> LENGTH: 10
<212> TYPE: DNA
<213> ORGANISM: Nicotiana tabacum

<400> SEQUENCE: 104
ggcttccct                                                               10

<210> SEQ ID NO 105
<211> LENGTH: 10
<212> TYPE: DNA
<213> ORGANISM: Nicotiana tabacum

<400> SEQUENCE: 105
aaccgatcag                                                              10

<210> SEQ ID NO 106
<211> LENGTH: 10
<212> TYPE: DNA
<213> ORGANISM: Nicotiana tabacum

<400> SEQUENCE: 106
gctttccctc                                                              10

<210> SEQ ID NO 107
<211> LENGTH: 10
<212> TYPE: DNA
<213> ORGANISM: Nicotiana tabacum

<400> SEQUENCE: 107
catgatctca                                                              10

<210> SEQ ID NO 108
<211> LENGTH: 11
<212> TYPE: DNA
<213> ORGANISM: Nicotiana tabacum

<400> SEQUENCE: 108
tttcacaagc a                                                            11

<210> SEQ ID NO 109
<211> LENGTH: 11
<212> TYPE: DNA
```

```
<213> ORGANISM: Nicotiana tabacum

<400> SEQUENCE: 109
atctcttgat a                                                         11

<210> SEQ ID NO 110
<211> LENGTH: 11
<212> TYPE: DNA
<213> ORGANISM: Nicotiana tabacum

<400> SEQUENCE: 110
attggacaaa t                                                         11

<210> SEQ ID NO 111
<211> LENGTH: 11
<212> TYPE: DNA
<213> ORGANISM: Nicotiana tabacum

<400> SEQUENCE: 111
tattagaagc t                                                         11

<210> SEQ ID NO 112
<211> LENGTH: 11
<212> TYPE: DNA
<213> ORGANISM: Nicotiana tabacum

<400> SEQUENCE: 112
gaatggattt t                                                         11

<210> SEQ ID NO 113
<211> LENGTH: 10
<212> TYPE: DNA
<213> ORGANISM: Nicotiana tabacum

<400> SEQUENCE: 113
ttcaccgcga                                                           10

<210> SEQ ID NO 114
<211> LENGTH: 10
<212> TYPE: DNA
<213> ORGANISM: Nicotiana tabacum

<400> SEQUENCE: 114
atctctcttc                                                           10

<210> SEQ ID NO 115
<211> LENGTH: 11
<212> TYPE: DNA
<213> ORGANISM: Nicotiana tabacum

<400> SEQUENCE: 115
aaacaaccaa a                                                         11

<210> SEQ ID NO 116
<211> LENGTH: 10
<212> TYPE: DNA
<213> ORGANISM: Nicotiana tabacum

<400> SEQUENCE: 116
agagcaatgc                                                           10

<210> SEQ ID NO 117
<211> LENGTH: 11
```

```
<212> TYPE: DNA
<213> ORGANISM: Nicotiana tabacum

<400> SEQUENCE: 117
ccttgaagaa t                                                        11

<210> SEQ ID NO 118
<211> LENGTH: 11
<212> TYPE: DNA
<213> ORGANISM: Nicotiana tabacum

<400> SEQUENCE: 118
aaaatcttct c                                                        11

<210> SEQ ID NO 119
<211> LENGTH: 11
<212> TYPE: DNA
<213> ORGANISM: Nicotiana tabacum

<400> SEQUENCE: 119
agaatcaaaa t                                                        11

<210> SEQ ID NO 120
<211> LENGTH: 11
<212> TYPE: DNA
<213> ORGANISM: Nicotiana tabacum

<400> SEQUENCE: 120
ttctcgaaga t                                                        11

<210> SEQ ID NO 121
<211> LENGTH: 11
<212> TYPE: DNA
<213> ORGANISM: Nicotiana tabacum

<400> SEQUENCE: 121
tatctaagga a                                                        11

<210> SEQ ID NO 122
<211> LENGTH: 10
<212> TYPE: DNA
<213> ORGANISM: Nicotiana tabacum

<400> SEQUENCE: 122
aaaacggaga                                                          10

<210> SEQ ID NO 123
<211> LENGTH: 11
<212> TYPE: DNA
<213> ORGANISM: Nicotiana tabacum

<400> SEQUENCE: 123
tcaacagtct a                                                        11

<210> SEQ ID NO 124
<211> LENGTH: 10
<212> TYPE: DNA
<213> ORGANISM: Nicotiana tabacum

<400> SEQUENCE: 124
atctgatagg                                                          10

<210> SEQ ID NO 125
```

```
<211> LENGTH: 11
<212> TYPE: DNA
<213> ORGANISM: Nicotiana tabacum

<400> SEQUENCE: 125
gggattctaa a                                                             11

<210> SEQ ID NO 126
<211> LENGTH: 10
<212> TYPE: DNA
<213> ORGANISM: Nicotiana tabacum

<400> SEQUENCE: 126
acttataaag                                                               10

<210> SEQ ID NO 127
<211> LENGTH: 10
<212> TYPE: DNA
<213> ORGANISM: Nicotiana tabacum

<400> SEQUENCE: 127
aagaagaaag                                                               10

<210> SEQ ID NO 128
<211> LENGTH: 11
<212> TYPE: DNA
<213> ORGANISM: Nicotiana tabacum

<400> SEQUENCE: 128
aacttataaa g                                                             11

<210> SEQ ID NO 129
<211> LENGTH: 12
<212> TYPE: DNA
<213> ORGANISM: Nicotiana tabacum

<400> SEQUENCE: 129
aaagagaaac tg                                                            12

<210> SEQ ID NO 130
<211> LENGTH: 11
<212> TYPE: DNA
<213> ORGANISM: Nicotiana tabacum

<400> SEQUENCE: 130
gctatatatt a                                                             11

<210> SEQ ID NO 131
<211> LENGTH: 11
<212> TYPE: DNA
<213> ORGANISM: Nicotiana tabacum

<400> SEQUENCE: 131
tgaagctttt g                                                             11

<210> SEQ ID NO 132
<211> LENGTH: 10
<212> TYPE: DNA
<213> ORGANISM: Nicotiana tabacum

<400> SEQUENCE: 132
gaagcttttg                                                               10
```

```
<210> SEQ ID NO 133
<211> LENGTH: 10
<212> TYPE: DNA
<213> ORGANISM: Nicotiana tabacum

<400> SEQUENCE: 133
ttggatggtg                                                          10

<210> SEQ ID NO 134
<211> LENGTH: 11
<212> TYPE: DNA
<213> ORGANISM: Nicotiana tabacum

<400> SEQUENCE: 134
ggcgtagtgc t                                                        11

<210> SEQ ID NO 135
<211> LENGTH: 10
<212> TYPE: DNA
<213> ORGANISM: Nicotiana tabacum

<400> SEQUENCE: 135
ttgtggcaaa                                                          10

<210> SEQ ID NO 136
<211> LENGTH: 10
<212> TYPE: DNA
<213> ORGANISM: Nicotiana tabacum

<400> SEQUENCE: 136
ttctctaatg                                                          10

<210> SEQ ID NO 137
<211> LENGTH: 10
<212> TYPE: DNA
<213> ORGANISM: Nicotiana tabacum

<400> SEQUENCE: 137
gttctctaat                                                          10

<210> SEQ ID NO 138
<211> LENGTH: 10
<212> TYPE: DNA
<213> ORGANISM: Nicotiana tabacum

<400> SEQUENCE: 138
gcaaagttct                                                          10

<210> SEQ ID NO 139
<211> LENGTH: 10
<212> TYPE: DNA
<213> ORGANISM: Nicotiana tabacum

<400> SEQUENCE: 139
taatggcaag                                                          10

<210> SEQ ID NO 140
<211> LENGTH: 10
<212> TYPE: DNA
<213> ORGANISM: Nicotiana tabacum

<400> SEQUENCE: 140
catatgaaac                                                          10
```

<210> SEQ ID NO 141
<211> LENGTH: 10
<212> TYPE: DNA
<213> ORGANISM: Nicotiana tabacum

<400> SEQUENCE: 141
caacaaatga                                                              10

<210> SEQ ID NO 142
<211> LENGTH: 10
<212> TYPE: DNA
<213> ORGANISM: Nicotiana tabacum

<400> SEQUENCE: 142
atgcttaatt                                                              10

<210> SEQ ID NO 143
<211> LENGTH: 11
<212> TYPE: DNA
<213> ORGANISM: Nicotiana tabacum

<400> SEQUENCE: 143
cttcagcrga y                                                            11

<210> SEQ ID NO 144
<211> LENGTH: 12
<212> TYPE: DNA
<213> ORGANISM: Nicotiana tabacum

<400> SEQUENCE: 144
gtgccatgtc ct                                                           12

<210> SEQ ID NO 145
<211> LENGTH: 11
<212> TYPE: DNA
<213> ORGANISM: Nicotiana tabacum

<400> SEQUENCE: 145
tgtccttcaa t                                                            11

<210> SEQ ID NO 146
<211> LENGTH: 10
<212> TYPE: DNA
<213> ORGANISM: Nicotiana tabacum

<400> SEQUENCE: 146
cttctctgtt                                                              10

<210> SEQ ID NO 147
<211> LENGTH: 10
<212> TYPE: DNA
<213> ORGANISM: Nicotiana tabacum

<400> SEQUENCE: 147
ggcatgggaa                                                              10

<210> SEQ ID NO 148
<211> LENGTH: 10
<212> TYPE: DNA
<213> ORGANISM: Nicotiana tabacum

```
<400> SEQUENCE: 148
aacattttaa                                                                 10
```

HEAVY METAL REDUCTION IN PLANTA

This application is a U.S. National Stage Application of International Application No. PCT/EP2011/004383, filed Aug. 31, 2011, which was published in English on Mar. 8, 2012 as International Patent Publication WO 2012/028309 A2. International Application No. PCT/EP2011/004383 also claims priority to European Application No. 10009180.0, filed Sep. 3, 2010.

This application contains a Sequence Listing electronically submitted via EFS-Web to the United States Patent and Trademark Office as an ASCII text filed having a size of 134 kilobytes, entitled "U.S. Ser. No. 13/819,063_SubstituteSequenceListing-2_ST25.txt," and created on Dec. 22, 2014. The information contained in the Sequence Listing is incorporated by reference herein.

FIELD OF INVENTION

The present invention is directed to polynucleotides and polypeptides encoding ABC transporters that are involved in heavy metal transport. The present invention is also directed to modifying the expression of said polynucleotides or polypeptides in plants. In particular, the present invention relates to modulating (for example, reducing or inhibiting) the expression or activity of one or more ABC transporters involved in subcellular heavy metal transport.

INTRODUCTION

Plants obtain essential heavy metals—such as zinc and copper—by absorbing metal ion substrates from their environment by various transport mechanisms mediated by transmembrane transporters expressed on the surface of root cells and other vascular tissues. One mechanism utilises the transport of toxins out of the cytosol. For example, the glutathione S-conjugate (GS-X) pump family is one class of ATP-binding cassette (ABC) transporters that is responsible for the elimination/sequestration of compounds in plants as well as mammalian, yeast cells. The molecular structure and function of GS-X pumps encoded by mammalian and plant MRP, cMOAT (canalicular multispecific anion transporter), and YCF1 (yeast cadmium factor) genes appear to have conserved throughout molecular evolution.

Plants are exposed to exogenous toxins—such as microbial products, allelochemicals, agrochemicals and heavy metals—making cell survival dependent on mechanisms for detoxifying or reducing the accumulation of these agents. Heavy metals—such as lead, cadmium, mercury and so on—are major environmental toxicants, which cause reactive oxidation species generation, DNA damage, and enzyme inactivation by binding to active sites of enzymes in cells of living organisms. Contamination of the environment with heavy metals has increased drastically due to industrialization and increases in population size. Soils contaminated with heavy metals inhibit normal plant growth and cause contamination of food stuffs. Many heavy metals are very toxic to human health and carcinogenic at low concentrations.

The reduction in the content of heavy metals—such as cadmium—from plants or plant products consumed by animals and humans is highly desirable and urgently required. It is an object of the present invention to satisfy this need.

ASPECTS AND EMBODIMENTS OF THE INVENTION

Aspect and embodiments of the present invention are set forth in the accompanying claims.

In one aspect, there is provided an isolated polynucleotide selected from the group consisting of: an isolated polynucleotide comprising, consisting or consisting essentially of a sequence having at least 71% sequence identity to SEQ ID NO:1 or SEQ ID NO: 2 or SEQ ID NO:27 or SEQ ID NO: 28, SEQ ID NO: 29 or SEQ ID NO: 51; an isolated polynucleotide comprising, consisting or consisting essentially of a sequence having at least 65% sequence identity to any of SEQ ID NOs: 3 to 23 or 30 to 50 or 53; a polynucleotide encoding a NtMRP polypeptide comprising, consisting or consisting essentially of a sequence having at least 65% sequence identity to any of SEQ ID NOs: 24 to 26 or 52, and preferably, wherein the polypeptide has heavy metal transporter activity.

In a further aspect, there is provided a polynucleotide construct of at least 15 contiguous nucleotides in length that is at least 65% identical to a region of any of SEQ ID NOs: 1 to 23 or 27 to 51.

In a further aspect, there is provided a double-stranded ribopolynucleotide comprising at least two sequences that are at least partially complementary to each other and wherein a sense strand comprises a first sequence and an antisense strand comprises a second sequence and wherein at least one of the sequences comprises at least 10 contiguous nucleotides of NtMRP RNA.

Suitably, the double-stranded RNA comprises a first sequence having at least 65% sequence identity to at least 10 nucleotides of NtMRP DNA; a second sequence; and a third sequence having a reverse complementary sequence of the first sequence, positioned in the same orientation as the first sequence, wherein the second sequence is positioned between the first sequence and the third sequence, and the second sequence is operably-linked to the first sequence and to the third sequence.

Suitably, the first sequence has at least 65% sequence identity to a sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 SEQ ID NO:16, SEQ ID NO:17, SEQ ID NO:18, SEQ ID NO:19, SEQ ID NO:20, SEQ ID NO:21, SEQ ID NO:21, SEQ ID NO:22, SEQ ID No. 23, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NQ: 39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:53.

Suitably, the third sequence has at least 65% sequence identity to the reverse complement of the corresponding sequence to SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 SEQ ID NO:16, SEQ ID NO:17, SEQ ID NO:18, SEQ ID NO:19, SEQ ID NO:20, SEQ ID NO:21, SEQ ID NO:21, SEQ ID NO:22, SEQ ID No. 23, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO: 53.

In a further aspect, there is provided an expression vector comprising the isolated polynucleotide or the polynucleotide construct.

In a further aspect, there is provided a mutant, non-naturally occurring or transgenic plant cell to comprising the isolated polynucleotide, the polynucleotide construct, the double stranded ribopolynucleotide or the expression vector.

In a further aspect, there is provided a mutant, non-naturally occurring or transgenic plant comprising the mutant, non-naturally occurring or transgenic plant cell.

In a further aspect, there is provided plant material including biomass, seed or leaves comprising cells or tissue from said plant.

In a further aspect, there is provided a tobacco product comprising a part of said plant or plant cell or said plant material.

In a further aspect, there is provided a mutant, non-naturally occurring or transgenic plant, wherein expression of the NtMRP polynucleotide and the activity of the protein encoded thereby or the activity of the protein encoded thereby is decreased and the leaves of said plant have a reduction in cadmium content of at least 5% as compared to a control plant in which the expression of NtMRP polynucleotide and the activity of the protein encoded thereby or the activity of the protein encoded thereby has not decreased.

In a further aspect, there is provided biomass, seed or leaves comprising tissue from the plant. In a further aspect, there is provided a method for reducing cadmium levels in at least a part of a plant, comprising the step of reducing the expression of NtMRP polynucleotide and the activity of the protein encoded thereby or the activity of the protein encoded thereby as compared to a control plant in which the expression of NtMRP polynucleotide and the activity of the protein encoded thereby or the activity of the protein encoded thereby has not decreased.

In a further aspect, there is provided a mutant, non-naturally occurring or transgenic plant obtained or obtainable by the method described herein, wherein there is a reduction in cadmium content of at least about 5% in at least a part of the plant as compared to a control plant in which the expression of NtMRP polynucleotide and the activity of the protein encoded thereby or the activity of the protein encoded thereby has not decreased.

In a further aspect, there is provided an isolated NtMRP polypeptide expressed by the sequence set forth in any of SEQ ID NOs: 24 to 26 or SEQ ID NOs:52, preferably, wherein the polypeptide has heavy metal transporter activity.

In a further aspect, there is provided an antibody that specifically binds to the isolated polypeptide.

In a further aspect, there is provided a method of detecting a NtMRP polynucleotide in a sample comprising the step of: (a) providing a sample comprising a polynucleotide; (b) contacting said sample with one of more primers or one or more probes for specifically detecting at least a portion of NtMRP polynucleotide; and (c) detecting the presence of an amplification product, wherein the presence of an amplification product is indicative of the presence of the NtMRP polynucleotide in the sample.

Further aspects of the present invention are set forth below.

A chimeric gene comprising the isolated polynucleotide operably linked to one or more regulatory sequences.

A polynucleotide construct or a double-stranded RNA according to the present invention, wherein the polynucleotide comprises, consists or consists essentially of at least 15-30 nucleotides, 30-50 nucleotides, 50-100 nucleotides, 100-150 nucleotides, 150-200 nucleotides, 200-300 nucleotides, 300-400 nucleotides, 400-500 nucleotides, 500-600 nucleotides or 600-700 nucleotides.

A conjugate comprising the isolated polynucleotide the chimeric gene, the polynucleotide construct, or the double-stranded RNA according to the present invention and at least one non-nucleotide or non-polynucleotide moiety covalently attached thereto.

A mutant, non-naturally occurring or transgenic plant cell comprising the isolated polynucleotide, the chimeric gene, the polynucleotide construct, the double-stranded RNA, the conjugate or the expression vector according to the present invention.

A mutant, non-naturally occurring or transgenic plant comprising the mutant, non-naturally occurring or transgenic plant cell according to the present invention.

Suitably, the dry biomass of collected leaves is about the same as the control plant. Biomass, seed or leaves comprising tissue from the plant of the present invention.

A consumable product incorporating or utilising biomass, seed or leaves according to the present invention.

Biomass, seed or leaves according to the present invention or a consumable product according to the present invention, wherein there is a reduction in cadmium content of at least about 5% therein as compared to the biomass, seed or leaves from a control plant in which the expression of NtMRP polynucleotide and the activity of the protein encoded thereby or the activity of the protein encoded thereby has not decreased.

A cell line comprising the isolated polynucleotide, the chimeric gene, the polynucleotide construct, the double-stranded RNA, the conjugate or the expression vector according to the present invention.

A method for preparing a mutant, non-naturally occurring or transgenic plant comprising the step of reducing the expression of NtMRP polynucleotide and the activity of the protein encoded thereby or the activity of the protein encoded thereby in at least a part of said plant as compared to a control plant in which the expression of NtMRP polynucleotide and the activity of the protein encoded thereby or the activity of the protein encoded thereby has not decreased.

A method for reducing cadmium levels in at least a part of a plant, comprising the step of reducing the expression of NtMRP polynucleotide and the activity of the protein encoded thereby or the activity of the protein encoded thereby as compared to a control plant in which the expression of NtMRP polynucleotide and the activity of the protein encoded thereby or the activity of the protein encoded thereby has not decreased.

Suitably, said method comprises the first step of contacting said plant with the polynucleotide construct, the double-stranded RNA, the conjugate, the expression vector, a meganuclease, or a zinc finger protein.

Suitably, said method comprises the first or additional step of contacting said plant with a mutagen.

A mutant, non-naturally occurring or transgenic plant obtained or obtainable by the methods of the present invention, wherein there is a reduction in cadmium content of at least about 5% in at least a part of the plant as compared to a control plant in which the expression of NtMRP polynucleotide and the activity of the protein encoded thereby or the activity of the protein encoded thereby has not decreased.

A method for modulating (for example, reducing or inhibiting) the expression of NtMRP polynucleotide or the activity of the protein encoded thereby in a cell, said method comprising administering the chimeric gene, the polynucleotide construct, the double-stranded RNA, the conjugate or the expression vector according to the present invention.

A method for detecting, isolating, amplifying or analysing NtMRP polynucleotide, the method comprising the step of providing a sample comprising polynucleotide and hybridising said polynucleotide to a polynucleotide molecule comprising a nucleotide sequence of at least 10 contiguous nucleotides from the isolated nucleotide sequence according to the present invention.

Use of agent that modulate (for example, reduces or inhibits) the expression of NtMRP polynucleotide and the activity of the protein encoded thereby or the activity of the protein encoded thereby for reducing the cadmium content in at least a part of a plant by at least 5% as compared to a control plant in which the expression of NtMRP polynucleotide and the activity of the protein encoded thereby or the activity of the protein encoded thereby has not decreased. The method or the use according to the present invention, wherein the agent is or is derived from NtMRP polynucleotide, a chimeric NtMRP gene, a polynucleotide construct comprising NtMRP polynucleotide, an antisense RNA, a double-stranded RNA, a cDNA, a conjugate comprising NtMRP polynucleotide and at least one non-nucleotide or non-polynucleotide moiety covalently attached thereto, a ribozyme, a mutagen, a zinc finger, a small molecule or a meganuclease.

In a further aspect, there is provided a method of producing a tobacco product comprising the steps of: (a) obtaining seed from the mutant, non-naturally occurring or transgenic tobacco plant; (b) planting and growing the seed into a plant; (c) harvesting the plant; and (d) preparing a tobacco product from the harvested plant.

The above-mentioned embodiments are disclosed as embodiments of each of the aspects described above.

Some Advantages

Producing mutant, non-naturally occurring or transgenic plants (including biomass, seed and leaves obtained therefrom) in which lower amounts of cadmium are present provides a number of advantages.

By way of example, the plants, including mutant, non-naturally occurring or transgenic plants, can be grown in soils containing variable cadmium concentrations, or in soils containing less than desirable cadmium concentrations. These plants and derivative seeds can provide more options for cultivating them in a broader range of soil environments, which may increase the amount of cultivatable soils available to practitioners (for example, farmers).

By way of further example, the mutant, non-naturally occurring or plants (including biomass, seed and leaves obtained therefrom) exhibit reduced cadmium content, compared to control counterparts and may be consumed directly as edible products. The consumption of these edible products may be a healthier option. Suitable plants that can be manipulated according to the disclosed methods include plants cultivatable for agricultural use, including tobacco, rice, corn, squash, soybeans, lettuce, potatoes, beats, herbs, wheat, barley and carrots, etc.

By way of further example, the height and/or weight of the mutant, non-naturally occurring or transgenic plants is substantially the same as the control plants. Thus, no significant differences are found in dried collected leaves of the plants as compared to a control thus indicating that the modulation of NtMRP transcripts has no statistically relevant effect on dry biomass. This is advantageous because plants are used for the commercial production of various products including tobacco where alterations in visual appearance would either not be acceptable to the industry or could result in unacceptably reduced production yields.

BRIEF DESCRIPTION OF THE FIGURES

FIG. 1(a) is a schematic diagram of the NtMRP4 locus; FIG. 1(b) shows the nucleotide sequence of NtMRP4 (SEQ ID NO:1) in which the 5' and 3' UTR regions are underlined; exons are shown in capital and bold letters; introns are shown in lower-case and normal letter; and start and stop codons are shown in grey. The 5' and 3' primers sequences for the generation of a NtMRP4 RNAi sequence are indicated in italic and strikethrough.

FIG. 6 shows the nucleotide sequence of NtMRP3 (SEQ ID NO:28) in which the 5' and 3' UTR regions are italicised; exons are shown in capital and bold letters; introns are shown in lower-case and normal letter; and start and stop codons are shown in capital, bold and italicised letters.

DEFINITIONS

Figure 1:
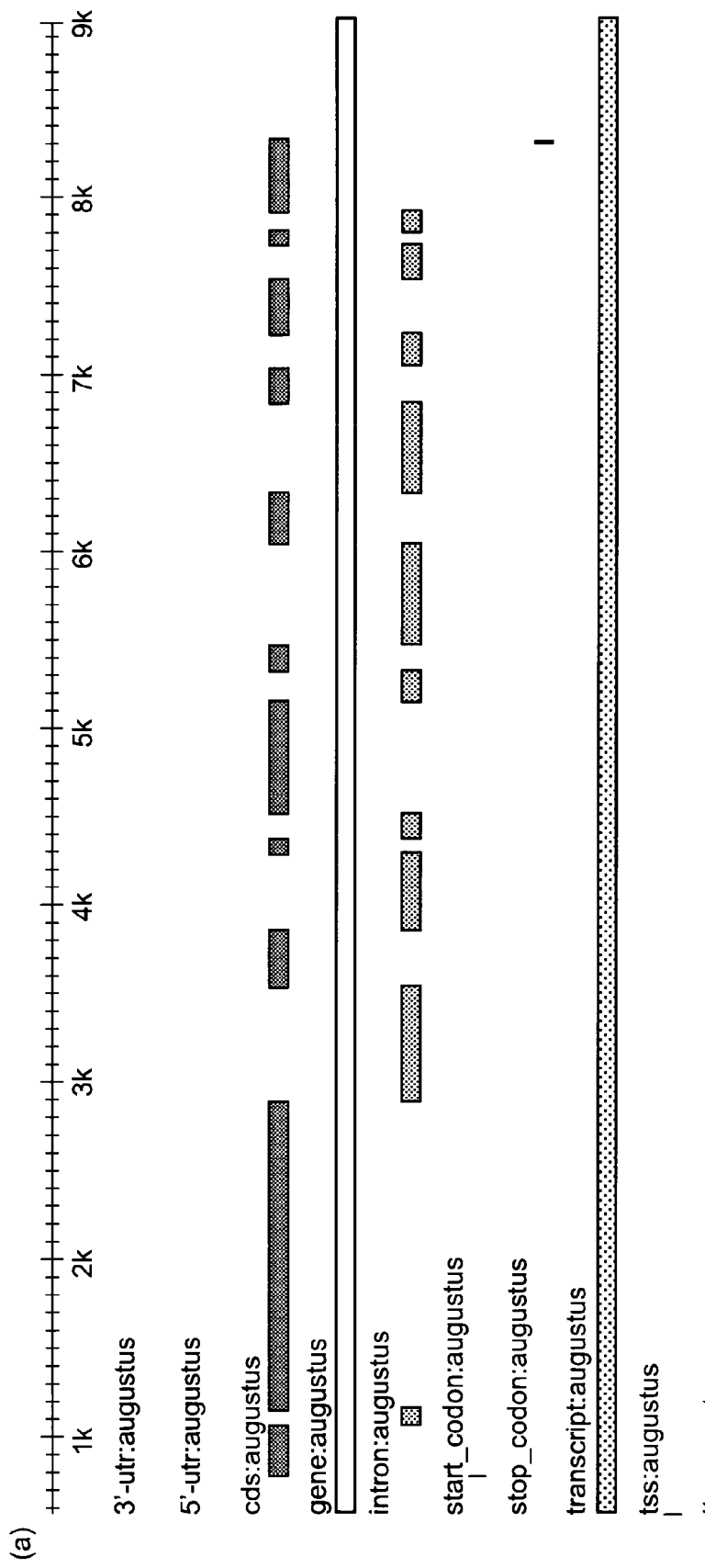
FIG. 1.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. The term "about" in the context of a given numerate value or range refers to a value or range that is within 20%, within 10%, or within 5%, 4%, 3%, 2% or 1% of the given value or range. A 'polynucleotide' refers to a polymer of nucleotides, which may be unmodified or modified deoxyribopolynucleotide (DNA) or ribopolynucleotide (RNA). Accordingly, a polynucleotide can be, without limitation, a genomic DNA, complementary DNA (cDNA) (for example, SEQ ID No. 27), mRNA, or antisense RNA. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions. In addition, the polynucleotide can be composed of triple-stranded regions comprising DNA, RNA, or both. A polynucleotide can contain one or more modified bases, such as phosphothioates, and can be a peptide polynucleotide (PNA). Generally, polynucleotides described herein can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

The term 'NtMRP polynucleotide' encompasses polynucleotides in which a polymer of nucleotides comprises, consists or consists essentially of the sequence set forth in SEQ ID NOs: 1, 2, 27, 28, 29 or 51. This term also encompasses a polynucleotide sequence with substantial homology (that is, sequence similarity) or substantial identity to SEQ ID NOs: 1, 2, 27, 28, 29 or 51; fragments of SEQ ID NOs: 1, 2, 27, 28, 29 or 51; and fragments of SEQ ID NOs: 1, 2, 27, 28, 29 or 51 with substantial homology (that is, sequence similarity) or substantial identity thereto. The variant may have at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98% or 99% sequence identity to the sequence of the isolated NtMRP gene—such as the NtMRP3 gene or the NtMRP4 gene. Although the NtMRP polynucleotide sequences described herein are shown as DNA sequences, the sequences include their corresponding RNA sequences, and their complementary (for example, completely complementary) DNA or RNA sequences, including the reverse complement(s) thereof and antisense DNA or RNA sequences. Exemplary fragments are set forth in SEQ ID NOs: 3 to 23 and 30 to 50 and 53.

The term "NtMRP3 polynucleotide" refers to an embodiment in which a polymer of nucleotides comprises, consists or consists essentially of a polynucleotide designated herein as SEQ ID NO: 28 or SEQ ID NO: 29 or SEQ ID NO:51. The term encompasses polynucleotide variants with substantial homology (that is, sequence similarity) or substantial identity to SEQ ID NO:28 or SEQ ID NO:29 or SEQ ID NO:51; fragments of SEQ ID NO: 28 or SEQ ID NO: 29 or SEQ ID NO:51; and fragments of SEQ ID NO: 28 or SEQ ID NO: 29 or SEQ ID NO:51 with substantial homology (that is, sequence similarity) or substantial identity thereto. As described herein, the variant may have at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98% or 99% sequence identity to the sequence of the isolated NtMRP3 gene. Exemplary fragments are set forth in SEQ ID NOs: 30 to 50.

The term "NtMRP4 polynucleotide" refers to an embodiment in which a polymer of nucleotides comprises, consists or consists essentially of a polynucleotide designated herein as SEQ ID NO: 1 or SEQ ID NO: 2 or SEQ ID NO: 27. The term encompasses polynucleotide variants with substantial homology (that is, sequence similarity) or substantial identity to SEQ ID NO:1 or SEQ ID NO:2 or SEQ ID NO: 27; fragments of SEQ ID NO:1 or SEQ ID NO:2 or SEQ ID NO: 27; and fragments of SEQ ID NO: 1 or SEQ ID NO: 2 or SEQ ID NO.: 27 with substantial homology (that is, sequence similarity) or substantial identity thereto. The variant may have at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98% or 99% sequence identity to the sequence of the isolated NtMRP3 gene. Exemplary fragments are set forth in SEQ ID NOs: 3 to 23 and 53. The term "NtMRP polypeptide" refers to a polypeptide comprising, consisting or consisting essentially of an amino acid sequence that has substantial homology (that is, sequence similarity) or substantial identity to SEQ ID NOs: 24 to 26 and 52; fragments of SEQ ID NOs: 24 to 26 and 52; and fragments of SEQ ID NOs: 24 to 26 and 52 with substantial homology (that is, sequence similarity) or substantial identity thereto. The NtMRP polypeptides include fragments and sequences comprising a sufficient or substantial degree of identity or similarity to SEQ ID NOs: 24 to 26 and 52 that can function by transporting heavy metals (for example, cadmium) across cell membranes. NtMRP polypeptides also include variants or mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. NtMRP polypeptides may be in linear form or cyclized using known methods. The variant may have at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98% or 99% identity to the sequence of the NtMRP4 polypeptide.

The term "NtMRP3 polypeptide" refers to an embodiment in which the polypeptide comprises, consists or consists essentially of the sequence set forth in SEQ ID NOs: 52 or to a polypeptide comprising, consisting or consisting essentially of an amino acid sequence with substantial homology (that is, sequence similarity) or substantial identity to NOs: 52; fragments of SEQ ID NO:52; and fragments of SEQ ID NO: 52 with substantial homology (that is, sequence similarity) or substantial identity thereto. The NtMRP3 polypeptides include fragments and sequences comprising a sufficient or substantial degree of identity or similarity to SEQ ID NO: 52 that can function by transporting heavy metals (for example, cadmium) across cell membranes. NtMRP3 polypeptides also include variants or mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. NtMRP3 polypeptides may be in linear form or cyclized using known methods. As described herein, the variant may have at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98%, or 99% identity to the sequence of the NtMRP3 polypeptide.

The term "NtMRP4 polypeptide" refers to an embodiment in which the polypeptide comprises, consists or consists essentially of the sequence set forth in SEQ ID NO: 24, SEQ ID NO: 25, or SEQ ID NO: 26 or to a polypeptide comprising, consisting or consisting essentially of an amino acid sequence with substantial homology (that is, sequence similarity) or substantial identity to SEQ ID NO: 24, SEQ ID NO: 25, or SEQ ID NO: 26; fragments of SEQ ID NO: 24, SEQ ID NO: 25, or SEQ ID NO: 26; and fragments of SEQ ID NO: 24, SEQ ID NO: 25, or SEQ ID NO: 26 with substantial homology (that is, sequence similarity) or substantial identity thereto. The NtMRP4 polypeptides include fragments and sequences comprising a sufficient or substantial degree of identity or similarity to SEQ ID NO: 24, SEQ ID NO: 25, or SEQ ID NO: 26 that can function by transporting heavy metals (for example, cadmium) across cell membranes. NtMRP4 polypeptides also include variants or mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. NtMRP4 polypeptides may be in linear form or cyclized using known methods. As described herein, the variant may have at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98%, or 99% identity to the sequence of the NtMRP4 polypeptide.

The term 'isolated' means an entity that is taken from its natural milieu, but the term does not connote any degree of purification.

'Gene sequence' refers to the nucleotide sequence of a polynucleotide molecule or polynucleotide that encodes a polypeptide or a biologically active RNA, and encompasses the nucleotide sequence of a partial coding sequence that only encodes a fragment of a protein. The term 'vector' refers to a polynucleotide vehicle that comprises a combination of polynucleotide components for enabling the transport of polynucleotide, polynucleotide constructs and polynucleotide conjugates and the like. Suitable vectors include episomes capable of extra-chromosomal replication such as circular, double-stranded polynucleotide plasmids; linearized double-stranded polynucleotide plasmids; and other vectors of any origin. 'Expression vector' refers to a polynucleotide vehicle that comprises a combination of polynucleotide components for enabling the expression of polynucleotide, polynucleotide constructs and polynucleotide conjugates and the like. Suitable expression vectors include episomes capable of extra-chromosomal replication such as circular, double-stranded polynucleotide plasmids; linearized double-stranded polynucleotide plasmids; and other functionally equivalent expression vectors of any origin. An expression vector comprises at least a promoter positioned upstream and operably-linked to a polynucleotide, polynucleotide constructs or polynucleotide conjugate, as defined below.

A 'construct' refers to a double-stranded, recombinant polynucleotide fragment comprising one or more NtMRP polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

The term "conjugate" refers to a compound formed by the covalent attachment ("conjugation") of a polynucleotide to one or more moieties that are not themselves polynucleotides or monomers ("conjugated moieties").

'Template strand' refers to the strand comprising a sequence that complements that of the "sense or coding strand" of a polynucleotide duplex, such as a NtMRP genomic fragment, NtMRP cDNA, or NtMRP construct, or any polynucleotide fragment comprising a polynucleotide sequence that can be transcribed by RNA polymerase. During transcription, RNA polymerase can translocate along the template strand in the 3'-to-5' direction during nascent RNA synthesis. 'Sense strand' is used interchangeably herein with the term "coding strand" refers to the strand comprising a sequence that complements that of the template strand in a DNA duplex. For example, the sequence of the sense strand ("sense sequence") for the identified NtMRP genomic clone is designated as SEQ ID NO:1 or SEQ ID NO:2. For example, if the sense strand comprises a hypothetical sequence 5'-TAATCCGGT-3', then the substantially identical corresponding sequence within a hypothetical target mRNA is 5'-UAAUCCGGU-3'.

'Reverse complementary sequence' refers to the sequence that complements the "sense sequence" of interest (for example, exon sequence) positioned within the same strand, in the same orientation with respect to the sense sequence. For example, if a strand comprises a hypothetical sequence 5'-TAATCCGGT-3', then the reverse complementary sequence 5'-ACCGGATTA-3' may be operably-linked to the sense sequence, separated by a spacer sequence.

'NtMRP', 'NtMRP3' or 'NtMRP4 RNA transcript' includes polyribopolynucleotide molecules produced within a host plant cell of interest, resulting from the transcription of the endogenous NtMRP3 or NtMRP4 gene or cDNA as described herein. Thus, this term includes any RNA species or RNA variants produced as transcriptional products from NtMRP3 or NtMRP4 or NtMRP3 or NtMRP4 RNA including those RNA species or RNA variants that have sufficient similarity at structural/functional levels. For example, Nt MRP3 or NtMRP3 RNA transcripts include, but are not limited to: (1) pre-mRNAs and mRNAs produced from the transcription of the isolated NtMRP3 or NtMRP3 gene or cDNA; (2) pre-mRNAs and mRNAs produced from the transcription of any genes having at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98%, 99% or 100% sequence identity to the sequence of the isolated NtMRP3 gene (that is, other distinct genes substantially identical to the identified NtMRP3 gene and encoding related isoforms of ABC transporters); and (3) pre-mRNAs and mRNAs produced from the transcription of alleles of the NtMRP3 gene. The NtMRP3 RNA transcripts include RNA variants produced as a result of alternative RNA splicing reactions of heteronuclear RNAs ("hnRNAs") of a particular gene, mRNA variants resulting from such alternative RNA splicing reactions, and any intermediate RNA variants By way of further example, NtMRP4 or NtMRP4 RNA transcripts include: (1) pre-mRNAs and mRNAs produced from the transcription of the isolated NtMRP4 or NtMRP4 gene or cDNA, as described herein; (2) pre-mRNAs and mRNAs produced from the transcription of any genes having at least 60%, 61%, 62%, 63%, 64%, 65%, 66%, 67%, 68%, 69%, 70%, 71%, 72%, 73%, 74%, 75%, 80%, 85%, 90%, 95%, 96%, 97%, 98%, 99% or 100% or more sequence identity to the sequence of the isolated NtMRP4 gene (that is, other distinct genes substantially identical to the identified NtMRP4 gene and encoding related isoforms of ABC transporters); and (3) pre-mRNAs and mRNAs produced from the transcription of alleles of the NtMRP or NtMRP4 gene. The NtMRP and NtMRP4 RNA transcripts include RNA variants produced as a result of alternative RNA splicing reactions of heteronuclear RNAs ("hnRNAs") of a particular gene, mRNA variants resulting from such alternative RNA splicing reactions, and any intermediate RNA variants.

'Homology', 'identity' or 'similarity' refers to the degree of sequence similarity between two polypeptides or between two polynucleotide molecules compared by sequence alignment. The degree of homology between two discrete polynucleotide sequences being compared is a function of the number of identical, or matching, nucleotides at comparable positions. The degree of similarity expressed in terms of percent identity may be determined by visual inspection and mathematical calculation. Alternatively, the percent identity of two polynucleotide sequences may be determined by comparing sequence information using the GAP computer program, version 6.0 described by Devereux et a/. (*Nucl. Acids Res.* 12:387, 1984) and available from the University of Wisconsin Genetics Computer Group (UWGCG), ClustaiW, BLAST® (the Basic Local Alignment Search Tool), FASTA or Smith-Waterman. Typical default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Various programs known to persons skilled in the art of sequence comparison can be alternatively utilized.

The term "upstream" refers to a relative direction/position with respect to a reference element along a linear polynucleotide sequence, which indicates a direction/position towards the 5' end of the polynucleotide sequence. "Upstream" may be used interchangeably with the "5' end of a reference element."

'Operably-linked' refers to the joining of distinct polynucleotide elements, fragments, or sequences to produce a functional transcriptional unit or a functional expression vector. A 'promoter' refers to a polynucleotide element/sequence, typically positioned upstream and operably-linked to a double-stranded DNA fragment—such as a NtMRP RNAi construct. For example, a suitable promoter enables the transcriptional activation of a NtMRP RNAi construct by recruiting the transcriptional complex, including the RNA polymerase and various factors, to initiate RNA synthesis. Promoters can be derived entirely from regions proximate to a native gene of interest, or can be composed of different elements derived from different native promoters or synthetic DNA segments.

An 'enhancer' refers to a polynucleotide molecule, or a polynucleotide sequence, that can recruit transcriptional regulatory proteins such as transcriptional activators, to enhance transcriptional activation by increasing promoter activity. Suitable enhancers can be derived from regions proximate to a native promoter of interest (homologous sources) or can be derived from non-native contexts (heterologous sources) and operably-linked to any promoter of interest within NtMRP constructs—such as RNAi expression vectors—to enhance the activity or the tissue-specificity of a promoter. Some enhancers can operate in any orientation with respect to the orientation of a transcription unit. For example, enhancers may be positioned upstream or downstream of a transcriptional unit comprising a promoter and a NtMRP construct.

As used herein, the term 'plant' refers to any plant at any stage of its life cycle or development, and its progenies. In one embodiment, the plant is a tobacco plant, which refers to a plant belonging to the genus *Nicotiana*. Preferred species, cultivars, hybrids, and varieties of tobacco plant are described herein.

The term 'plant cell' refers to a structural and physiological unit of a plant. The plant cell may be in form of a protoplast without a cell wall, an isolated single cell or a cultured cell, or as a part of higher organized unit such as but not limited to, plant tissue, a plant organ, or a whole plant. 'Plant material' refers to any solid, liquid or gaseous composition, or a combination thereof, obtainable from a plant, including biomass, leaves, leaf lamina, midrib, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" denotes a group of plants that are used during plant breeding. A line is distinguishable from a variety as it displays little variation between individuals for one or more traits of interest, although there may be some variation between individuals for other traits. The term "reduce" or "reduced" refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100%, 200% or 300% or more of a quantity or an activity, such as but not limited to polypeptide activity, transcriptional activity, and/or protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity, and/or protein expression.

The term "increase" or "increased" refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100%, 200% or 300% or more of a quantity or an activity, such as but not limited to polypeptide activity, transcriptional activity, and/or protein expression.

The term "control" in the context of a control plant or control plant cells means a plant or plant cells in which expression or activity of a particular gene or protein—such as NtMRP—has not been modified (for example, increased or reduced) and so it can provide a comparison with a plant in which the expression or activity of a particular gene or protein—such as NtMRP—has been modified. The control plant may comprise an empty vector. The control plant may correspond to a wild-type plant.

DETAILED DESCRIPTION

Figure 6:
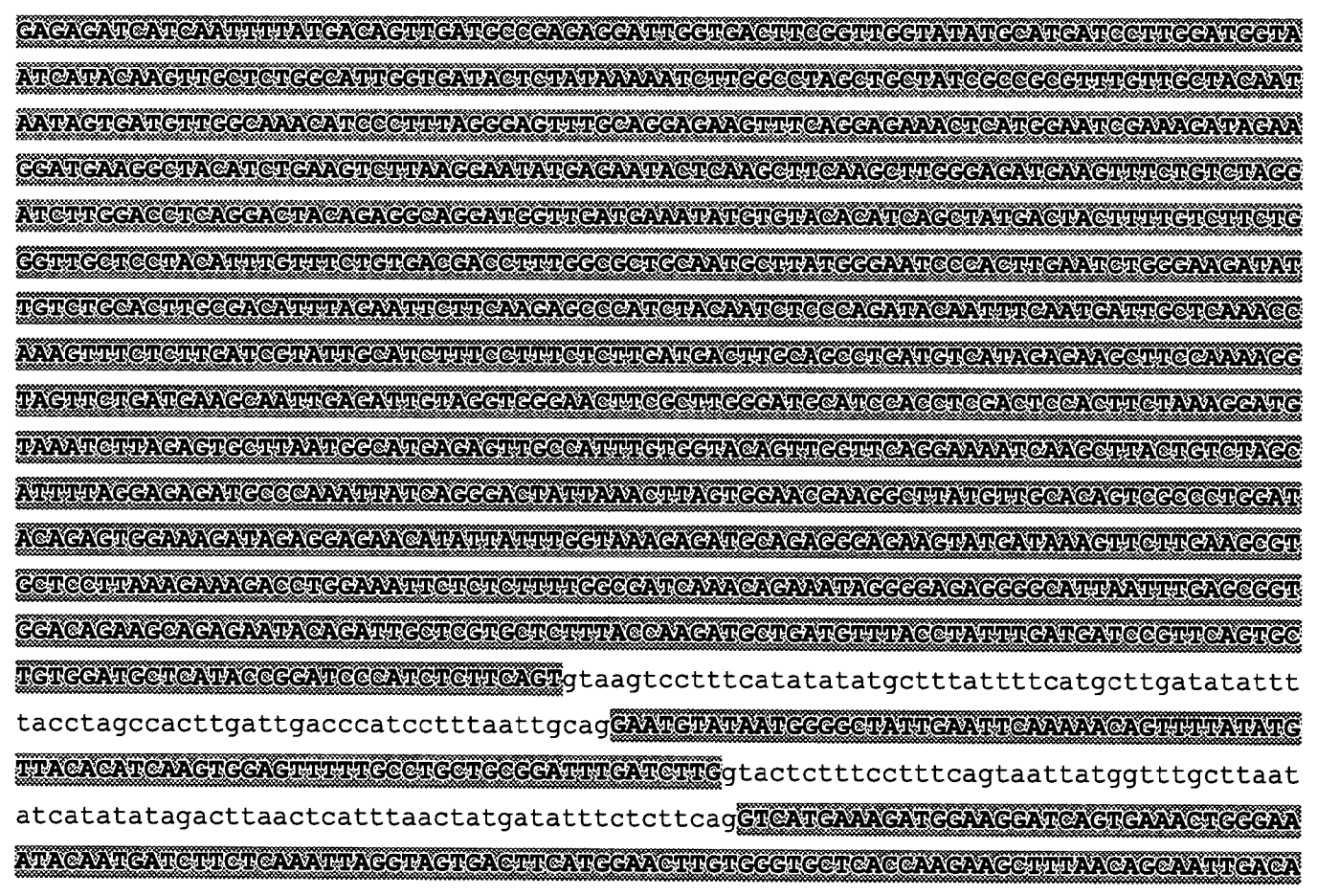
Figure 6:
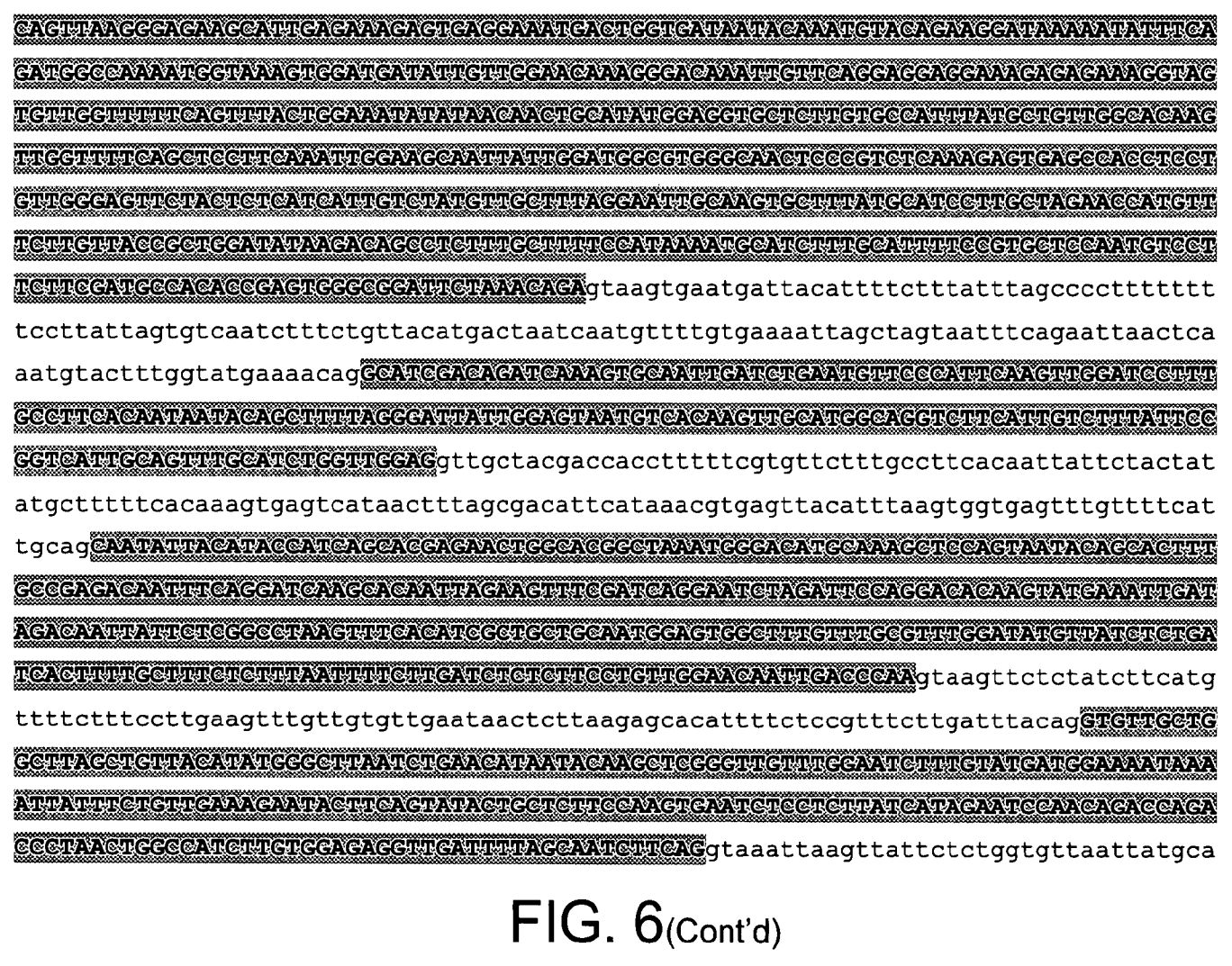

NtMRP polynucleotides and polypeptides are described herein including NtMRP3 and NtMRP4 polynucleotides and polypeptides. As shown in FIG. 6, the NtMRP3 genomic clone, designated as SEQ ID NO: 28 or SEQ ID NO: 29 comprises: intron 1 (SEQ ID NO:30), intron 2 (SEQ ID NO:31), intron 3 (SEQ ID NO:32), intron 4 (SEQ ID NO:33), intron 5 (SEQ ID NO:34), intron 6 (SEQ ID NO:35), intron 7 (SEQ ID NO:36), intron 8 (SEQ ID NO:37), intron 9 (SEQ ID NO:38), intron 10 (SEQ ID NO:39), exon 1 (SEQ ID NO:40), exon 2 (SEQ ID NO:41), exon 3 (SEQ ID NO:42) exon 4 (SEQ ID NO:43), exon 5 (SEQ ID NO:44), exon 6 (SEQ ID NO:45) exon 7 (SEQ ID NO:46) exon 8 (SEQ ID NO:47), exon 9 (SEQ ID NO:48) exon 10 (SEQ ID NO:49) and exon 11 (SEQ ID NO:50).

Various embodiments are directed to isolated polynucleotides representing genomic fragments isolated at the NtMRP3 locus, comprising SEQ ID NO:28 or SEQ ID NO:29, fragments of SEQ ID NO:28 or SEQ ID NO:29, or variants thereof.

Various embodiments are directed to isolated polynucleotides representing cDNA sequences of the NtMRP3 locus, comprising SEQ ID NO:51, fragments of SEQ ID NO:51, or variants thereof. Various embodiments are directed to isolated NtMRP polynucleotide variants comprising at least 71%, 72%, 73%, 74%, 75%, 80%, 85%, 90%, 95%, 96%, 97%, 98%, and 99% sequence so identity to SEQ ID NO:28 or SEQ ID NO:29, or fragments of SEQ ID NO:28 or SEQ ID NO:29. Various embodiments are directed to isolated polynucleotides that complement that of NtMRP polynucleotide variants comprising at least 71%, 72%, 73%, 74% 75%, 80%, 85%, 90%, 95%, 96%, 97%, 98%, and 99% sequence identity to SEQ ID NO:28 or SEQ ID NO:29 or SEQ ID NO: 51 or fragments of SEQ ID NO:28 or SEQ ID NO:29 or SEQ ID NO: 51.

Various embodiments are directed to isolated polynucleotides that can specifically hybridize, under moderate to highly stringent conditions, to polynucleotides comprising SEQ ID NO:28 or SEQ ID NO:29 or SEQ ID NO: 51, or fragments of SEQ ID NO:28 or SEQ ID NO:29 or SEQ ID NO: 51.

As shown in FIG. 1, the NtMRP4 genomic clone, designated as SEQ ID NO:1 or SEQ ID NO:2 comprises: intron 1 (SEQ ID NO:3), intron 2 (SEQ ID NO:4), intron 3 (SEQ ID NO:5), intron 4 (SEQ ID NO:6), intron 5 (SEQ ID NO:7), intron 6 (SEQ ID NO:8), intron 7 (SEQ ID NO:9), intron 8 (SEQ ID NO:10), intron 9 (SEQ ID NO:11), intron 10 (SEQ ID NO:12), exon 1 (SEQ ID NO:13), exon 2 (SEQ ID NO:14), exon 3 (SEQ ID NO:15) exon 4 (SEQ ID NO:16), exon 5 (SEQ ID NO:17), exon 6 (SEQ ID NO:18) exon 7 (SEQ ID NO:19) exon 8 (SEQ ID NO:20), exon 9 (SEQ ID NO:21) exon 10 (SEQ ID NO:22) and exon 11 (SEQ ID NO:53) or SEQ ID No. 23.

Various embodiments are directed to isolated polynucleotides representing genomic fragments isolated at the NtMRP4 locus, comprising SEQ ID NO:1 or SEQ ID NO:2, fragments of SEQ ID NO:1 or SEQ ID NO:2, or variants thereof.

Various embodiments are directed to isolated cDNA comprising SEQ ID NO:27, fragments of SEQ ID NO:27, or variants thereof.

Various embodiments are directed to isolated NtMRP polynucleotide variants comprising at least 71%, 72%, 73%, 74%, 75%, 80%, 85%, 90%, 95%, 96%, 97%, 98%, and 99% sequence identity to SEQ ID NO:1 or SEQ ID NO:2 or SEQ ID No. 27, or fragments of SEQ ID NO:1 or SEQ ID NO:2 or SEQ ID No. 27.

Various embodiments are directed to isolated polynucleotides that complement NtMRP polynucleotide variants comprising at least 71%, 72%, 73%, 74% 75%, 80%, 85%, 90%, 95%, 96%, 97%, 98%, and 99% sequence identity to SEQ ID NO:1 or SEQ ID NO:2 or SEQ ID NO:27 or fragments of SEQ ID NO:1 or SEQ ID NO:2 or SEQ ID NO:27.

Various embodiments are directed to isolated polynucleotides that can specifically hybridize, under moderate to highly stringent conditions, to polynucleotides comprising SEQ ID NO:1 or SEQ ID NO:2 or SEQ ID NO:27, or fragments of SEQ ID NO:1 or SEQ ID NO:2 or SEQ ID NO:27.

A polynucleotide as described herein will generally contain phosphodiester bonds, although in some cases, polynucleotide analogs are included that may have alternate backbones, comprising, for example, phosphoramidate, phosphorothioate, phosphorodithioate, or O-methylphophoroa midite linkages; and peptide polynucleotide backbones and linkages. Other analog polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogs can be made; alternatively, mixtures of different polynucleotide analogs, and mixtures of naturally occurring polynucleotides and analogs may be made.

A variety of polynucleotide analogs are known, including, for example, phosphoramidate, phosphorothioate, phosphorodithioate, O-methylphophoroamidite linkages and peptide polynucleotide backbones and linkages; Other analog polynucleotides include those with positive backbones, non-ionic backbones and non-ribose backbones. Polynucleotides containing one or more carbocyclic sugars are also included.

Other analogs include peptide polynucleotide (PNA) which are peptide polynucleotide analogs. These backbones are substantially non-ionic under neutral conditions, in contrast to the highly charged phosphodiester backbone of naturally occurring polynucleotides. This may result in advantages. First, the PNA backbone may exhibit improved hybridization kinetics. PNAs have larger changes in the melting temperature (Tm) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs may not be degraded or degraded to a lesser extent by cellular enzymes, and thus may be more stable.

Among the uses of the disclosed NtMRP polynucleotides, and combinations of fragments thereof, is the use of fragments as probes in polynucleotide hybridisation assays or primers for use in polynucleotide amplification assays or the use of fragments in the development of various polynucleotide constructs—such as RNAi molecules. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in a further aspect, there is also provided a method for detecting NtMRP polynucleotides comprising the use of the probes and/or the primers described herein.

The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences set forth above, sets of degenerate oligonucleotides can be prepared. Such oligonucleotides are useful as primers, for example, in polymerase chain reactions (PCR), whereby polynucleotide fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human homologues of the NtMRP sequences identified herein.

Also of potential use are polynucleotides and oligonucleotides (for example, primers or probes) that hybridize under reduced stringency conditions, typically moderately stringent conditions, and commonly highly stringent conditions, to an NtMRP polynucleotide described herein. The basic parameters affecting the choice of hybridization conditions and guidance for devising suitable conditions are described in Sambrook, J., E. F. Fritsch, and T. Maniatis (1989, Molecular Cloning: A Laboratory Manual, Cold Spring Harbor Laboratory Press, Cold Spring Harbor, N.Y.) and can be readily determined by those having ordinary skill in the art based on, for example, the length or base composition of the polynucleotide.

One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15M sodium chloride, 10 mM sodium phosphate, and 1.25 mM Ethylenediaminetetraacetic acid, pH 7.4) can be substituted for Standard Sodium Citrate (1× Standard Sodium Citrate is 0.15M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y.). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(number of A+T bases)+4(number of G+C bases). For hybrids above 18 base pairs in length, $T_m$ (° C.)=81.5+ 16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 65%, 70%, 75%, 80%, 85%, 90%, 95%, 97.5%, or at least 99%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation.

Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction.

NtMRP polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. NtMRP3 or NtMRP4 polypeptides may be in linear form or cyclized using known methods. NtMRP4 polypeptides comprise at least 10, at least 20, at least 30, or at least 40 contiguous amino acids.

Various embodiments are directed to isolated NtMRP3 polypeptides encoded by a polynucleotide sequence comprising, consisting of consisting essentially of SEQ ID NO:28 or SEQ ID NO:29 or SEQ ID NO:51 and fragments of SEQ ID NO:28 or SEQ ID NO:29 or SEQ ID NO:51, or variants thereof.

Various embodiments are directed to isolated NtMRP4 polypeptides encoded by a polynucleotide sequence comprising, consisting of consisting essentially of SEQ ID NO:1 or SEQ ID NO:2 or SEQ ID NO:27, fragments of SEQ ID NO:1 or SEQ ID NO:2 or SEQ ID NO:27, or variants thereof.

Various embodiments are directed to isolated NtMRP polypeptide variants comprising at least 70%, 75%, 80%, 85%, 90%, 95%, 96%, 97%, 98%, and 99% sequence identity to SEQ ID NO:1 or SEQ ID NO:2 or SEQ ID NO:27 or SEQ ID NO:28 or SEQ ID NO:29 or SEQ ID NO:51 or fragments of SEQ ID NO:1 or SEQ ID NO:2 or SEQ ID NO:27 or SEQ ID NO:28 or SEQ ID NO:29 or SEQ ID NO;51.

Mutant polypeptide variants of NtMRP, NtMRP3 and NtMRP4 are also encompassed by the claims and are disclosed herein as are mutant, non-naturally occurring or transgenic plants (for example, mutant, non-naturally occurring or transgenic tobacco plants) comprising the mutant polypeptide variants of NtMRP and/or MtMRP3 and/or NtMRP4.

The term 'non-naturally occurring' as used herein describes an entity (for example, a polynucleotide, a genetic mutation, a polypeptide, a plant, a plant cell and plant material) that is not formed by nature or that does not exist in nature. Such non-naturally occurring entities or artificial entities may be made, synthesized, initiated, modified, intervened, or manipulated by methods described herein or that are known in the art. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgress ion of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. Differences in genetic background can be detected by phenotypic differences or by molecular biology techniques known in the art—such as polynucleotide sequencing, presence or absence of genetic markers (for example, microsatellite RNA markers).

A polypeptide may be prepared by culturing transformed or recombinant host cells under culture conditions suitable to express a polypeptide. The resulting expressed polypeptide may then be purified from such culture using known purification processes. The purification of the polypeptide may also include an affinity column containing agents which will bind to the polypeptide; one or more column steps over such affinity resins such as concanavalin A-agarose, heparin-Toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, the polypeptide may also be expressed in a form that will facilitate purification. For example, it may be expressed as a fusion polypeptide, such as those of maltose binding polypeptide (MBP), glutathione-5-transferase (GST) or thioredoxin (TRX). Kits for expression and purification of such fusion polypeptides are commercially available from New England BioLab (Beverly, Mass.), Pharmacia (Piscataway, N.J.), and InVitrogen, respectively. The polypeptide can also be tagged with an epitope and subsequently purified by using a specific antibody directed to such epitope. Finally, one or more reverse-phase high performance liquid chromatography (RP-HPLC) steps employing hydrophobic RP-HPLC media, for example, silica gel having pendant methyl or other aliphatic groups, can be employed to further purify the polypeptide. Some or all of the foregoing purification steps, in various combinations, can also be employed to provide a substantially homogeneous recombinant polypeptide. The polypeptide thus purified is substantially free of other polypeptides and is defined herein as an "substantially purified polypeptide"; such purified polypeptides include NtMRP polypeptide, fragment, variant, and the like. Expression, isolation, and purification of the polypeptides and fragments can be accomplished by any suitable technique, including but not limited to the methods described herein.

It is also possible to utilize an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure. A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with a native polypeptides may possess biological properties in common therewith, including biological activity.

Embodiments are directed to compositions and methods for producing mutant, non-naturally occurring or transgenic plants that have been modified to reduce or impede heavy metal (for example, cadmium) transport to the leaf lamina by reducing the expression levels of NtMRP polynucleotide or the by reducing the activity of the protein encoded thereby. The steady-state level of NtMRP RNA transcripts can be decreased as compared to a control plant. Consequently, the number of functionally active NtMRP transporters available for transporting heavy metals (for example, cadmium) across cellular membranes can be decreased such that the level of cadmium in the plant is also decreased.

The reduction in expression of NtMRP polynucleotide may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or up to 100%, which includes a reduction in transcriptional activity or protein expression.

The reduction in the activity of NtMRP protein may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or up to 100%.

Inhibition refers to a reduction of from about 98% to about 100%, or a reduction of at least 98%, at least 99%, but particularly of 100%.

Polynucleotides and recombinant constructs described herein can be used to modulate (for example, reduce or inhibit) the expression of a NtMRP polypeptide in a plant species of interest. A number of polynucleotide based methods, including antisense RNA, ribozyme directed RNA cleavage, post-transcriptional gene silencing (PTGS), for example, RNA interference (RNAi), and transcriptional gene silencing (TGS) are known to inhibit gene expression in plants. Suitable polynucleotides include full-length polynucleotides encoding NtMRP polypeptides or fragments of such full-length polynucleotides. In some embodiments, a complement of the full-length polynucleotide or a fragment thereof can be used. Typically, a fragment is at least 10 contiguous nucleotides, for example, at least 10, 11, 12, 13, 14, 15, 16, 17, 18, 19, 20, 21, 22, 23, 24, 25, 26, 27, 30, 35, 40, 50, 80, 100, 200, 500 contiguous nucleotides or more. Generally, higher homology can be used to compensate for the use of a shorter sequence.

Thus, compositions that can modulate (for example, reduce or inhibit) the expression or the activity of NtMRP include, but are not limited to, sequence-specific polynucleotides that can interfere with the transcription of one or more endogenous NtMRP gene(s); sequence-specific polynucleotides that can interfere with the translation of NtMRP RNA transcripts (for example, double-stranded RNAs, siRNAs, ribozymes); sequence-specific polypeptides that can interfere with the stability of NtMRP proteins; sequence-specific polynucleotides that can interfere with the enzymatic activity of NtMRP protein or the binding activity of NtMRP protein with respect to substrates or regulatory proteins; antibodies that exhibit specificity for NtMRP protein; small molecule compounds that can interfere with the stability of NtMRP protein or the enzymatic activity of NtMRP protein or the binding activity of NtMRP protein; zinc finger proteins that bind NtMRP polynucleotide; and meganucleases that have activity towards NtMRP polynucleotide. Antisense technology is one well-known method that can be used to modulate (for example, reduce or inhibit) the expression of a NtMRP polypeptide. A polynucleotide of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

For example, a construct can be prepared that includes a sequence that is transcribed into an RNA that can anneal to itself, for example, a double stranded RNA having a stem-loop structure. In some embodiments, one strand of the stem portion of a double stranded RNA comprises a sequence that is similar or identical to the sense coding sequence or a fragment thereof of a NtMRP polynucleotide, and that is from about 10 nucleotides to about 2,500 contiguous nucleotides in length. The length of the sequence that is similar or identical to the sense coding sequence can be from 10 contiguous nucleotides to 500 contiguous nucleotides, from 15 contiguous nucleotides to 300 contiguous nucleotides, from 20 contiguous nucleotides to 100 contiguous nucleotides, or from 25 contiguous nucleotides to 100 contiguous nucleotides. The other strand of the stem portion of a double stranded RNA comprises a sequence that is similar or identical to the antisense strand or a fragment thereof of the coding sequence of the NtMRP polynucleotide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a NtMRP polypeptide, and the other strand of the stem portion of the double stranded RNA comprises a sequence that is similar or identical to the sequence that is complementary to the 3' or 5' untranslated region, respectively, or a fragment thereof, of the mRNA encoding the NtMRP. In other embodiments, one strand of the stem portion of a double stranded RNA comprises a sequence that is similar or identical to the sequence of an intron, or a fragment thereof, in the pre-mRNA encoding a NtMRP polypeptide, and the other strand of the stem portion comprises a sequence that is similar or identical to the sequence that is complementary to the sequence of the intron, or a fragment thereof, in the pre-mRNA.

The loop portion of a double stranded RNA can be from about 3 nucleotides to about 5,000 nucleotides—such as from about 15 nucleotides to about 1000 nucleotides, from about 20 nucleotides to about 500 nucleotides, from about 25 nucleotides to 250 nucleotides. The loop portion of the RNA can include an intron or a fragment thereof. A double stranded RNA can have zero, one, two, three, four, five, six, seven, eight, nine, ten, or more stem-loop structures. A construct including a sequence that is operably linked to a regulatory region or a transcription termination sequence, and that is transcribed into an RNA that can form a double stranded RNA, can be transformed into plants as described herein. Methods for using RNAi to inhibit the expression of a gene are known to those of skill in the art.

Constructs comprising regulatory regions operably linked to polynucleotide molecules in sense orientation can also be used to inhibit the expression of a gene. The transcription product can be similar or identical to the sense coding sequence, or a fragment thereof, of a NtMRP polypeptide. The transcription product also can be unpolyadenylated, lack a 5' cap structure, or contain an unspliceable intron. Methods of inhibiting gene expression using a full-length cDNA as well as a partial cDNA sequence are known in the art.

In some embodiments, a construct comprising a polynucleotide having at least one strand that is a template for both sense and antisense sequences that are complementary to each other is used to inhibit the expression of a gene. The sense and antisense sequences can be part of a larger polynucleotide molecule or can be part of separate polynucleotide molecules having sequences that are not complementary. The sense or antisense sequence can be a sequence that is identical or complementary to the sequence of an mRNA, the 3' or 5' untranslated region of an mRNA, or an intron in a pre-mRNA encoding a NtMRP polypeptide, or a fragment of such sequences. In some embodiments, the sense or antisense sequence is identical or complementary to a sequence of the regulatory region that drives transcription of the gene encoding a NtMRP polypeptide. In each case, the sense sequence is the sequence that is complementary to the antisense sequence.

The sense and antisense sequences can be a length greater than about 10 nucleotides (for example, about 10, 11, 12, 13, 14, 15, 16, 17, 18, 19, 20, 21, 22, 23, 24, 25, 26, 27, 28, 29, 30, or more nucleotides). For example, an antisense sequence can be about 20, 21, 22, 23, 24, 25, 26, 27, 28, 29, or 30 nucleotides in length. Typically, the sense and antisense sequences range in length from about 15 nucleotides to about 30 nucleotides, for example, from about 18 nucleotides to about 28 nucleotides, or from about from about 21 nucleotides to about 25 nucleotides, or from about 23 nucleotides to about 25 nucleotides.

In some embodiments, an antisense sequence is a sequence complementary to an mRNA sequence, or a fragment thereof, encoding a NtMRP polypeptide described herein. The sense sequence complementary to the antisense sequence can be a sequence present within the mRNA of the NtMRP polypeptide. Typically, sense and antisense sequences are designed to correspond to a 15-30 nucleotide sequence of a target mRNA such that the level of that target mRNA is reduced.

In some embodiments, a construct comprising a polynucleotide having at least one strand that is a template for more than one sense sequence (for example, about 2, 3, 4, 5, 6, 7, 8, 9, 10 or more sense sequences) can be used to inhibit the expression of a gene. Likewise, a construct comprising a polynucleotide having at least one strand that is a template for more than one antisense sequence (for example, about 2, 3, 4, 5, 6, 7, 8, 9, 10 or more antisense sequences) can be used to inhibit the expression of a gene. For example, a construct can contain a polynucleotide having at least one strand that is a template for two sense sequences and two antisense sequences. The multiple sense sequences can be identical or different. The multiple antisense sequences can be identical or different. For example, a construct can comprise a polynucleotide having one strand that is a template for two identical sense sequences and two identical antisense sequences that are complementary to the two identical sense sequences. Alternatively, an isolated polynucleotide can comprise one strand that is a template for (1) two identical sense sequences about 10, 11, 12, 13, 14, 15, 16, 17, 18, 19, 20, 21, 22, 23, 24, 25, 26, 27, 28, 29, or 30 or more nucleotides in length, (2) one antisense sequence that is complementary to the two identical sense sequences about 10, 11, 12, 13, 14, 15, 16, 17, 18, 19, 20, 21, 22, 23, 24, 25, 26, 27, 28, 29 or 30 or more nucleotides in length, (3) a sense sequence about 10, 11, 12, 13, 14, 15, 16, 17, 18, 19, 20, 21, 22, 23, 24, 25, 26, 27, 28, 29 or 30 or more nucleotides in length, and (4) three identical antisense sequences that are complementary to the sense sequence about 10, 11, 12, 13, 14, 15, 16, 17, 18, 19, 20, 21, 22, 23, 24, 25, 26, 27, 28, 29 or 30 or more nucleotides in length. The constructs provided herein can be designed to have any arrangement of sense and antisense sequences. For example, two identical sense sequences can be followed by two identical antisense sequences or can be positioned between two identical antisense sequences.

A polynucleotide comprising at least one strand that is a template for one or more sense or antisense sequences can be operably linked to a regulatory region to drive transcription of an RNA molecule comprising the sense or antisense sequence(s). In addition, such a polynucleotide can be operably linked to a transcription terminator sequence, such as the terminator of the nopaline synthase (nos) gene. In some cases, two regulatory regions can direct transcription of two transcripts: one from the top strand, and one from the bottom strand. The two regulatory regions can be the same or different. The two transcripts can form double-stranded RNA molecules that induce degradation of the target RNA. In some cases, a polynucleotide can be positioned within a T-DNA or plant-derived transfer DNA (P-DNA) such that the left and right T-DNA border sequences, or the left and right border-like sequences of the P-DNA, flank or are on either side of the polynucleotide. The polynucleotide sequence between the two regulatory regions can be from about 15 to about 300 nucleotides in length, from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

Accordingly, compositions that can modulate (for example, down-regulate) the expression or the activity of NtMRP protein include sequence-specific polynucleotides that can interfere with the transcription of one or more endogenous NtMRP gene(s); sequence-specific polynucleotides that can interfere with the translation of NtMRP RNA transcripts (for example, double-stranded RNAs, siRNAs, ribozymes); sequence-specific polypeptides that can interfere with the stability of NtMRP proteins; sequence-specific polynucleotides that can interfere with the enzymatic activity of NtMRP protein or the binding activity of NtMRP protein with respect to substrates or regulatory proteins; antibodies that exhibit specificity for NtMRP protein; small molecule compounds that can interfere with the stability of NtMRP protein or the enzymatic activity of NtMRP protein or the binding activity of NtMRP protein; zinc finger proteins that bind NtMRP polynucleotide; and meganucleases that have activity towards NtMRP polynucleotide.

An effective antagonist can reduce heavy metal (for example, cadmium) transport into the leaf (for example, leaf lamina structures) by at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100%. In one embodiment, the sequence-specific polynucleotides that can interfere with the translation of NtMRP RNA transcript(s) is RNAi.

RNA Interference ("RNAi") or RNA silencing is an evolutionarily conserved process by which specific mRNAs can be targeted for enzymatic degradation. A double-stranded RNA (double-stranded RNA) must be introduced or produced by a cell (for example, double-stranded RNA virus, or NtMRP RNAi polynucleotides) to initiate the RNAi pathway. The double-stranded RNA can be converted into multiple siRNA duplexes of 21-23 bp length ("siRNAs") by RNases III, which are double-stranded RNA-specific endonucleases ("Dicer"). The siRNAs can be subsequently recognized by RNA-induced silencing complexes ("RISC") that promote the unwinding of siRNA through an ATP-dependent process. The unwound antisense strand of the siRNA guides the activated RISC to the targeted mRNA (for example, NtMRP RNA variants) comprising a sequence complementary to the siRNA anti-sense strand. The targeted mRNA and the anti-sense strand can form an A-form helix, and the major groove of the A-form helix can be recognized by the activated RISC. The target mRNA can be cleaved by activated RISC at a single site defined by the binding site of the 5'-end of the siRNA strand. The activated RISC can be recycled to catalyze another cleavage event.

NtMRP RNAi expression vectors comprising NtMRP RNAi constructs encoding NtMRP RNAi polynucleotides exhibit RNA interference activity by reducing the expression level of NtMRP mRNAs, NtMRP pre-mRNAs, or related NtMRP RNA variants. The expression vectors may comprise a promoter positioned upstream and operably-linked to a NtMRP RNAi construct, as further described herein. NtMRP RNAi expression vectors may comprise a suitable minimal core promoter, a NtMRP RNAi construct of interest, an upstream (5') regulatory region, a downstream (3') regulatory region, including transcription termination and polyadenylation signals, and other sequences known to persons skilled in the art, such as various selection markers.

The NtMRP polynucleotides can be produced in various forms, including as double stranded structures (that is, a double-stranded RNA molecule comprising an antisense strand and a complementary sense strand), double-stranded hairpin-like structures ("dsRNAi"), single-stranded structures (that is, a ssRNA molecule comprising just an antisense strand). The structures may comprise a duplex, asymmetric duplex, hairpin or asymmetric hairpin secondary structure, having self-complementary sense and antisense strands. The NtMRP dsRNAi can be enzymatically converted to double-stranded NtMRP siRNAs. One of the strands of the NtMRP siRNA duplex can anneal to a complementary sequence within the target NtMRP mRNA and related NtMRP RNA variants. The siRNA/mRNA duplexes are recognized by RISC that can cleave NtMRP RNAs at multiple sites in a sequence-dependent manner, resulting in the degradation of the target NtMRP mRNA and related NtMRP RNA variants.

The double-stranded RNA molecules may include siRNA molecules assembled from a single oligonucleotide in a stem-loop structure, wherein self-complementary sense and antisense regions of the siRNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi.

Small hairpin RNA (shRNA) molecules are also disclosed herein, comprising a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a shRNA. The spacer sequence generally comprises between about 3 and about 100 nucleotides.

Any NtMRP RNA polynucleotide of interest can be produced by selecting a suitable sequence composition, loop size, and stem length for producing the NtMRP hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the siRNA molecule is a double-stranded RNA or ssRNA molecule between about 15 and about 35 nucleotides in length. In another embodiment, the siRNA molecule is a double-stranded RNA or ssRNA molecule between about 17 and about 30 nucleotides in length. In another embodiment, the siRNA molecule is a double-stranded RNA or ssRNA molecule between about 19 and about 25 nucleotides in length. In another embodiment, the siRNA molecule is a double-stranded RNA or ssRNA molecule between about 21 to about 23 nucleotides in length. In certain embodiments, hairpin structures with duplexed regions longer than 21 nucleotides may promote effective siRNA-directed silencing, regardless of loop sequence and length.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA; and no "runs" of more than three consecutive guanine (G) nucleotides or more than three consecutive cytosine (C) nucleotides. These criteria can be assessed using various techniques known in the art, for example, computer programs such as BLAST® (the Basic Local Alignment Search Tool) can be used to search publicly available databases to determine whether the selected target sequence is unique to the target mRNA. Alternatively, a target sequence can be selected (and a siRNA sequence designed) using computer software available commercially (for example, OligoEngine™ (Seattle, Wash.); Dharmacon, Inc. (Lafayette, Colo.); Target Finder from Ambion Inc. (Austin, Tex.) and the siRNA Design Tool from QIAGEN, Inc. (Valencia, Calif.)).

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the siRNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the sequences as set forth in SEQ ID NOs:1-23.

The specific antisense sequence comprised by the siRNA molecule can be identical or substantially identical to the complement of the target sequence. In one embodiment, the specific antisense sequence comprised by the siRNA molecule is at least about 75%, 80%, 85%, 90%, 95%, 96%, 97%, 98% or 99% identical to the complement of the target mRNA sequence. Methods of determining sequence identity are known in the art and can be determined, for example, by using the BLAST® (the Basic Local Alignment Search Tool) BLASTN program of the University of Wisconsin Computer Group (GCG) software or provided on the NCBI website.

The specific antisense sequence of the siRNA molecules described herein may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. double-stranded RNA molecules in which one or more nucleotide substitution occurs in the sense sequence, but not in the antisense strand, are also contemplated. When the antisense sequence of an siRNA molecule comprises one or more mismatches between the nucleotide sequence of the siRNA and the target nucleotide sequence, as described above, the mismatches may be found at the 3' terminus, the 5' terminus or in the central portion of the antisense sequence.

In another embodiment, the siRNA molecules comprise a specific antisense sequence that is capable of selectively hybridizing under stringent conditions to a portion of a naturally occurring target gene or target mRNA. Suitable stringent conditions include, for example, hybridization according to conventional hybridization procedures and washing conditions of 1-3.times. Standard Sodium Citrate, 0.1-1% Sodium Dodecyl Sulphate, 50-70.degree.C. with a change of wash solution after about 5-30 minutes. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

RNAi molecules having a duplex or double-stranded structure, for example double-stranded RNA or shRNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the RNAi molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the RNAi molecule comprises a 3' overhang at one end of the molecule, the other end can be blunt-ended or have also an overhang (5' or 3'). When the RNAi molecule comprises an overhang at both ends of the molecule, the length of the overhangs may be the same or different. In one embodiment, the RNAi molecule described herein comprises 3' overhangs of about 1 to about 3 nucleotides on both ends of the molecule. In a further embodiment, the RNAi molecule is a double-stranded RNA having a 3' overhang of 2 nucleotides at both ends of the molecule. In yet another embodiment, the nucleotides comprising the overhang of the RNAi are TT dinucleotides or UU dinucleotides.

When determining the percentage identity of the RNAi molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the siRNA molecule.

The RNAi molecules can comprise one or more 5' or 3'-cap structures. The RNAi molecule can comprise a cap structure at the 3'-end of the sense strand, the antisense strand, or both the sense and antisense strands; or at the 5'-end of the sense strand, the antisense strand, or both the sense and antisense strands of the RNAi molecule. Alternatively, the RNAi molecule can comprise a cap structure at both the 3'-end and 5'-end of the RNAi molecule. The term "cap structure" refers to a chemical modification incorporated at either terminus of an oligonucleotide (see, for example, U.S. Pat. No. 5,998,203), which protects the molecule from exonuclease degradation, and may also facilitate delivery or localisation within a cell.

Another modification applicable to RNAi molecules is the chemical linkage to the RNAi molecule of one or more moieties or conjugates which enhance the activity, cellular distribution, cellular uptake, bioavailability or stability of the RNAi molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

In yet another embodiment, the nucleotides at one or both of the two single strands may be modified to prevent or inhibit the activation of cellular enzymes, such as, for example, without limitation, certain nucleases. Techniques for inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to a RNAi molecule, for example, to enhance its cellular absorption. In certain embodiment, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands are propylammonium and dimethylpropylammonium. Anti-sense oligonucleotides can retain their high binding affinity to mRNA when the cationic ligand is dispersed throughout the oligonucleotide.

The molecules and nucleotides described herein may be prepared using well-known technique of solid-phase synthesis. Any other means for such synthesis known in the art may additionally or alternatively be employed.

Various embodiments are directed to NtMRP expression vectors (for example, NtMRP3 expression vectors) comprising NtMRP polynucleotide or NtMRP RNAi constructs that comprise one or more of: SEQ ID NO: 28, SEQ ID NO: 29, SEQ ID NO: 51, intron 1 (SEQ ID NO:30), intron 2 (SEQ ID NO:31), intron 3 (SEQ ID NO:32), intron 4 (SEQ ID NO:33), intron 5 (SEQ ID NO:34), intron 6 (SEQ ID NO:35), intron 7 (SEQ ID NO:36), intron 8 (SEQ ID NO:37), intron 9 (SEQ ID NO:38), intron 10 (SEQ ID NO:39), exon 1 (SEQ ID NO:40), exon 2 (SEQ ID NO:41), exon 3 (SEQ ID NO:42) exon 4 (SEQ ID NO:43), exon 5 (SEQ ID NO:44), exon 6 (SEQ ID NO:45) exon 7 (SEQ ID NO:46) exon 8 (SEQ ID NO:47), exon 9 (SEQ ID NO:48) exon 10 (SEQ ID NO:49) or exon 11 (SEQ ID NO:50). and fragments thereof, and variants thereof. As described herein, reference to the specific sequences also includes the complement or reverse complement thereof.

Various embodiments are directed to NtMRP expression vectors (for example, NtMRP4 expression vectors) comprising NtMRP polynucleotide or NtMRP RNAi constructs that comprise one or more of: SEQ ID NO:1, SEQ ID NO:2, SEQ ID NO:27, intron 1 (SEQ ID NO:3), intron 2 (SEQ ID NO:4), intron 3 (SEQ ID NO:5), intron 4 (SEQ ID NO:6), intron 5 (SEQ ID NO:7), intron 6 (SEQ ID NO:8), intron 7 (SEQ ID NO:9), intron 8 (SEQ ID NO:10), intron 9 (SEQ ID NO:11), intron 10 (SEQ ID NO:12), exon 1 (SEQ ID NO:13), exon 2 (SEQ ID NO:14), exon 3 (SEQ ID NO:15) exon 4 (SEQ ID NO:16), exon 5 (SEQ ID NO:17), exon 6 (SEQ ID NO:18) exon 7 (SEQ ID NO:19) exon 8 (SEQ ID NO:20), exon 9 (SEQ ID NO:21) exon 10 (SEQ ID NO:22), exon 11 (SEQ ID NO:53) or SEQ ID No. 23 and fragments thereof, and variants thereof. As described herein, reference to the specific sequences also includes the complement or reverse complement thereof.

Various embodiments are directed to expression vectors comprising: one or more NtMRP polynucleotide(s) or NtMRP RNAi constructs (for example, NtMRP3 polynucleotide or NtMRP3 RNAi constructs) having at least 71%, 72%, 73%, 74%, 75%, 80%, 85%, 90%, 95%, 96%, 97%, 98%, and 99% sequence identity to a sequence selected from the group consisting of: SEQ ID NO: 28, SEQ ID NO: 29, intron 1 (SEQ ID NO:30), intron 2 (SEQ ID NO:31), intron 3 (SEQ ID NO:32), intron 4 (SEQ ID NO:33), intron 5 (SEQ ID NO:34), intron 6 (SEQ ID NO:35), intron 7 (SEQ ID NO:36), intron 8 (SEQ ID NO:37), intron 9 (SEQ ID NO:38), intron 10 (SEQ ID NO:39), exon 1 (SEQ ID NO:40), exon 2 (SEQ ID NO:41), exon 3 (SEQ ID NO:42) exon 4 (SEQ ID NO:43), exon 5 (SEQ ID NO:44), exon 6 (SEQ ID NO:45) exon 7 (SEQ ID NO:46) exon 8 (SEQ ID NO:47), exon 9 (SEQ ID NO:48), exon 10 (SEQ ID NO:49), exon 11 (SEQ ID NO:50) or SEQ ID NO;51 and fragments thereof, and variants thereof or a combination of two or more thereof.

As described herein, reference to the specific sequences also includes the complement or reverse complement thereof.

Various embodiments are directed to expression vectors comprising: NtMRP polynucleotide or NtMRP RNAi constructs (for example, NtMRP4 polynucleotide or NtMRP4 RNAi constructs) having at least 70%, 71%, 72%, 73%, 74%, 75%, 80%, 85%, 90%, 95%, 96%, 97%, 98%, and 99% sequence identity to a sequence selected from the group consisting of: SEQ ID NO:1, SEQ ID NO:2, intron 1 (SEQ ID NO:3), intron 2 (SEQ ID NO:4), intron 3 (SEQ ID NO:5), intron 4 (SEQ ID NO:6), intron 5 (SEQ ID NO:7), intron 6 (SEQ ID NO:8), intron 7 (SEQ ID NO:9), intron 8 (SEQ ID NO:10), intron 9 (SEQ ID NO:11), intron 10 (SEQ ID NO:12), exon 1 (SEQ ID NO:13), exon 2 (SEQ ID NO:14), exon 3 (SEQ ID NO:15) exon 4 (SEQ ID NO:16), exon 5 (SEQ ID NO:17), exon 6 (SEQ ID NO:18) exon 7 (SEQ ID NO:19) exon 8 (SEQ ID NO:20), exon 9 (SEQ ID NO:21) exon 10 (SEQ ID NO:21), exon 11 (SEQ ID NO:22) or SEQ ID No. 23 and fragments thereof, and variants thereof or a combination of two or more thereof. As described herein, reference to the specific sequences also includes the complement or reverse complement thereof.

Various embodiments are directed to expression vectors comprising: NtMRP polynucleotide or NtMRP RNAi construct encoding NtMRP RNAi polynucleotides (for example, NtMRP3 polynucleotide or NtMRP3 RNAi constructs encoding NtMRP3 RNAi polynucleotides) capable of self-annealing to form a hairpin structure, in which the construct comprises (a) a first sequence having at least 71%, 72%, 73%, 74%, 75%, 80%, 85%, 90%, 95%, 96%, 97%, 98%, and 99% sequence identity to a sequence selected from the group consisting of: SEQ ID NO: 28, SEQ ID NO: 29, intron 1 (SEQ ID NO:30), intron 2 (SEQ ID NO:31), intron 3 (SEQ ID NO:32), intron 4 (SEQ ID NO:33), intron 5 (SEQ ID NO:34), intron 6 (SEQ ID NO:35), intron 7 (SEQ ID NO:36), intron 8 (SEQ ID NO:37), intron 9 (SEQ ID NO:38), intron 10 (SEQ ID NO:39), exon 1 (SEQ ID NO:40), exon 2 (SEQ ID NO:41), exon 3 (SEQ ID NO:42) exon 4 (SEQ ID NO:43), exon 5 (SEQ ID NO:44), exon 6 (SEQ ID NO:45) exon 7 (SEQ ID NO:46), exon 8 (SEQ ID NO:47), exon 9 (SEQ ID NO:48), exon 10 (SEQ ID NO:49), exon 11 (SEQ ID NO:50) or SEQ ID NO:51 and fragments thereof, and variants thereof or a combination of two or more thereof; (b) a second sequence encoding a spacer element of the that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence. As described herein, reference to the specific sequences also includes the complement or reverse complement thereof.

Various embodiments are directed to expression vectors comprising: NtMRP polynucleotide or NtMRP RNAi construct encoding NtMRP RNAi polynucleotides (for example, NtMRP4 polynucleotide or NtMRP4 RNAi constructs encoding NtMRP4 RNAi polynucleotides) capable of self-annealing to form a hairpin structure, in which the construct comprises (a) a first sequence having at least 71%, 72%, 73%, 74%, 75%, 80%, 85%, 90%, 95%, 96%, 97%, 98%, and 99% sequence identity to a sequence selected from the group consisting of: SEQ ID NO:1, SEQ ID NO:2, intron 1 (SEQ ID NO:3), intron 2 (SEQ ID NO:4), intron 3 (SEQ ID NO:5), intron 4 (SEQ ID NO:6), intron 5 (SEQ ID NO:7), intron 6 (SEQ ID NO:8), intron 7 (SEQ ID NO:9), intron 8 (SEQ ID NO:10), intron 9 (SEQ ID NO:11), intron 10 (SEQ ID NO:12), exon 1 (SEQ ID NO:13), exon 2 (SEQ ID NO:14), exon 3 (SEQ ID NO:15) exon 4 (SEQ ID NO:16), exon 5 (SEQ ID NO:17), exon 6 (SEQ ID NO:18) exon 7 (SEQ ID NO:19) exon 8 (SEQ ID NO:20), exon 9 (SEQ ID NO:21) exon 10 (SEQ ID NO:22), exon 11 (SEQ ID NO:53), SEQ ID No. 23 or SEQ ID NO:51 and fragments thereof, and variants thereof or a combination of two or more thereof; (b) a second sequence encoding a spacer element of the that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence. As described herein, reference to the specific sequences also includes the complement or reverse complement thereof. The disclosed sequences can be utilized for constructing various NtMRP polynucleotides that do not form hairpin structures. For example, a NtMRP double-stranded RNA can be formed by (1) transcribing a first strand of the NtMRP cDNA by operably-linking to a first promoter, and (2) transcribing the reverse complementary sequence of the first strand of the NtMRP cDNA fragment by operably-linking to a second promoter. Each strand of the NtMRP polynucleotide can be transcribed from the same expression vector, or from different expression vectors. The NtMRP RNA duplex having RNA interference activity can be enzymatically converted to siRNAs to reduce NtMRP RNA levels.

Various embodiments are directed to NtMRP expression vectors comprising NtMRP polynucleotide or NtMRP RNAi construct encoding NtMRP RNAi polynucleotides (for example, NtMRP3 expression vectors comprising NtMRP3 polynucleotide or NtMRP3 RNAi constructs encoding NtMRP3 RNA i polynucleotides) capable of self-annealing, in which the construct comprises (a) a first sequence having at least 71%, 72%, 73%, 74%, 75%, 80%, 85%, 90%, 95%, 96%, 97%, 98%, 99% or 100% sequence identity to a sequence selected from the group consisting of: SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50 and SEQ ID NO:51, and fragments thereof, and variants thereof or a combination of two or more thereof; and (b) a second sequence comprising a complementary (for example, reverse complementary) sequence of the first sequence, positioned in the same orientation as the first sequence. As described herein, reference to the specific sequences also includes the complement or reverse complement thereof.

Other embodiments are directed to NtMRP expression vectors comprising NtMRP polynucleotide or NtMRP RNAi construct encoding NtMRP RNAi polynucleotides (for example, NtMRP4 expression vectors comprising NtMRP4 polynucleotide or NtMRP4 RNAi constructs encoding NtMRP4 RNA i polynucleotides) capable of self-annealing, in which the construct comprises (a) a first sequence having at least 71%, 72%, 73%, 74%, 75%, 80%, 85%, 90%, 95%, 96%, 97%, 98%, 99% or 100% sequence identity to a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15 SEQ ID NO:16, SEQ ID NO:17, SEQ ID NO:18, SEQ ID NO:19, SEQ ID NO:20, SEQ ID NO:21, SEQ ID NO:21, SEQ ID NO:22, SEQ ID No. 23, SEQ ID NO:27 and SEQ ID NO: 53 and fragments thereof, and variants thereof or a combination of two or more thereof; and (b) a second sequence comprising a complementary (for example, reverse complementary) sequence of the first sequence, positioned in the same orientation as the first sequence. As described herein, reference to the specific sequences also includes the complement or reverse complement thereof.

Various compositions and methods are provided for modulating (for example, reducing) the endogenous expression levels for members of the NtMRP gene family by promoting co-suppression of NtMRP gene expression. The phenomenon of co-suppression occurs as a result of introducing multiple copies of a transgene into a plant cell host. Integration of multiple copies of a transgene can result in reduced expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing ("P TGS"), in which transcripts can be produced but enhanced rates of degradation preclude accumulation of transcripts. The mechanism for co-suppression by PTGS is thought to resemble RNA interference, in that RNA seems to be both an important initiator and a target in these processes, and may be mediated at least in part by the same molecular machinery, possibly through RNA-guided degradation of mRNAs.

Co-suppression of NtMRP polynucleotide can be achieved by integrating multiple copies of the NtMRP cDNA or fragments thereof, as transgenes, into the genome of a plant of interest. The host plant can be transformed with an expression vector comprising a promoter operably-linked to NtMRP cDNA or fragments thereof. Various embodiments are directed to expression vectors for promoting co-suppression of endogenous genes of NtMRP comprising: a promoter operably-linked to NtMRP (for example, NtMRP cDNA) identified as SEQ ID NO:1, SEQ ID NO:2, SEQ ID NO: 28, SEQ ID NO: 29 or SEQ ID NO: 51 or a fragment thereof—such as any of SEQ ID NOs 3 to 23 or 30 to 50—or a variant thereof having at least about 65%, 66%, 67%, 68%, 69%, 70%, 71%, 72%, 73%, 74%, 75%, 80%, 85%, 90%, 95%, 96%, 97%, 98%, or 99% sequence identity thereto.

Various embodiments are directed to methods for modulating (for example, reducing or inhibiting) the expression level of NtMRP polynucleotide by integrating multiple copies of NtMRP polynucleotide (for example, NtMRP cDNA) identified as SEQ ID NO:1, SEQ ID NO:2, SEQ ID No. 28 or SEQ ID No. 29 or SEQ ID NO: 51 or a fragment thereof—such as any of SEQ ID NOs 3 to 23 or 30 to 50 or 53—or a variant thereof having at least about 65%, 66%, 67%, 68%, 69%, 70%, 71%, 72%, 73%, 74%, 75%, 80%, 85%, 90%, 95%, 96%, 97%, 98%, or 99% sequence identity thereto into a plant genome, comprising: transforming a plant cell host with an expression vector that comprises a promoter operably-linked to SEQ ID NO:1, SEQ ID NO:2, SEQ ID No. 28 or SEQ ID No. 29 or SEQ ID NO: 51 or a fragment thereof—such as any of SEQ ID NOs 3 to 23 or 30 to 50—or a variant thereof having at least about 65%, 66%, 67%, 68%, 69%, 70%, 71%, 72%, 73%, 74%, 75%, 80%, 85%, 90%, 95%, 96%, 97%, 98%, or 99% sequence identity thereto.

Various compositions and methods are provided for reducing the endogenous gene expression level of NtMRP by inhibiting the translation of NtMRP mRNA. A host plant cell can be transformed with an expression vector comprising: a promoter operably-linked to NtMRP polynucleotide or a variant or fragment thereof, positioned in anti-sense orientation with respect to the promoter to enable the expression of RNA polynucleotides having a sequence complementary to a portion of NtMRP mRNA.

Various expression vectors for inhibiting the translation of NtMRP mRNA may comprise: a promoter operably-linked to NtMRP (for example, NtMRP cDNA) identified as SEQ ID NO:1 or SEQ ID NO:2 or SEQ ID NO:27 or SEQ ID No, 28 or SEQ ID No. 29 or SEQ ID NO:51 or a fragment thereof—such as any of SEQ ID NOs 3 to 23 or 30 to 50 or 53—or a variant thereof having at least about 65%, 66%, 67%, 68%, 69%, 70%, 71%, 72%, 73%, 74%, 75%, 80%, 85%, 90%, 95%, 96%, 97%, 98%, or 99% sequence identity thereto in which the sequence is positioned in anti-sense orientation with respect to the promoter. The lengths of anti-sense NtMRP RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

Methods for obtaining mutant NtMRP polynucleotides and polypeptides are also provided. Any plant of interest, including a plant cell or plant material, can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Alternatively, NtMRP genes can be targeted for inactivation by introducing transposons (for example, IS elements) into the genomes of plants of interest. These mobile genetic elements can be introduced by sexual cross-fertilization and insertion mutants can be screened for loss in NtMRP protein activity, such as reduced cadmium transport. The disrupted NtMRP gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more NtMRP-related genes can be inactivated by the insertion of one or more transposons. Mutations can result in homozygous disruption of one or more NtMRP genes, in heterozygous disruption of one or more NtMRP genes, or a combination of both homozygous and heterozygous disruptions if more than one NtMRP gene is disrupted. Suitable transposable elements can be selected from two broad classes, designated as Class I and Class II. Suitable Class I transposable elements include retrotransposons, retroposons, and SINE-like elements. Such methods are known to persons skilled in the art.

Alternatively, NtMRP genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *solanum nodiflorum* mottle virus, and subterranean clover mottle virus. Various target RNA-specific ribozymes are known to persons skilled in the art.

In some embodiments, the expression of a NtMRP polypeptide is modulated, reduced, or inhibited by non-transgenic means, such as creating a mutation in a NtMRP gene, including a NtMRP3 and/or NtMRP4 gene. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis, tilling (targeting induced local lesions in genomes), homologous recombination, oligonucleotide-directed mutagenesis, and meganuclease-mediated mutagenesis.

Some examples of mutations are deletions, insertions and missense mutations of at least one nucleotide, single nucleotide polymorphisms (SNPs), a simple sequence repeat. After mutation, screening can be performed to identify deletions that create premature stop codons or otherwise non-functional NtMRP genes. Screening of mutants can be carried out by sequencing, or by the use of one or more probes or primers specific to the NtMRP gene or protein. Specific mutations in NtMRP polynucleotides can also be created that can result in decreased NtMRP gene expression, decreased stability of NtMRP mRNA, or decreased stability of the NtMRP protein. Such plants are referred to herein as "non-naturally occurring" plants or mutated plants.

The non-naturally occurring and mutant plants can have any combination of one or more mutations which results in reduced NtMRP polypeptide levels. For example, the plants may have a single mutation in a single NtMRP gene or multiple mutations in a single NtMRP gene. Accordingly, mutant or non-naturally occurring plants (for example, mutant, non-naturally occurring or transgenic tobacco plants and the like, as described herein) comprising the mutant polypeptide variants of NtMRP, NtMRP3 and NtMRP4 are disclosed.

In one embodiment, seeds from plants are mutagenized and then grown into first generation mutant plants. The first generation plants are then allowed to self-pollinate and seeds from the first generation plant are grown into second generation plants, which are then screened for mutations in their NtMRP loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenized in order to create the NtMRP-mutated plants. However, the type of plant material mutagenized may affect when the plant polynucleotide is screened for mutations. For example, when pollen is subjected to mutagenesis prior to pollination of a non-mutagenized plant, the seeds resulting from that pollination are grown into first generation plants. Every cell of the first generation plants will contain mutations created in the pollen; thus these first generation plants may then be screened for NtMRP mutations instead of waiting until the second generation.

Mutagens that create primarily point mutations and short deletions, insertions, transversions, and or transitions, including chemical mutagens or radiation, may be used to create the mutations. Mutagens include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethyl-phosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino]acridine dihydrochloride (ICR-170), and formaldehyde. Spontaneous mutations in the NtMRP locus that may not have been directly caused by the mutagen are also contemplated provided that they result in the desired phenotype described herein. Suitable mutagenic agents also include, for example, ionising radiation—such as X-rays, gamma rays, fast neutron irradiation and UV radiation.

Any method of plant polynucleotide preparation known to those of skill in the art may be used to prepare the plant polynucleotide for NtMRP mutation screening.

Prepared polynucleotide from individual plants can optionally pooled in order to expedite screening for mutations in the NtMRP gene of the entire population of plants originating from the mutagenized plant tissue. One or more subsequent generations of plants, plant cells or plant material can be screened. The size of the optionally pooled group is dependent upon the sensitivity of the screening method used.

After the polynucleotide samples are optionally pooled, they can be subjected to NtMRP polynucleotide-specific amplification techniques, such as Polymerase Chain Reaction (PCR). Any one or more primers or probes specific to the NtMRP gene or the sequences immediately adjacent to the NtMRP gene may be utilized to amplify the NtMRP sequences within the pooled polynucleotide sample. Preferably, the one or more primers or probes are designed to amplify the regions of the NtMRP locus where useful mutations are most likely to arise. Most preferably, the one or more primers or probes are designed to detect mutations within exonic regions of NtMRP polynucleotide. Additionally, it is preferable for the one or more primers or probes to avoid known polymorphic sites in order to ease screening for point mutations. To facilitate detection of amplification products, the one or more primers or probes may be labelled using any conventional labelling method. One or more primers or probes can be designed based upon the NtMRP sequences described herein using methods that are well understood in the art. Polymorphisms may be identified by means known in the art.

In a further aspect there is provided a method of preparing a mutant plant. The method involves providing at least one cell of a plant comprising a gene encoding a functional NtMRP polypeptide. Next, the at least one cell of the plant is treated under conditions effective to modulate the activity of the NtMRP gene. The at least one mutant plant cell is then propagated into a mutant plant, where the mutant plant has a modulated level of NtMRP polypeptide as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the NtMRP gene which confer a desired trait. The mutant allele(s) that occurs naturally can be transferred to the second plant by various methods including breeding, backcrossing and introgression to produce lines, varieties or hybrids that have one or more mutations in the NtMRP gene. Plants showing a desired trait may be screened out of a pool of mutant plants. Suitably, the selection is carried out utilising the knowledge of the NtMRP nucleotide sequences as described herein. Consequently, it is possible to screen for a genetic trait being indicative for modulated (for example decreased) levels of cadmium as compared to a control. Such a screening approach may involve the application of conventional polynucleotide amplification and/or hybridization techniques as discussed herein. Thus, a further aspect relates to a method for identifying a mutant plant comprising the steps of: (a) providing a sample comprising a NtMRP polynucleotide from a plant; and (b) determining the polynucleotide sequence of the NtMRP polynucleotide, wherein a difference in the sequence of the NtMRP polynucleotide as compared to the NtMRP polynucleotide of a control plant is indicative that said plant is a NtMRP mutant plant. In another aspect there is provided a method for identifying a mutant plant which accumulates modulated (for example decreased) levels of cadmium as compared to a control plant comprising the steps of: (a) providing a sample from a plant to be screened; (b) determining if said sample comprises one or more mutations in the NtMRP polynucleotide; and (c) determining the cadmium content in at least a part of said plant; wherein if said sample comprises one or more mutations in the NtMRP polynucleotide that modulates (for example decreases) the expression or the activity of the protein encoded as compared to a control plant and at least a part of the plant has a modulated (for example decreased) cadmium content as compared to a control plant in which the expression or the activity of NtMRP has not been modulated (for example decreased) is indicative of a naturally occurring mutant plant which accumulates modulated (for example decreased) levels of cadmium. In another aspect there is provided a method for preparing a mutant plant which accumulates modulated (for example decreased) levels of cadmium as compared to a control plant comprising the steps of: (a) providing a sample from a first plant; (b) determining if said sample comprises one or more mutations in the NtMRP polynucleotide that result in modulated (for example decreased) levels of cadmium therein; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which accumulates modulated (for example decreased) levels of cadmium as compared to a control plant comprising the steps of: (a) providing a sample from a first plant; (b) determining if said sample comprises one or more mutations in the NtMRP polynucleotide that result in modulated (for example decreased) levels of cadmium therein; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar an elite cultivar). In one embodiment, the second plant is a cultivar or an elite cultivar). A further aspect relates to a mutant plant (including a cultivar or elite cultivar mutant plant) obtained or obtainable by the methods described herein. In certain embodiments, the mutant plants may have one or more mutations localised only to a specific region of the plant—such as within the sequence of the NtMRP polynucleotide. According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of the NtMRP polynucleotide and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the NtMRP polynucleotide; or may not have one or more mutations in one or more, two or more, three or more, four or more or five or more introns of the NtMRP polynucleotide; or may not have one or more mutations in a promoter of the NtMRP polynucleotide; or may not have one or more mutations in the 3' untranslated region of the NtMRP polynucleotide; or may not have one or more mutations in the 5' untranslated region of the NtMRP polynucleotide; or may not have one or more mutations in the coding region of the NtMRP polynucleotide; or may not have one or more mutations in the non-coding region of the NtMRP polynucleotide; or any combination of two or more, three or more, four or more, five or more; or six or more thereof parts thereof.

In a further aspect there is provided a method of identifying a plant, a plant cell or plant material comprising a mutation in a gene encoding NtMRP comprising: (a) subjecting a plant, a plant cell or plant material to mutagenesis; (b) obtaining a polynucleotide sample from said plant, plant cell or plant material or descendants thereof; and (c) determining the polynucleotide sequence of the gene encoding NtMRP or a variant or a fragment thereof, wherein a difference in said sequence is indicative of one or more mutations therein.

Zinc finger proteins can be used to modulate (for example, reduce or inhibit) the expression or the activity of NtMRP. In various embodiments, a genomic polynucleotide sequence comprising a part of or all of the coding sequence of a NtMRP polynucleotide is modified by zinc finger nuclease-mediated mutagenesis. The genomic polynucleotide sequence is searched for a unique site for zinc finger protein binding. Alternatively, the genomic polynucleotide sequence is searched for two unique sites for zinc finger protein binding wherein both sites are on opposite strands and close together, for example, 1, 2, 3, 4, 5, 6 or more basepairs apart. Accordingly, zinc finger proteins that bind to NtMRP polynucleotides are provided. A zinc finger DNA-binding domain or motif consists of approximately 30 amino acids that fold into a beta-beta-alpha structure of which the alpha-helix (α-helix) inserts into the DNA double helix. An "alpha-helix" refers to a motif in the secondary structure of a protein that is either right- or left-handed coiled in which the hydrogen of each N—H group of an amino acid is bound to the C=O group of an amino acid at position-4 relative to the first amino acid. A "beta-barrel" (β-barrel) as used herein refers to a motif in the secondary structure of a protein comprising two beta-strands (β-strands) in which the first strand is hydrogen bound to a second strand to form a closed structure. A "beta-beta-alpha structure" as used herein refers to a structure in a protein that consists of a β-barrel comprising two anti-parallel β-strands and one α-helix. The term "zinc finger DNA-binding domain" refers to a protein domain that comprises a zinc ion and is capable of binding to a specific three basepair DNA sequence. The term "non-natural zinc finger DNA-binding domain" refers to a zinc finger DNA-binding domain that does not occur in the cell or organism comprising the DNA which is to be modified.

The key amino acids within a zinc finger DNA-binding domain or motif that bind the three basepair sequence within the target DNA, are amino acids −1, +1, +2, +3, +4, +5 and +6 relative to the beginning of the alpha-helix (α-helix). The amino acids at position −1, +1, +2, +3, +4, +5 and +6 relative to the beginning of the α-helix of a zinc finger DNA-binding domain or motif can be modified while maintaining the beta-barrel (β-barrel) backbone to generate new DNA-binding domains or motifs that bind a different three basepair sequence. Such a new DNA-binding domain can be a non-natural zinc finger DNA-binding domain. In addition to the three basepair sequence recognition by the amino acids at position −1, +1, +2, +3, +4, +5 and +6 relative to the start of the α-helix, some of these amino acids can also interact with a basepair outside the three basepair sequence recognition site. By combining two, three, four, five, six or more zinc finger DNA-binding domains or motifs, a zinc finger protein can be generated that specifically binds to a longer DNA sequence. For example, a zinc finger protein comprising two zinc finger DNA-binding domains or motifs can recognize a specific six basepair sequence and a zinc finger protein comprising four zinc finger DNA-binding domains or motifs can recognize a specific twelve basepair sequence. A zinc finger protein can comprise two or more natural zinc finger DNA-binding domains or motifs or two or more non-natural zinc finger DNA-binding domains or motifs derived from a natural or wild-type zinc finger protein by truncation or expansion or a process of site-directed mutagenesis coupled to a selection method such as, but not limited to, phage display selection, bacterial two-hybrid selection or bacterial one-hybrid selection or any combination of natural and non-natural zinc finger DNA-binding domains. "Truncation" as used within this context refers to a zinc finger protein that contains less than the full number of zinc finger DNA-binding domains or motifs found in the natural zinc finger protein "Expansion" as used within this context refers to a zinc finger protein that contains more than the full number of zinc finger DNA-binding domains or motifs found in the natural zinc finger protein. Techniques for selecting a polynucleotide sequence within a genomic sequence for zinc finger protein binding are known in the art.

Methods for the design of zinc finger protein domains which bind specific nucleotide sequences which are unique to a target gene are known in the art. It has been calculated that a sequence comprising 18 nucleotides is sufficient to specify an unique location in the genome of higher organisms. Typically, therefore, zinc finger protein domains contain 6 zinc fingers, each with its specifically designed alpha helix for interaction with a particular triplet. However, in some instances, a shorter or longer nucleotide target sequence may be desirable. Thus, the zinc finger domains in the proteins may contain from 2 to 12 fingers—such as 3 to 8 fingers, 5 to 7 fingers, or 6 fingers.

Zinc finger proteins of use may comprise at least one zinc finger polypeptide linked via a linker, preferably a flexible linker, to at least a second DNA binding domain, which optionally is a second zinc finger polypeptide. The zinc finger protein may contain more than two DNA-binding domains, as well as one or more regulator domains. The zinc finger polypeptides may be engineered to recognize a selected target site in the gene of choice.

In one embodiment, the zinc finger protein comprises a framework (or backbone) derived from a naturally occurring zinc finger protein. Framework (or backbone) derived from any naturally occurring zinc finger protein can be used. For example, the zinc finger protein comprising a framework (or backbone) derived from a zinc finger protein comprising a C2H2 motif can be used.

In another specific embodiment, the zinc finger protein comprises a framework (or backbone) derived from a zinc finger protein that is naturally functional in plant cells. For example, the zinc finger protein may comprise a C3H zinc finger, a QALGGH motif, a RING-H2 zinc finger motif, a 9 amino acid C2H2 motif, a zinc finger motif of Arabidopsis LSD1 and a zinc finger motif of BBF/Dof domain proteins.

The zinc finger protein can be provided to the plant cells via any suitable methods known in the art. For example, the zinc finger protein can be exogenously added to the plant cells and the plant cells are maintained under conditions such that the zinc finger protein binds to the target nucleotide sequence and regulates the expression of the target gene in the plant cells. Alternatively, a nucleotide sequence encoding the zinc finger protein can be expressed in the plant cells and the plant cells are maintained under conditions such that the expressed zinc finger protein binds to the target nucleotide sequence and regulates the expression of the target gene in the plant cells.

The zinc finger gene may be expressed in a plant using any suitable plant expression vectors. Typical vectors useful for expression of genes in higher plants are well known in the art. In addition to regulatory domains, often the zinc finger protein can be expressed as a fusion protein with maltose binding protein ("MBP"), glutathione S transferase (GST), hexahistidine, c-myc, or the FLAG epitope, for ease of purification, monitoring expression, or monitoring cellular and subcellular localization.

In one embodiment, a mutated or non-naturally occurring plant or a mutated or non-naturally occurring plant cell is produced by zinc finger nuclease-mediated mutagenesis.

In a specific embodiment, a genomic DNA sequence comprising a part of or all of the coding sequence of NtMRP polynucleotide is modified by zinc finger nuclease mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together. The two zinc finger protein target sites can be 0, 1, 2, 3, 4, 5, 6 or more basepairs apart. The zinc finger protein binding site may be in the coding sequence of the NtMRP gene sequence or a regulatory element controlling the expression of the NtMRP gene, such as but not limited to the promoter region of the NtMRP gene. Particularly, one or both zinc finger proteins are non-natural zinc finger proteins.

Accordingly, the disclosure provides zinc finger proteins that bind to NtMRP polynucleotide. It is contemplated that a method for mutating a gene sequence, such as a genomic DNA sequence, that encodes the NtMRP gene by zinc finger nuclease-mediated mutagenesis comprises optionally one or more of the following steps: (i) providing at least two zinc finger proteins that selectively bind different target sites in the gene sequence; (ii) constructing two expression constructs each encoding a different zinc finger nuclease that comprises one of the two different non-natural zinc finger proteins of step (i) and a nuclease, operably linked to expression control sequences operable in a plant cell; (iii) introducing the two expression constructs into a plant cell wherein the two different zinc finger nucleases are produced, such that a double stranded break is introduced in the genomic DNA sequence in the genome of the plant cell, at or near to at least one of the target sites. The introduction of the two expression constructs into the plant cell can be accomplished simultaneously or sequentially, optionally including selection of cells that took up the first construct.

A double stranded break (DSB) as used herein, refers to a break in both strands of the DNA or RNA. The double stranded break can occur on the genomic DNA sequence at a site that is not more than between 5 base pairs and 1500 base pairs, particularly not more than between 5 base pairs and 200 base pairs, particularly not more than between 5 base pairs and 20 base pairs removed from one of the target sites. The double stranded break can facilitate non-homologous end joining leading to a mutation in the genomic DNA sequence at or near the target site. "Non homologous end joining (NHEJ)" as used herein refers to a repair mechanism that repairs a double stranded break by direct ligation without the need for a homologous template, and can thus be mutagenic relative to the sequence before the double stranded break occurs.

The method can optionally further comprise the step of (iv) introducing into the plant cell a polynucleotide comprising at least a first region of homology to a nucleotide sequence upstream of the double-stranded break and a second region of homology to a nucleotide sequence downstream of the double-stranded break. The polynucleotide can comprise a nucleotide sequence that corresponds to the NtMRP polynucleotide sequence that contains a deletion or an insertion of heterologous nucleotide sequences. The polynucleotide can thus facilitate homologous recombination at or near the target site resulting in the insertion of heterologous sequence into the genome or deletion of genomic DNA sequence from the genome. The resulting genomic DNA sequence in the plant cell can comprise a mutation that disrupts the enzyme activity of an expressed mutant NtMRP protein, a early translation stop codon, or a sequence motif that interferes with the proper processing of pre-mRNA into an mRNA resulting in reduced expression or inactivation of the gene. Methods to disrupt protein synthesis by mutating a gene sequence coding for a protein are known to those skilled in the art.

A zinc finger nuclease may be constructed by making a fusion of a first polynucleotide coding for a zinc finger protein that binds to NtMRP polynucleotide, and a second polynucleotide coding for a non-specific endonuclease such as, but not limited to, those of a Type IIS endonuclease. A Type IIS endonuclease is a restriction enzyme having a separate recognition domain and an endonuclease cleavage domain wherein the enzyme cleaves DNA at sites that are removed from the recognition site. Non-limiting examples of Type IIS endonucleases can be, but not limited to, AarI, BaeI, CdiI, DrdII, EciI, FokI, FauI, GdiII, HgaI, Ksp632I, MboII, Pfl1108I, Rle108I, RIeAI, SapI, TspDTI or UbaPI.

Methods for the design and construction of fusion proteins, methods for the selection and separation of the endonuclease domain from the sequence recognition domain of a Type IIS endonuclease, methods for the design and construction of a zinc finger nuclease comprising a fusion protein of a zinc finger protein and an endonuclease, are known in the art. In a specific embodiment, the nuclease domain in a zinc finger nuclease is FokI. A fusion protein between a zinc finger protein and the nuclease of FokI may comprise a spacer consisting of two basepairs or alternatively, the spacer can consist of three, four, five, six or more basepairs. In one embodiment, there is described a fusion protein with a seven basepair spacer such that the endonuclease of a first zinc finger nuclease can dimerize upon contacting a second zinc finger nuclease, wherein the two zinc finger proteins making up said zinc finger nucleases can bind upstream and downstream of the target DNA sequence. Upon dimerization, a zinc finger nuclease can introduce a double stranded break in a target nucleotide sequence which may be followed by non-homologous end joining or homologous recombination with an exogenous nucleotide sequence having homology to the regions flanking both sides of the double stranded break.

In yet another embodiment, there is provided a fusion protein comprising a zinc finger protein and an enhancer protein resulting in a zinc finger activator. A zinc finger activator can be used to up-regulate or activate transcription of the NtMRP gene, comprising the steps of (i) engineering a zinc finger protein that binds a region within a promoter or a sequence operatively linked to a coding sequence of the NtMRP gene, (ii) making a fusion protein between said zinc finger protein and a transcription activator, (iii) making an expression construct comprising a polynucleotide sequence coding for said zinc finger activator under control of a promoter active in a cell, such as plant cell, (iv) introducing said gene construct into the cell, and (v) culturing the cell and allowing the expression of the zinc finger activator, and (vi) characterizing the cell having an increased expression of NtMRP protein.

In yet another embodiment, the disclosure provides a fusion protein comprising a zinc finger protein and a gene repressor resulting in a zinc finger repressor. A zinc finger repressor can be used to down-regulate or repress the transcription of NtMRP polynucleotide, comprising the steps of (i) engineering a zinc finger protein that binds to a region within a promoter or a sequence operatively linked to NtMRP polynucleotide, and (ii) making a fusion protein between said zinc finger protein and a transcription repressor, and (iii) developing a gene construct comprising a polynucleotide sequence coding for said zinc finger repressor under control of a promoter active in a cell, such as a plant cell, and (iv) introducing said gene construct into the cell, and (v) providing for the expression of the zinc finger repressor, and (vi) characterizing the cell having reduced transcription of NtMRP polynucleotide.

In yet another embodiment, the disclosure provides a fusion protein comprising a zinc finger protein and a methylase resulting in a zinc finger methylase. The zinc finger methylase may be used to down-regulate or inhibit the expression of NtMRP polynucleotide in a cell, such as plant cell, by methylating a region within the promoter region of NtMRP polynucleotide, comprising the steps of (i) engineering a zinc finger protein that can binds to a region within a promoter of NtMRP polynucleotide, and (ii) making a fusion protein between said zinc finger protein and a methylase, and (iii) developing a gene construct containing a polynucleotide coding for said zinc finger methylase under control of a promoter active in the cell, and (iv) introducing said gene construct into the cell, and (v) allowing the expression of the zinc finger methylase, and (vi) characterizing the cell having reduced or essentially no expression of NtMRP protein in the cell.

In various embodiments, a zinc finger protein may be selected according to methods described herein to bind to a regulatory sequence of NtMRP polynucleotide. More specifically, the regulatory sequence may comprise a transcription initiation site, a start codon, a region of an exon, a boundary of an exon-intron, a terminator, or a stop codon. The zinc finger protein can be fused to a nuclease, an activator, or a repressor protein.

In various embodiments, a zinc finger nuclease introduces a double stranded break in a regulatory region, a coding region, or a non-coding region of a genomic DNA sequence of NtMRP polynucleotide, and leads to a reduction, an inhibition or a substantial inhibition of the level of expression of NtMRP polynucleotide, or a reduction, an inhibition or a substantial inhibition of the activity of the protein encoded thereby.

The disclosure also provides a method for modifying a cell, such as a plant cell, wherein the genome of the plant cell is modified by zinc finger nuclease-mediated mutagenesis, comprising (a) identifying and making at least two non-natural zinc finger proteins that selectively bind different target sites for modification in the genomic nucleotide sequence; (b) expressing at least two fusion proteins each comprising a nuclease and one of the at least two non-natural zinc finger proteins in the plant cell, such that a double stranded break is introduced in the genomic nucleotide sequence in the plant genome, particularly at or close to a target site in the genomic nucleotide sequence; and, optionally (c) introducing into the cell a polynucleotide comprising a nucleotide sequence that comprises a first region of homology to a sequence upstream of the double-stranded break and a second region of homology to a region downstream of the double-stranded break, such that the polynucleotide recombines with DNA in the genome. Also described, are cells comprising one or more expression constructs that comprise nucleotide sequences that encode one or more of the fusion proteins.

In another aspect, the disclosure further provides methods for producing mutant, non-naturally occurring or transgenic or otherwise genetically-modified plants using meganucleases—such as I-CreI. Naturally occurring meganucleases as well as recombinant meganucleases can be used to specifically cause a double-stranded break at a single site or at relatively few sites in the genomic DNA of a plant to allow for the disruption of a NtMRP gene. The meganuclease may be an engineered meganuclease with altered DNA-recognition properties. Meganuclease proteins can be delivered into plant cells by a variety of different mechanisms known in the art. The meganuclease may be an engineered meganuclease with altered DNA-recognition properties. This citation describes methods for the structure-based engineering of meganucleases derived from the naturally-occurring meganuclease I-CreI. These engineered meganucleases can be made to recognize and cut pre-determined 22 base pair DNA sequences found in the genomes of plants. Meganuclease proteins can be delivered into plant cells by a variety of different mechanisms known in the art.

Aspects of the disclosure allow for the use of meganucleases to inactivate NtMRP polynucleotide in a plant cell or plant. Aspects also relate to a method for inactivating NtMRP polynucleotide in a plant using a meganuclease comprising: (a) providing a plant cell comprising NtMRP polynucleotide; (b) introducing a meganuclease or a construct encoding a meganuclease into said plant cell; and (c) allowing the meganuclease to inactivate NtMRP polynucleotide.

Meganucleases can be used to cleave meganuclease recognition sites within the coding regions of NtMRP polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification.

Following delivery of the meganuclease expression cassette, plant cells are grown, initially, under conditions that are typical for the particular transformation procedure that was used. This may mean growing transformed cells on media at temperatures below 26.degree. C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove NtMRP polynucleotide from the genome of a plant. Such applications are possible using a pair of engineered meganucleases, each of which cleaves a meganuclease recognition site on either side of the intended deletion. Recombinant constructs provided herein can be used to transform plants or plant cells in order to modulate (for example, reduce or inhibit) NtMRP protein expression levels. A recombinant polynucleotide construct can comprise a polynucleotide encoding a NtMRP polypeptide as described herein, operably linked to a regulatory region suitable for expressing the NtMRP polypeptide in the plant or cell. Thus, a polynucleotide can comprise a coding sequence that encodes the NtMRP polypeptide as described herein or a variant thereof.

The NtMRP polypeptide encoded by a recombinant polynucleotide can be a native NtMRP polypeptide, or can be heterologous to the cell. In some cases, the recombinant construct contains a polynucleotide that reduces or inhibits expression of a NtMRP-modulating polypeptide(s), operably linked to a regulatory region. Examples of suitable regulatory regions are described herein.

Vectors containing recombinant polynucleotide constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available.

The vectors can also include, for example, origins of replication, scaffold attachment regions (SARs) or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, .beta.-glucuronidase (GUS), green fluorescent protein (GFP), glutathione S-transferase (GST), polyhistidine, c-myc or hemagglutinin sequences typically are expressed as a fusion with the encoded polypeptide. Such tags can be inserted anywhere within the polypeptide, including at either the carboxyl or amino terminus.

Various embodiments are directed to mutant, non-naturally occurring or transgenic plants that are modified to reduce the NtMRP gene expression level by various methods that can utilized for reducing or silencing NtMRP gene expression, and thereby, producing plants in which the expression level of NtMRP transporters can be reduced within plant tissues of interest. Rates of heavy metal transport and distribution patterns of heavy metal transport, in particular, cadmium transport, can be altered in plants produced according to the disclosed methods and compositions.

Plants suitable for use in genetic modification include monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (*eucalyptus*), *Triticosecale* (*triticum* wheat times rye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), *Musa paradisiaca* (banana), Solanum tuberosum (potato), Brassica oleracea (broccoli, cauliflower, Brussels sprouts), Camellia sinensis (tea), Fragaria ananassa (strawberry), Theobroma cacao (cocoa), Coffea arabica (coffee), Vitis vinifera (grape), Ananas comosus (pineapple), Capsicum annum (hot & sweet pepper), Allium cepa (onion), Cucumis melo (melon), Cucumis sativus (cucumber), Cucurbita maxima (squash), Cucurbita moschata (squash), Spinacea oleracea (spinach), Citrullus lanatus (watermelon), Abelmoschus esculentus (okra), Solanum melongena (eggplant), Rosa spp. (rose), Dianthus caryophyllus (carnation), Petunia spp. (petunia), Poinsettia pulcherrima (poinsettia), Lupinus albus (lupin), Uniola paniculata (oats), bentgrass (Agrostis spp.), Populus tremuloides (aspen), Pinus spp. (pine), Abies spp. (fir), Acer spp. (maple), Hordeum vulgare (barley), Poa pratensis (bluegrass), Lolium spp. (ryegrass) and Phleum pratense (timothy), Panicum virgatum (switchgrass), Sorghum bicolor (sorghum, sudangrass), Miscanthus giganteus (miscanthus), Saccharum sp. (energycane), Populus balsamifera (poplar), Zea mays (corn), Glycine max (soybean), Brassica napus (canola), Triticum aestivum (wheat), Gossypium hirsutum (cotton), Oryza sativa (rice), Helianthus annuus (sunflower), Medicago sativa (alfalfa), Beta vulgaris (sugarbeet), or Pennisetum glaucum (pearl millet).

Various embodiments are directed to mutant plants, non-naturally occurring plants or transgenic plants modified to modulate (for example, reduce or inhibit) NtMRP gene expression levels thereby, producing plants—such as tobacco plants—in which the expression level of NtMRP is reduced within plant tissues of interest as compared to a control plant. The disclosed compositions and methods can be applied to any species of the genus Nicotiana, including N. rustica and N. tabacum (for example, LA B21, LN KY171, TI 1406, Basma, Galpao, Perique, Beinhart 1000-1, and Petico). Other species include N. acaulis, N. acuminata, N. acuminata var. multiflora, N. africana, N. alata, N. amplexicaulis, N. arentsii, N. attenuata, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis subsp. hesperis, N. otophora, N. paniculata, N. pauciflora, N. petunioides, N. plumbaginifolia, N. quadrivalvis, N. raimondii, N. repanda, N. rosulata, N. rosulata subsp. ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides, and N.×sanderae.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful Nicotiana tabacum varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KTY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B 13P, Xanthi (Mitchell-Mor), Bel-W3, 79-615, Samsun Holmes NN, KTRDC number 2 Hybrid 49, Burley 21, KY 8959, KY 9, MD 609, PG 01, PG 04, PO1, PO2, PO3, RG 11, RG 8, VA 509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

In a further aspect, there is provided a mutant, non-naturally occurring or transgenic plant as described herein which has been further modified such that expression of NtHMA transporters is also reduced which may further reduce the content of cadmium in the plant. The use of NtHMA transporters to reduce the content of cadmium in the plant is described in WO2009074325. This, according to one embodiment there is provided a mutant, non-naturally occurring or transgenic plant cell comprising an isolated NtMRP polynucleotide, a NtMRP chimeric gene, a NtMRP polynucleotide construct, a NtMRP double-stranded RNA, a NtMRP conjugate and/or an NtMRP expression vector together with an isolated NtHMA polynucleotide, a NtHMA chimeric gene, a NtHMA polynucleotide construct, a NtHMA double-stranded RNA, a NtHMA conjugate and/or an NtHMA expression vector.

Embodiments are also directed to compositions and methods for producing mutant plants, non-naturally occurring plants, hybrid plants, or transgenic plants that have been modified to modulate (for example, reduce or inhibit) NtMRP expression or activity so that lower amounts of cadmium are accumulated therein as compared to a control. In certain embodiments, the plants that are obtained are similar or substantially the same in overall appearance (for example, phenotype) to control plants. Various phenotypic characteristics such as degree of maturity, number of leaves per plant, stalk height, leaf insertion angle, leaf size (width and length), internode distance, and lamina-midrib ratio can be assessed by field observations. In a preferred embodiment, the height or weight, or height and weight of the plants, is substantially the same as the control plants. In another preferred embodiment, no significant differences are found in dried collected leaves of the plants as compared to a control thus indicating that the modulation of NtMRP transcripts has no statistically relevant effect on dry biomass.

One aspect is a seed of the mutant plant, the non-naturally occurring plant, the hybrid plant or the transgenic plant. Preferably, the seed is a tobacco seed. A further aspect is pollen or an ovule of the mutant plant, the non-naturally occurring plant, the hybrid plant or the transgenic plant. In addition, a mutant plant, a non-naturally occurring plant, a hybrid plant, a transgenic plant is described which further comprises a polynucleotide conferring male sterility.

The disclosure also provides a tissue culture of regenerable cells of the mutant plant, non-naturally occurring plant, hybrid plant, or transgenic plant or a part thereof, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

In some embodiments, a plant in which expression of NtMRP polynucleotide is modulated (for example, reduced or inhibited) can have decreased levels of heavy metal—such as cadmium—especially in the leaves. The cadmium level can be decreased by at least about 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 70%, 80%, 90%, 95%, 96%, 97%, 98% or 99% or more—such as 100%, 125%, 150% or 200% or more as compared to the cadmium level in a corresponding control plant in which expression of NtMRP polynucleotide has not been modulated (for example, reduced or inhibited). In some embodiments, a plant in which expression of NtMRP polynucleotide is modulated (for example, reduced or inhibited) can have increased or decreased levels of cadmium in the roots. In some embodiments, a plant in which expression of NtMRP polynucleotide is modulated (for example, reduced or inhibited) can have decreased or increased levels of cadmium in the roots and decreased levels of cadmium in leaves. In some embodiments, a plant in which expression of NtMRP polynucleotide is modulated (for example, reduced or inhibited) can have decreased levels of cadmium in harvestable biomass.

Expression can be evaluated using methods including, for example, RT-PCR, Northern blots, RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, for example, at a particular time in development or upon induction, expression can be evaluated selectively at a desired time period.

A population of mutant, non-naturally occurring or transgenic plants can be screened or selected for those members of the population that have a desired trait or phenotype. For example, a population of progeny of a single transformation event can be screened for those plants having a desired level of expression of NtMRP polypeptide or polynucleotide. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides or polynucleotides.

A population of plants can be screened for those plants having a desired trait, such as a modulated (for example, reduced or inhibited) level of cadmium. Selection or screening can be carried out over one or more generations, or in more than one geographic locations. In some cases, mutant, non-naturally occurring or transgenic plants can be grown and selected under conditions which induce a desired phenotype or are otherwise necessary to produce a desired phenotype in a mutant, non-naturally occurring or transgenic plant. In addition, selection or screening can be applied during a particular developmental stage in which the phenotype is expected to be exhibited by the plant. Selection or screening can be carried out to choose those mutant, non-naturally occurring or transgenic plants having a statistically significant difference in their cadmium content relative to a control plant that in which the expression or activity of NtMRP polynucleotide or protein has not been modulated (for example, reduced or inhibited).

Mutant, non-naturally occurring or transgenic plant cells and plants are described herein comprising one or more recombinant polynucleotides—such as the isolated polynucleotide, the chimeric gene, the polynucleotide construct, the double-stranded RNA, the conjugate or the expression vector. A plant or plant cell can be transformed by having the recombinant polynucleotide integrated into its genome to become stably transformed. Stably transformed cells typically retain the introduced polynucleotide with each cell division. A plant or plant cell may also be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions.

Techniques for introducing polynucleotides into monocotyledonous and dicotyledonous plants are known in the art, and include, for example, *Agrobacterium*-mediated transformation, viral vector-mediated transformation, electroporation and particle gun transformation. The *Agrobacterium* system for integration of foreign polynucleotide into plant chromosomes has been extensively studied, modified, and exploited for plant genetic engineering. Naked recombinant polynucleotide molecules comprising polynucleotide sequences corresponding to the subject purified protein operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard. Alternatively, such vectors comprising recombinant polynucleotide molecules encoding the subject purified protein are introduced into live *Agrobacterium* cells, which then transfer the polynucleotide into the plant cells. Transformation by naked polynucleotide without accompanying T-DNA vector sequences can be accomplished via fusion of protoplasts with polynucleotide-containing liposomes or via electroporation. Naked polynucleotide unaccompanied by T-DNA vector sequences can also be used to transform cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic polynucleotide are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling NtMRP RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease. Suitable anther-specific promoters can be used. Suitable root-preferred promoters known to persons skilled in the art may be selected. Suitable seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gama-zein is an endosperm-specific promoter. Glob-1 is an embryo-specific promoter. For dicots, seed-specific promoters include, but are not limited to, bean .beta.-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa γ-zein promoter (such as gzw64A promoter, see Genbank Accession number S78780), a waxy promoter, a shrunken 1 promoter, a shrunken 2 promoter, a globulin 1 promoter (see Genbank Accession number L22344), an ltp2 promoter, cim1 promoter, maize end1 and end2 promoters, nuc1 promoter, Zm40 promoter, eep1 and eep2; led, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

Examples of conjugated moieties include macromolecular compounds such as proteins (for example, antibodies), fatty acid chains, sugar residues, glycoproteins, polymers (for example, polyethylene glycol), or combinations thereof. An oligonucleotide may be conjugated to a moiety that increases cellular uptake of the oligonucleotide.

Non-limiting examples of moieties include, but are not limited to, antibodies, polypeptides, lipid moieties such as a cholesterol moiety, cholic acid, a thioether, for example, Hexyl-s-tritylthiol, a thiocholesterol, an aliphatic chain, for example, dodecandiol or undecyl residues, a phospholipid, for example, di-hexadecyl-rac-glycerol or triethylammonium 1-di-o-hexadecyl-rac-glycero-S-h-phosphonate, a polyamine or a polyethylene glycol chain, an adamantane acetic acid, a palmityl moiety, an octadecylamine or hexy-lamino-carbonyl-oxycholesterol moiety.

The moiety may be a positively charged polymer—such as a positively charged peptide that is, for example, about 1 to 50 amino acid residues in length or polyalkylene oxide such as polyethylene glycol (PEG) or polypropylene glycol. Suitably the positively charged polymer, such as a polyalkylene oxide may be attached to the oligomer via a linker such as a releasable linker.

When NtMRP polypeptide expression is being measured, detecting the amount of mRNA encoding an NtMRP polypeptide in the cell can be quantified by, for example, PCR or Northern blot. Where a change in the amount of NtMRP polypeptide in the sample is being measured, detecting NtMRP by use of anti-NtMRP antibodies can be used to quantify the amount of NtMRP polypeptide in the cell using known techniques. Alternatively the biological activity (for example, heavy metal—such as cadmium—transport) can be measured before and after contact with the test agent.

In another embodiment, antibodies that are immunoreactive with the polypeptides are provided herein. The NtMRP polypeptides, fragments, variants, fusion polypeptides, and the like, as set forth herein, can be employed as "immunogens" in producing antibodies immunoreactive therewith. Such antibodies specifically bind to the polypeptides via the antigen-binding sites of the antibody. Specifically binding antibodies are those that will specifically recognize and bind with NtMRP family polypeptides, homologues, and variants, but not with other molecules. In one embodiment, the antibodies are specific for polypeptides having an NtMRP amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with an NtMRP polypeptide, fragment, variant, or mutants thereof. Such host animals may include, but are not limited to, rabbits, mice, and rats, to name a few. Various adjutants may be used to increase the immunological response. Depending on the host species, such adjutants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Various embodiments provide mutant, non-naturally occurring or transgenic plants, as well as biomass and seeds in which the expression level of NtMRP polynucleotide is substantially reduced to curtail or impede cadmium transport into the leaf lamina. The leaf lamina can be incorporated into various consumable products—such as various smokable articles, such as cigars, cigarettes, and smokeless tobacco products (that is, non-combustible).

The % cadmium reduction in these smokable articles and smokeless products may be a value of at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%, 200% or 300% lower, when compared to consumable products derived from non-mutant, non-naturally occurring or non-transgenic counterparts. In some embodiments, the cadmium content of these smokable articles and smokeless products is a value from a range from about 0.01 to about 0.05 parts per million (ppm), from about 0.01 to about 0.1 ppm, from about 0.01 to about 0.5 ppm, from about 0.01 to about 1.0 ppm, or from about 0.01 to about 5 ppm. In some embodiments, the cadmium content of these smokable articles and smokeless products is about 0.001 ppm or less, about 0.01 ppm or less or about 0.05 ppm or less, or about 0.49 ppm or less or about 0.5 ppm or less. The degree of cadmium accumulation in plants can be substantially variable depending on several parameters attributed to the complexity of the genotype and the growth environment. For example, cadmium concentrations in field-grown tobacco leaves can be extremely variable depending on factors such as the agro-climate, soil quality, cultivars, and the type and origin of fertilizer used. Furthermore, the relative cadmium distribution patterns within different portions of a tobacco plant can vary according to the species, the organ/tissue, and growth conditions (that is, field-grown vs. hydroponically-grown). On average, the cadmium concentrations measured in field-grown tobacco leaves (including midribs and veins) can be in the range from approximately 0.5 to 5 ppm (parts per million, or microgram/gram of dry weight of tobacco leaves). However, many published cadmium levels typically do not define the tobacco maturity stage, the tobacco variety, or the particular leaf portions (that is, removal from leaf stalk position) harvested for analysis. In some varieties, the lower leaves may accumulate higher cadmium levels than the medium and upper leaves. At the intracellular level, cadmium can be found in various cell components of a plant cell, including the cell wall, cytoplasm, chloroplast, nucleus, and vacuoles.

Furthermore, cadmium content measured in tobacco leaves can vary substantially depending on the cadmium levels in the soil environment where the tobacco plants were grown. The leaves of tobacco grown in cadmium-contaminated areas can accumulate cadmium from about 35 ppm or higher, compared to the leaves of genetically identical counterparts grown in non-contaminated areas, which can accumulate cadmium at a range from approximately 0.4 to approximately 8 ppm. The vacuoles within the leaves of plants grown in cadmium-contaminated areas can accumulate very high cadmium concentrations. Methods for applying the disclosed compositions to be suitable for a given plant species of interest are known to persons skilled in the art.

Heavy metal content in plants may be measured using various methods known in the art. A preferred method comprises the use of inductively coupled plasma-mass spectrophotometry ("ICP-MS," Agilent 7500A; Agilent Technologies, Palo Alto, Calif.).

The mutant, non-naturally occurring or transgenic plants that are described herein may have other uses in, for example, agriculture. For example, mutant, non-naturally occurring or transgenic plants described herein can be used to make animal feed and human food products. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the packaging material, or a label inserted within the package, that describes the nature of the seeds therein.

A plant carrying a mutant NtMRP allele can be used in a plant breeding program to create useful lines, varieties and hybrids. In particular, the mutant NtMRP allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprises crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants.

In one embodiment, a method is provided for producing a non-naturally occurring plant comprising: (a) crossing a mutant or transgenic plant with a second plant to yield progeny seed; (b) growing the progeny seed, under plant growth conditions, to yield the non-naturally occurring plant. The method may further comprise: (c) crossing the previous generation of non-naturally occurring plant with itself or another plant to yield progeny seed; (d) growing the progeny seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly tobacco plant breeding, are well known and can be used in the methods described herein. The disclosure further provides non-naturally occurring plants produced by these methods.

In some embodiments of methods described herein, lines resulting from breeding and screening for variant NtMRP genes are evaluated in the field using standard field procedures. Control genotypes including the original unmutagenised parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of the NtMRP gene(s) into other tobaccos, as described herein. For example, a breeder can create segregating populations from hybridizations of a genotype containing a mutant allele with an agronomically desirable genotype. Plants in the F2 or backcross generations can be screened using a marker developed from a NtMRP genomic sequence(s) or a fragment(s) thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant NtMRP gene expression (for example, the null version of the NtMRP gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant NtMRP gene expression. In some embodiments, a plant population in the F2 generation is screened for variant NtMRP gene expression, for example, a plant is identified that fails to express NtMRP due to the absence of a NtMRP gene according to standard methods, for example, by using a PCR method with primers based upon the nucleotide sequence information for NtMRP described herein.

Hybrid varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression of NtMRP polypeptide or polynucleotide. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides or polynucleotides.

Mutant, non-naturally occurring or transgenic plant cells and plants are described herein comprising one or more recombinant polynucleotides—such as one or more isolated NtMRP polynucleotides, one or more polynucleotide constructs, one or more double-stranded RNAs, one or more conjugates or one or more vectors/expression vectors.

Expression of NtMRP can be evaluated using methods including, for example, RT-PCR, Northern blots, RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, for example, at a particular time in development or upon induction, expression can be evaluated selectively at a desired time period.

Without limitation, the plants described herein may be modified for other purposes either before or after the expression or activity of NtMRP has been modulated (for example, reduced or inhibited). One or more of the following genetic modifications can be present in the mutant, non-naturally occurring or the transgenic plants. In one embodiment, one or more further genes that are involved in heavy metal uptake or heavy metal transport is modified resulting in plants or parts of plants (such as leaves) having a lower heavy metal content than control plants or parts thereof without the modification(s). Non-limiting examples include genes in the family of cation diffusion facilitators (CDF), the family of Zrt-, Irt-like proteins (ZIP), the family of cation exchangers (CAX), the family of copper transporters (COPT), the family of heavy-metal P-type ATPases (HMAs, as described in WO2009074325), the family of homologs of natural resistance-associated macrophage proteins (NRAMP), and another member of the family of ATP-binding cassette (ABC) transporters, which participate in transport of heavy metals, such as cadmium. The term heavy metal as used herein includes transition metals. In another embodiment, one or more genes that are involved in the conversion of nitrogenous metabolic intermediates is modified resulting in plants or parts of plants (such as leaves) that when heated, produces lower levels of at least one tobacco-specific nitrosamine (for example, 4-(methylnitrosamino)-1-(3-pyridyl)-1-butanone, N-nitrosonornicotine, N-nitrosoanatabine, and N-nitrosoanabasine) than control plants or parts thereof. Non-limiting examples of genes that can be modified include genes encoding a nicotine demethylase, such as CYP82E4, CYP82E5 and CYP82E10 which participate in the conversion of nicotine to nornicotine and are described in WO2006091194, WO2008070274, WO2009064771 and PCT/US2011/021088.

Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Another exemplary modification results in plants that produce proteins which have favourable immunogenic properties for use in humans. For example, plants capable of producing proteins which substantially lack alpha-1,3-linked fucose residues, beta-1,2-linked xylose residues, or both, in its N-glycan may be of use. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

Without limitation, the plants described herein may be further modified. Examples of such further modifications include, but are not limited to: (a) Plants that can tolerate herbicides. For example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*); Sulphonylurea resistant plants have been produced by transforming the mutant ALS (acetolactate synthetase) gene from *Arabidopsis*; OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*; (b) Plants are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects; (c) Plants that are resistant to virus. Tobacco Mosaic Virus plants have been produced by introducing viral coat proteins. Other viral resistant transgenic plants include potato virus resistant potato plants, RSV resistant rice, and YMV resistant black gram and green gram; (d) Plants that are resistant to bacteria. Plants expressing the Xa21 gene (resistance to bacterial blight) with plants expressing both a Bt fusion gene and a chitinase gene (resistance to yellow stem borer and tolerance to sheath) have been engineered; (e) Stress tolerant transgenic plants: Cold and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance; (f) Plants that produce proteins that have favourable immunogenic properties for use in humans. For example, plants capable of producing proteins which substantially lack alpha-1,3-linked fucose residues, beta-1,2-linked xylose residues, or both, in its N-glycan may be of use; and (g) Other examples of transgenic plants are plants with improved storage proteins and oils, plants with enhanced photosynthetic efficiency, plants with prolonged self life, plants with enhanced carbohydrate content and plants resistant to fungi; plants encoding an enzyme involved in the biosynthesis of alkyloids; genes for a bacterial organic mercury detoxification pathway (mercuric reductase, merA) and organomercurial lyase, merB were combined by crossing in *Arabidopsis*, and plants expressing both genes were able to grow on 50-fold higher methylmercury concentrations than wild-type plants.

One or more such traits may be introgressed into the mutant, non-naturally occurring or transgenic tobacco plants from another tobacco cultivar or may be directly transformed into it. The introgress ion of the trait(s) into the mutant, non-naturally occurring or transgenic tobacco plants may be achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y 761 pp.). Molecular biology-based techniques described above, in particular RFLP and microsatellite markers, can be used in such backcrosses to identify the progenies having the highest degree of genetic identity with the recurrent parent. This permits one to accelerate the production of varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the polynucleotide(s) being transferred. The resulting plants generally have essentially all of the morphological and physiological characteristics of the mutant, non-naturally occurring or transgenic plants, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Various embodiments provide mutant plants, non-naturally occurring plants or transgenic plants, as well as biomass in which the expression level of NtMRP polynucleotide is reduced so that lower amounts of cadmium are accumulated therein.

Parts of the such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured material from the mutant, transgenic and non-naturally occurring tobacco plants described herein. Processes of curing green tobacco leaves are known by those having skills in the art and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco-containing aerosol forming materials comprising leaves, preferably cured leaves, from the mutant tobacco plants, transgenic tobacco plants or non-naturally occurring tobacco plants described herein. The tobacco products described herein can be a blended tobacco product which may further comprise unmodified tobacco.

The mutant, non-naturally occurring or transgenic plants may have other uses in, for example, agriculture. For example, mutant, non-naturally occurring or transgenic plants described herein can be used to make animal feed and human food products.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the packaging material, or a label inserted within the package, that describes the nature of the seeds therein.

Compositions, methods and kits for genotyping plants for identification, selection, or breeding are encompassed by the disclosure and can comprise a means of detecting the presence of a NtMRP polynucleotide in a sample of polynucleotide. Accordingly, a composition is described comprising one of more primers for specifically amplifying at least a portion of NtMRP polynucleotide and optionally one or more probes and optionally one or more reagents for conducting the amplification or detection.

Accordingly, gene specific oligonucleotide primers or probes comprising about 10 or more contiguous polynucleotides corresponding to the NtMRP polynucleotide are disclosed. Said primers or probes may comprise or consist of about 15, 20, 25, 30, 40, 45 or 50 more contiguous polynucleotides that hybridise (for example, specifically hybridise) to the NtMRP polynucleotide. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in polynucleotide amplification or detection). The one or more specific primers or probes can be designed and used to amplify or detect a part or all of the NtMRP polynucleotide. By way of specific example, two primers may be used in a polymerase chain reaction protocol to amplify a polynucleotide fragment encoding NtMRP polynucleotide—such as DNA or RNA. The polymerase chain reaction may also be performed using one primer that is derived from the NtMRP polynucleotide sequence and a second primer that hybridises to a sequence upstream or downstream of the NtMRP polynucleotide sequence—such as a NtMRP promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a product made or derived from the plant, the plant cell or the plant material as described herein.

Thus, in a further aspect, there is also provided a method of detecting a NtMRP polynucleotide in a sample comprising the step of: (a) providing a sample comprising, or suspected of comprising, a polynucleotide; (b) contacting said sample with one of more primers or one or more probes for specifically detecting at least a portion of the NtMRP polynucleotide; and (c) detecting the presence of an amplification product, wherein the presence of an amplification product is indicative of the presence of the NtMRP polynucleotide in the sample. In a further aspect, there is also provided the use of one of more primers or probes for specifically detecting at least a portion of NtMRP polynucleotide. Kits for detecting at least a portion of the NtMRP polynucleotide are also provided which comprise one of more primers or probes for specifically detecting at least a portion of NtMRP polynucleotide. The kit may comprise reagents for polynucleotide amplification—such as polymerase chain reaction (PCR)—or reagents for polynucleotide probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and/or instructions for determining heavy metal—such as cadmium—content. In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a NtMRP polynucleotide. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, a means to follow segregation of NtMRP as well as chromosomal sequences genetically linked to these genes or polynucleotides using such techniques as AFLP analysis is described.

The invention will be further described in the following examples, which are not intended to limit the scope of the invention described in the claims.

EXAMPLES

The following examples are provided as an illustration and not as a limitation. Unless otherwise indicated, conventional techniques and methods of molecular biology, plant biology, bioinformatics, and plant breeding are employed.

Example 1

Identification of the Genomic Sequence of NtMRP3 DNA

Tobacco BAC library. A Bacterial Artificial Chromosome (BAC) library is prepared as follows: nuclei are isolated from leaves of greenhouse grown plants of the *Nicotiana tabacum* variety Hicks Broad Leaf. High-molecular weight DNA is isolated from the nuclei according to standard protocols and partially digested with BamHI and HindIII and cloned in the BamHI or Hindi II sites of the BAC vector pINDIGO5. More than 320,000 clones are obtained with an average insert length of 135 mega basepairs covering approximately 9.7 times the tobacco genome.

Tobacco genome sequence assembly. A large number of randomly-picked BAC clones are submitted to sequencing using the Sanger method generating more than 1,780,000 raw sequences of an average length of 550 basepairs. Methyl filtering is applied by using a Mcr+ strain of *Escherichia coli* for transformation and isolating only hypomethylated DNA. All sequences are assembled using the CELERA genome assembler yielding more than 800,000 sequences comprising more than 200,000 contigs and 596,970 single sequences. Contig sizes are between 120 and 15,300 basepairs with an average length of 1,100 basepairs.

The genomic sequence of NtMRP3 DNA is identified by sequencing a BAC containing part of the genome which includes NtMRP3 DNA. The sequence is set forth in FIG. 6.

Example 2

Transformation of Tobacco Varieties with NtMRP3 RNAi Expression Vectors

Tobacco seeds are sterilized and germinated in a petri dish containing MS basal media supplemented with 5 ml/L plant preservative mixture (PPM). Seedlings, at approximately 7 to 10 days post-germination, are selected for transformation with various NtMRP3 RNAi expression vectors. A single colony of *Agrobacterium tumefaciens* LBA4404 is inoculated into a liquid LB medium containing 50 mg l$^{-1}$ kanamycin (kanamycin mono sulphate), and is incubated for 48 h at 28° C. with reciprocal shaking (150 cycles min$^{-1}$). Cultured cells are collected by centrifugation (6000×g, 10 min), and are suspended to a final density of 0.4-0.7 OD$_{600}$, with 20 ml liquid MS medium containing 20 g$^{-1}$ sucrose. The 7-10 day seedling explants are immersed into a bacterial suspension for 5 mins, and are blotted on sterile filter papers. Fifty explants are placed onto 40 ml aliquots of REG agar medium (MS basal medium supplemented with 0.1 mg l$^{-1}$ 1-naphthaleneacetic acid (NAA) and 1 mg l$^{-1}$ benzylaminopurine (BAP)) in 100 mm×20 mm petri dishes. The explants are co-cultivated with *Agrobacterium* at 25° C. After 3 days of co-cultivation, the explants are washed and transferred to RCPK medium (REG medium with 100 mg$^{-1}$ kanamycin, 500 mg l$^{-1}$ carbenicillin, and 5 ml PPM) to select for transformants. The explants are subcultured every 2 weeks. After 8-12 weeks of growth under selective conditions, the surviving plants, representing transformants that have integrated the NtMRP3 RNAi expression constructs into their genomes are transferred to a rooting medium (MS basal medium supplemented with 100 mg l$^{-1}$ Kanamycin). Rooted plants are transferred to pots to promote further growth.

Example 3

Expression of NtMRP3 Polynucleotide in Tobacco Plants

To determine the expression of NtMRP3 polynucleotide, total cellular RNA is isolated from various parts of the plants. Total RNA is isolated using TRI® Reagent (Sigma-Aldrich, St. Louis, Mo.). To remove DNA impurities, purified RNA is treated with RNase-free DNase (TURBO DNA-free, Ambion, Austin Tex.). To synthesize the first cDNA strand, approximately 10 μg of total RNA is reverse transcribed utilizing the High Capacity cDNA Archive Kit (Applied Biosystems, Foster City, Calif.). To measure the level of NtMRP3 transcripts in the samples, a quantitative 2-step RT-PCR is performed according to the Taqman MGB probe-based chemistry. The RT mixture contains 4 μM dNTP mix, 1× random primers, 1× RT Buffer, 10 g cDNA, 50U Multiscribe Reverse transcriptase (Applied Biosystems), 2U Superase-In RNase Inhibitor (Ambion), and nuclease-free water. The PCR mixture contains 1× Taqman Universal PCR Master Mix (Applied Biosystems, Foster City, Calif.), 400 nM forward primer, 400 nM reverse primer, 250 nM Taqman MGB probe, 2 ng of cDNA, and nuclease-free water. RT-PCR is performed utilizing an ABI 7500 Real-Time System (Applied Biosystems, Foster City, Calif.) and under amplification conditions: 50° C. for 2 min.; 95° C. for 10 min.; 40 cycles of 95° C. for 15 sec.; and 60° C. for 1 min.

Example 4

Silencing of NtMRP3 Polynucleotide Expression in Tobacco Plants

A first partial sequence coding for a putative NtMRP3 transcript is found using Tobacco Genome Initiative (TGI) annotations. From this particular sequence, primers are generated to silence NtMRP3 polynucleotide expression in tobacco using a RNAi approach. The corresponding NtMRP3 RNAi sequence is amplified from cDNA by RT-PCR and then inserted into the Gateway vector pB7GWIWG2(II) via an entry vector, exactly as detailed by the manufacturer (Invitrogen). This vector contains a promoter for constitutive expression (the cauliflower mosaic virus CaMV 35S promoter) of the transgene in all tissues of the plant and the bar gene for herbicide selection with Basta on agar plates (30 mg/ml). The construct is then inserted in the genome of the Burley tobacco KY14 via *Agrobacterium tumefasciens* using a classical leaf disk procedure. From calli, individual lines are regenerated and selected on Basta. RNAi silencing lines are then monitored by RT-PCR and grown for seed production. T1 seeds are collected, re-grown on Basta-containing agar plates for selection and resistant plants are grown in floating trays before cultivation in the field.

Approximately 500 mg of the plant is weighed and digested in 10 ml of concentrated HNO$_3$ by the microwave-accelerated, reaction system 5 digestion system (CEM corporation, Mathews, N.C.). Heavy metal concentrations are analyzed utilizing inductively coupled plasma-mass spectrophotometry ("ICP-MS," Agilent 7500A; Agilent Technologies, Palo Alto, Calif.). As non-transgenic tobacco control, a sample consisting of polish-certified, Virginia tobacco leaves, CTA-VTL-2, is prepared under comparable conditions.

Example 5

Identification of the Genomic Sequence of NtMRP4 DNA

The genomic sequence of NtMRP4 DNA is identified by sequencing a BAC containing part of the genome which includes NtMRP4 DNA. The sequence is set forth in FIG. 1.

Example 6

Transformation of Tobacco Varieties with NtMRP4 RNAi Expression Vectors

Tobacco seeds are sterilized and germinated in a petri dish containing MS basal media supplemented with 5 ml/L plant preservative mixture (PPM). Seedlings, at approximately 7 to 10 days post-germination, are selected for transformation with various NtMRP4 RNAi expression vectors. A single colony of *Agrobacterium tumefaciens* LBA4404 is inoculated into a liquid LB medium containing 50 mg l$^{-1}$ kanamycin (kanamycin mono sulphate), and is incubated for 48 h at 28° C. with reciprocal shaking (150 cycles min$^{-1}$). Cultured cells are collected by centrifugation (6000×g, 10 min), and are suspended to a final density of 0.4-0.7 OD$_{600}$, with 20 ml liquid MS medium containing 20 g$^{-1}$ sucrose. The 7-10 day seedling explants are immersed into a bacterial suspension for 5 mins, and are blotted on sterile filter papers. Fifty explants are placed onto 40 ml aliquots of REG agar medium (MS basal medium supplemented with 0.1 mg l$^{-1}$ 1-naphthaleneacetic acid (NAA) and 1 mg l$^{-1}$ benzylaminopurine (BAP)) in 100 mm×20 mm petri dishes. The explants are co-cultivated with *Agrobacterium* at 25° C. After 3 days of co-cultivation, the explants are washed and transferred to RCPK medium (REG medium with 100 mg$^{-1}$ kanamycin, 500 mg l$^{-1}$ carbenicillin, and 5 ml PPM) to select for transformants.

The explants are subcultured every 2 weeks. After 8-12 weeks of growth under selective conditions, the surviving plants, representing transformants that have integrated the NtMRP4 RNAi expression constructs into their genomes, are transferred to a rooting medium (MS basal medium supplemented with 100 mg l$^{-1}$ Kanamycin). Rooted plants are transferred to pots to promote further growth.

Example 7

Expression of NtMRP4 Polynucleotide in Tobacco Plants

To determine the expression of NtMRP4 polynucleotide, total cellular RNA is isolated from various parts of the plants. Total RNA is isolated using TRI® Reagent (Sigma-Aldrich, St. Louis, Mo.). To remove DNA impurities, purified RNA is treated with RNase-free DNase (TURBO DNA-free, Ambion, Austin Tex.). To synthesize the first cDNA strand, approximately 10 µg of total RNA is reverse transcribed utilizing the High Capacity cDNA Archive Kit (Applied Biosystems, Foster City, Calif.). To measure the level of NtMRP4 transcripts in the samples, a quantitative 2-step RT-PCR is performed according to the Taqman MGB probe-based chemistry. The RT mixture contains 4 µM dNTP mix, 1× random primers, 1× RT Buffer, 10 g cDNA, 50U Multiscribe Reverse transcriptase (Applied Biosystems), 2U Superase-In RNase Inhibitor (Ambion), and nuclease-free water. The PCR mixture contains 1× Taqman Universal PCR Master Mix (Applied Biosystems, Foster City, Calif.), 400 nM forward primer, 400 nM reverse primer, 250 nM Taqman MGB probe, 2 ng of cDNA, and nuclease-free water. RT-PCR is performed utilizing an ABI 7500 Real-Time System (Applied Biosystems, Foster City, Calif.) and under amplification conditions: 50° C. for 2 min.; 95° C. for 10 min.; 40 cycles of 95° C. for 15 sec.; and 60° C. for 1 min.

NtMRP4 polynucleotide is expressed in tobacco tissues, as determined by RT-PCR using cDNA from petals, stamen, pistil, sepals, capsule, stems, leaves and roots.

Figure 2:
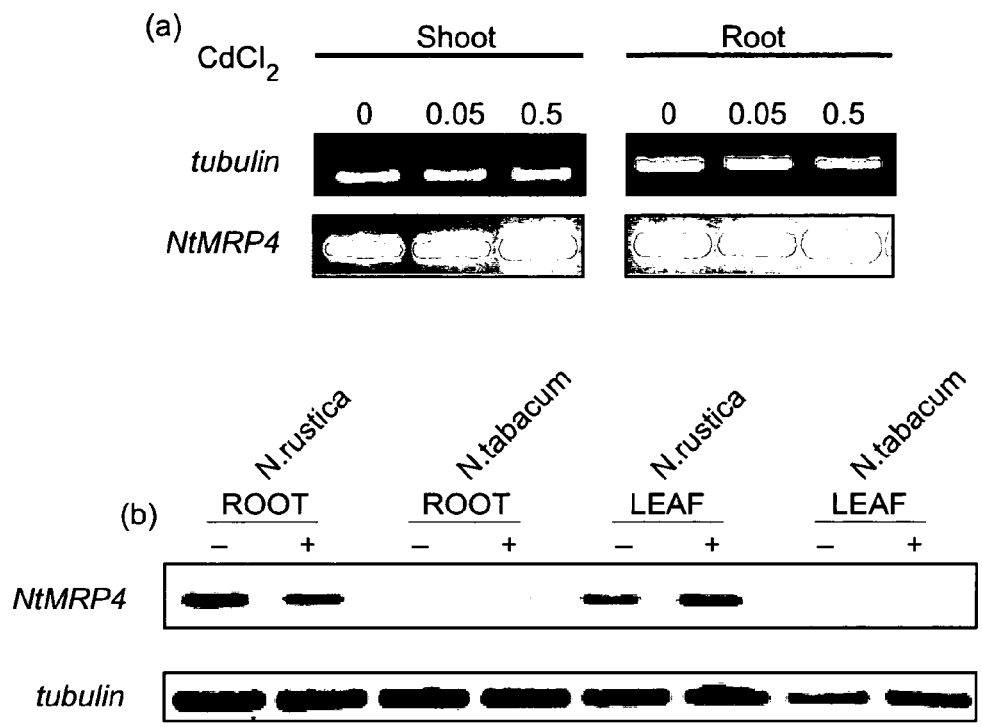
FIG. 2 illustrates the expression of NtMRP4 polynucleotide during cadmium treatment under hydroponic conditions for 7 days. Three week KY14 seedlings were treated with 0, 0.05 and 0.5 $CdCl_2$ (a) and 4 week *N. rustica* and *N. tabacum* (TN90) plantlets were treated with 0.5 micro.M $CdCl_2$ for one week (b). RNA was isolated and subjected to semi-quantitative RT-PCR.

When tobacco plants are cultivated in a hydroponic solution, expression of NtMRP4 polynucleotide is slightly up-regulated by cadmium in both root and leaf plantlets of *N. tabacum* (TN90, see FIG. 2). However, although NtMRP4 polynucleotide is found to also be induced in the leaf of *N. rustica*, opposite data is observed in the roots of *N. rustica* (down-regulation) compared to *N. tabacum*, thereby suggesting that NtMRP4 polynucleotide may play a role in cadmium accumulation in root and high cadmium tolerance of *N. rustica*.

Example 8

Silencing of NtMRP4 Polynucleotide Expression in Tobacco Plants

Figure 3:
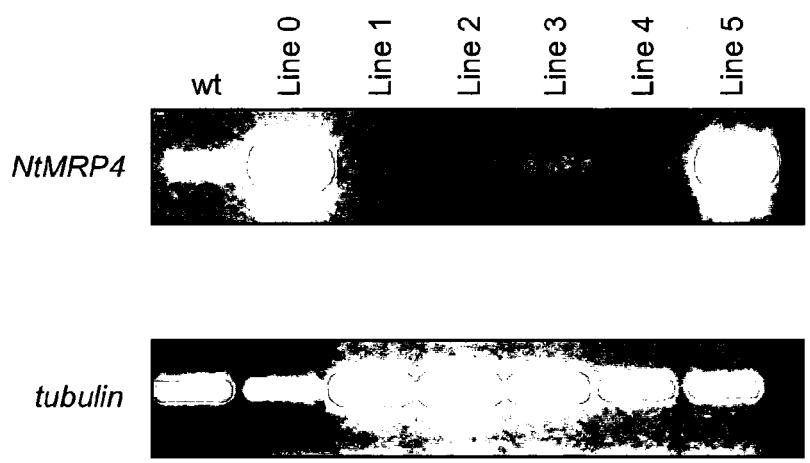
FIG. 3 illustrates NtMRP4 mRNA silencing is effective in lines 1 and 2 of NtMRP4 RNAi lines compared to wild-type field cultivated plants.

A first partial sequence (CHO_SL022xb24f1.ab1) coding for a putative NtMRP4 transcript (not shown) is found using Tobacco Genome Initiative (TGI) annotations. From this particular sequence, primers are generated to silence NtMRP4 polynucleotide expression in tobacco using a RNAi approach (FIG. 1). The corresponding MRP4 RNAi sequence is amplified from cDNA by RT-PCR and then inserted into the Gateway vector pB7GWIWG2(II) via an entry vector, exactly as detailed by the manufacturer (Invitrogen). This vector contains a promoter for constitutive expression (the cauliflower mosaic virus CaMV 35S promoter) of the transgene in all tissues of the plant and the bar gene for herbicide selection with Basta on agar plates (30 mg/ml). The construct is then inserted in the genome of the Burley tobacco KY14 via *Agrobacterium tumefasciens* using a classical leaf disk procedure. From calli, individual lines are regenerated and selected on Basta. RNAi silencing lines are then monitored by RT-PCR and grown for seed production. FIG. 3 shows that NtMRP4 silencing is effective in transgenic lines, including lines 1 and 2. T1 seeds are collected, re-grown on Basta-containing agar plates for selection and resistant plants are grown in floating trays before cultivation in the field.

Approximately 500 mg of the plant is weighed and digested in 10 ml of concentrated HNO$_3$ by the microwave-accelerated, reaction system 5 digestion system (CEM corporation, Mathews, N.C.). Heavy metal concentrations are analyzed utilizing inductively coupled plasma-mass spectrophotometry ("ICP-MS," Agilent 7500A; Agilent Technologies, Palo Alto, Calif.). As non-transgenic tobacco control, a sample consisting of polish-certified, Virginia tobacco leaves, CTA-VTL-2, is prepared under comparable conditions.

Figure 4:
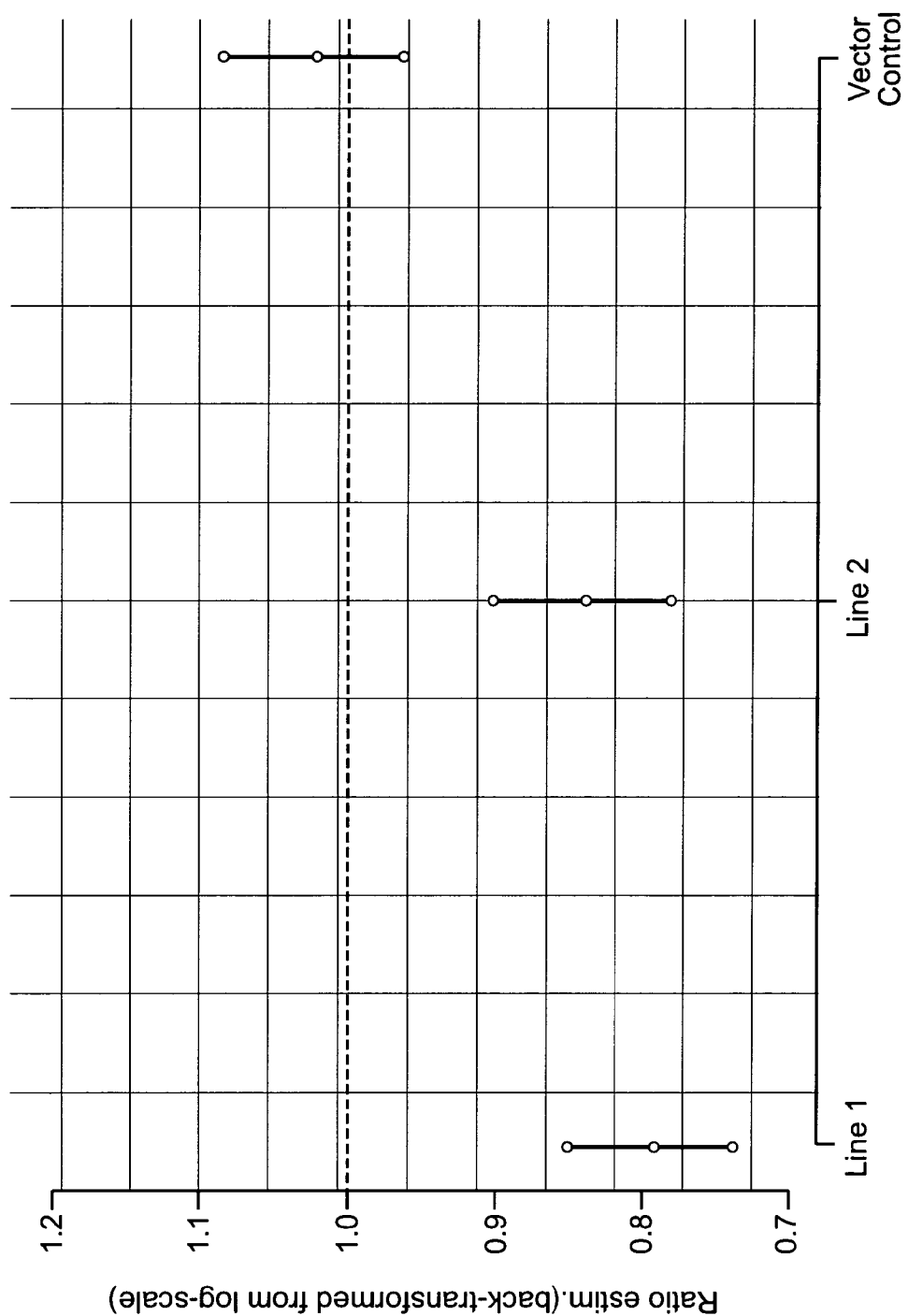
FIG. 4 shows cadmium reduction in leaf for two NtMRP4 RNAi cultivated lines. In this experiment a vector control without an NtMRP4 insert was added.
Figure 5:
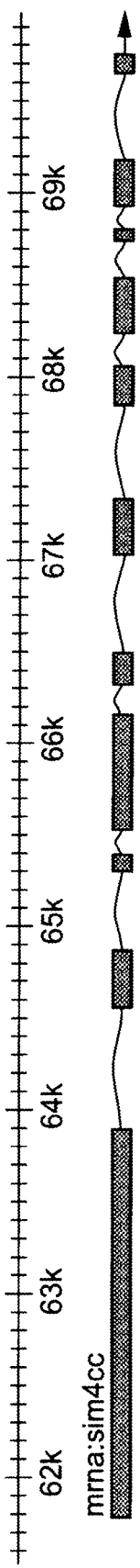
FIG. 5 shows the intron-exon structure and location of introns and exons along the genomic NtPMI-BAC-GOTOWE_5_gDNA BAC clone sequence spanning the NtMRP4 coding region. The homology of the cDNA sequence (basepair 1-4,521 upper strand) and genomic BAC clone sequence comprising the MRP4 coding region (basepair 61,781-69,748 lower strand) is 100%.

FIG. 4 shows a leaf cadmium reduction close to 20% in the two NtMRP4 RNAi lines tested (lines 1 and 2) following two successive field experiments in two consecutive years. In each case, the experimental units consist of four independent replicates of 4 collected plants (wt, lines 1 and 2 and vector control plants in second year Field experiment) which are randomized within blocks. In addition, control samples are added to the blocks in order to control for spatial trends. Analyses of NtMRP4 RNAi lines demonstrates a strong and statistically significant effect in reducing the mean level of cadmium.

Example 9

Height and Weight Analysis in Plants Derived from Tobacco Plants in which the Expression of NtMRP4 Polynucleotide is Silenced The height and weight of silenced NtMRP4 lines is slightly affected compared to the control plants. However no significant differences are found in dried collected leaves between NtMRP4 RNAi plants and wild type or vector control plants, thus indicating that the degradation of NtMRP4 transcripts has no effect statistically relevant on dry biomass. These data are confirmed by another field experiment showing that over-expressing AtMRP4 (homologous to NtMRP4 polynucleotide) in the same tobacco background (KY14) leads to 10-30% more cadmium accumulation in the leaves (depending on the transgenic lines). It is apparent that degrading the mRNA coding for NtMRP4 protein significantly reduces the level of cadmium in tobacco leaf.

Example 10

Identification of EMS-Induced Mutants in NtMRP4

A DNA library is made of *Nicotiana tabacum* plants which have been exposed to ethyl methanesulfonate (EMS) and are screened for mutants in exon 1 and exon 2 of NtMRP4 polynucleotide by sequencing the relevant part of the NtMRP4 gene of individual plants.

For exon 1

```
NtMRP4Exon1FW
(5'-CATCTCCTTACGAAGGATACTACC-3'; SEQ ID NO: 54)
and

NtMRP4Exon1REV
(5'-GCTGCAAGCTCTCCTTTTCTAA-3'; SEQ ID NO: 55)
``` are used for sequencing, and for exon 2,

```
NtMRP4Exon2FW
(5'-GTGCAATCTGGCAAATATAGTGAG-3'; SEQ ID NO: 56)
and

NtMRP4Exon2REV
(5'-AAAATGACATAGGAGCATGCAGTA-3'; SEQ ID NO: 57)
``` are used for sequencing.

An overview of all the mutants found for exon 1 and exon 2 of NtMRP4 polynucleotide is presented in the Table 1. The original codon (codon ori) and mutated codon (codon mut) as well as original amino acid (AS ori) and amino acid substitution (AS mut) or stopcodon are indicated.

Example 11

Search Protocol for the Selection of Zinc Finger Nuclease Target Sites

This example illustrates how to search the NtMRP4 gene to screen for the occurrence of unique target sites within the given gene sequence compared to a given genome database to develop tools for modifying the expression of the gene. The target sites identified by methods of the disclosure, including those disclosed below, the sequence motifs, and use of any of the sites or motifs in modifying the corresponding gene sequence in a plant, such as tobacco, are encompassed in the disclosure.

Search Algorithm.

A computer program is developed that allows one to screen an input query (target) nucleotide sequence for the occurrence of two fixed-length substring DNA motifs separated by a given spacer size using a suffix array within a DNA database, such as for example the tobacco genome sequence assembly of Example 1. The suffix array construction and the search use the open source libdivsufsort library-2.0.0 which converts any input string directly into a Burrows-Wheeler transformed string. The program scans the full input (target) nucleotide sequence and returns all the substring combinations occurring less than a selected number of times in the selected DNA database.

Selection of Target Site for Zinc Finger Nuclease-Mediated Mutagenesis of a Query Sequence.

A zinc finger DNA binding domain recognizes a three basepair nucleotide sequence. A zinc finger nuclease comprises a zinc finger protein comprising one, two, three, four, five, six or more zinc finger DNA binding domains, and the non-specific nuclease of a Type IIS restriction enzyme. Zinc finger nucleases can be used to introduce a double-stranded break into a target sequence. To introduce a double-stranded break, a pair of zinc finger nucleases, one of which binds to the plus (upper) strand of the target sequence and the other to the minus (lower) strand of the same target sequence separated by 0, 1, 2, 3, 4, 5, 6 or more nucleotides is required. By using plurals of 3 for each of the two fixed-length substring DNA motifs, the program can be used to identify two zinc finger protein target sites separated by a given spacer length.

Program Inputs:
1. The target query DNA sequence
2. The DNA database to be searched
3. The fixed size of the first substring DNA motif
4. The fixed size of the spacer
5. The fixed size of the second substring DNA motif
6. The threshold number of occurrences of the combination of program inputs 3 and 5 separated by program input 4 in the chosen DNA database of program input 2

Program Output:
1. A list of nucleotide sequences with for each sequence the number of times the sequence occurs in the DNA database with a maximum of the program input 6 threshold.

Example 12

Expression Profiling of NtMRP3 and NtMRP4 Transcripts in Tobacco

Development and analysis of tobacco ExonArray. Using the BAC clones obtained as described in Example 1, 272, 342 exons are identified by combining and comparing tobacco EST data and the methyl-filtered sequences obtained from the BAC sequencing. For each of these exons, four 25-mer oligonucleotides are designed and used to construct a tobacco ExonArray. The ExonArray is made by Affymetrix (Santa Clara, USA) using standard protocols.

Expression of NtMRP3 and NtMRP4 in tobacco. RNA is isolated from *Nicotiana* species grown on Cd+ (Cd contaminated) and Cd− (Cd deficient) soils, and analysed using standard hybridization protocols and analytical tools. Expression profiling is performed to identify gene sets related to Cd accumulation and to determine the influence of the soil Cd on the variation of the NtMRP3 and NtMRP4 transcripts. NtMRP3 and NtMRP4 probes used are located in the first and last exons as well as in the 3'UTR region. The results shown in Table 2 indicate that leaves of *N. tabacum* plants grown in a Cd contaminated soil accumulate more Cd than *N. rustica* plants grown in the same soil. Roots of *N. tabacum* plants accumulate less Cd than roots of *N. rustica* plants. Interestingly, both NtMRP3 and NtMRP4 are not regulated by Cd but their expression is different in the two *Nicotiana* species suggesting that both genes differently drive Cd uptake, translocation and accumulation in *Nicotiana* accessions (data are in log 2 corresponding to the mean of three biological replicates). As controls, the expression of three house-keeping genes (UBP12, exons 1 and 2), α-tubulin and the ribosomal protein S16 is shown.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the disclosure will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

| | Amplicon f seq | SEQ ID NO: | r seq | SEQ ID NO: | Codon ori | AS ori | Codon mut | AS mut |
|---|---|---|---|---|---|---|---|---|
| Exon 1 | NtMRP4-1 gaagctggaatg | 58 | attttaaagag | 59 | gau | asp | aau | asn |
| Exon 1 | NtMRP4-1 atgcttatt | | gatcgacact | 60 | cga | arg | uga | stop |
| Exon 1 | NtMRP4-1 aggttgtcatg | 61 | tcagctagac | 62 | ugc | cys | ugu | cys |
| Exon 1 | NtMRP4-1 tgctcagcta | 63 | acaggctcatg | 64 | aga | arg | aaa | lys |
| Exon 1 | NtMRP4-1 acaggctcatg | 64 | tgttggacag | 65 | ggu | gly | gau | asp |
| Exon 1 | NtMRP4-1 caggctcatg | 66 | tgttggacag | 65 | ggu | gly | gau | asp |
| Exon 1 | NtMRP4-1 tgttggaca | | attgtaaattat | 67 | cag | gln | caa | gln |
| Exon 1 | NtMRP4-1 ccgtagatgct | 68 | agcagctttc | 69 | cag | gln | uag | stop |
| Exon 1 | NtMRP4-1 gcagctgtcc | 70 | atatgctgca | 71 | gau | asp | aau | asn |
| Exon 1 | NtMRP4-1 gctacagcta | 72 | attccatttg | 73 | cau | his | uau | tyr |
| Exon 1 | NtMRP4-1 attccatttg | 73 | ctcatgccatt | 74 | ugg | trp | uga | stop |
| Exon 1 | NtMRP4-1 tgccattgcaa | 75 | tttctgtggc | 76 | guu | val | auu | Ile |
| Exon 1 | NtMRP4-1 ctttagccatc | 77 | tttatactta | 78 | cuu | leu | uuu | phe |
| Exon 1 | NtMRP4-1 ttcaactgtt | 79 | taacactagc | 80 | gua | val | aua | ile |
| Exon 1 | NtMRP4-1 tggacttgca | 81 | cagtgatggta | 82 | gca | ala | aca | thr |
| Exon 1 | NtMRP4-1 aggcaacaaat | 83 | agatgctta | | gag | glu | aag | lys |
| Exon 1 | NtMRP4-1 ttataaagtt | 84 | caggcatggg | 85 | uuc | phe | uuu | phe |
| Exon 1 | NtMRP4-1 ttataaagtt | 84 | caggcatggga | 86 | uuc | phe | uuu | cys |
| Exon 1 | NtMRP4-1 attgaatcttt | 87 | cgcgagtccga | 88 | uuc | phe | uuu | phe |
| Exon 1 | NtMRP4-1 aatctttccgc | 89 | agtccgagt | | gag | glu | aag | lys |
| Exon 1 | NtMRP4-1 agtacggatg | 90 | ttgtccaagtt | 91 | ugg | trp | uga | stop |
| Exon 1 | NtMRP4-1 agttcttgtact | 92 | aatagctggt | 93 | uca | ser | uua | leu |
| Exon 1 | NtMRP4-1 cattgtcttgt | 94 | gagcactcct | 95 | ugg | trp | uag | stop |
| Exon 1 | NtMRP4-1 ttgtcttgtg | 96 | agcactcctc | 97 | ugg | trp | uga | stop |
| Exon 1 | NtMRP4-1 tggagcactc | 98 | tcttctagt | | ccu | pro | cuu | leu |
| Exon 1 | NtMRP4-1 tcttctagttg | 99 | tacgctcactt | 100 | gcu | ala | guu | val |
| Exon 1 | NtMRP4-1 atcccgcttg | 101 | cgcaggaaca | 102 | gcg | ala | acg | thr |
| Exon 1 | NtMRP4-1 atcccgcttg | 101 | cgcaggaaca | 102 | gug | val | aug | met |
| Exon 1 | NtMRP4-1 gaaccgatca | 103 | ggctttccct | 104 | agg | arg | aag | lys |
| Exon 1 | NtMRP4-1 aaccgatcag | 105 | gctttccctc | 106 | agg | arg | aga | arg |
| Exon 1 | NtMRP4-1 catgatctca | 107 | tttcacaagca | 108 | cuu | leu | uuu | cys |
| Exon 1 | NtMRP4-1 atctcttgata | 109 | attggacaaat | 110 | aga | arg | aaa | lys |
| Exon 2 | NtMRP4-2 tattagaagct | 111 | gaatggatttt | 112 | gga | gly | aga | arg |
| Exon 2 | NtMRP4-2 ttcaccgcga | 113 | atctctcttc | 114 | aca | thr | aua | ile |
| Exon 2 | NtMRP4-2 aaacaaccaaa | 115 | agagcaatgc | 116 | gag | gly | aag | lys |
| Exon 2 | NtMRP4-2 ccttgaagaat | 117 | aaaatcttctc | 118 | uca | ser | uua | leu |
| Exon 2 | NtMRP4-2 agaatcaaaat | 119 | ttctcgaagat | 120 | ucu | ser | uuu | phe |
| Exon 2 | NtMRP4-2 tatctaaggaa | 121 | aaaacggaga | 122 | gaa | glu | aaa | lys |
| Exon 2 | NtMRP4-2 tcaacagtcta | 123 | atctga | | aca | thr | aua | ile |
| Exon 2 | NtMRP4-2 atctgataag | 124 | gggattctaaa | 125 | ggg | gly | agg | arg |
| Exon 2 | NtMRP4-2 acttataaag | 126 | aagaagaaag | 127 | gaa | glu | aaa | lys |
| Exon 2 | NtMRP4-2 aacttataaag | 128 | aagaagaaag | 127 | gaa | glu | aaa | lys |
| Exon 2 | NtMRP4-2 aaggaagaa | | aaagagaaactg | 129 | gaa | glu | aaa | lys |
| Exon 2 | NtMRP4-2 gctatatatta | 130 | tgaagcttttg | 131 | acu | thr | auu | ile |
| Exon 2 | NtMRP4-2 gctatatatta | 130 | tgaagcttttg | 131 | acu | thr | auu | ile |
| Exon 2 | NtMRP4-2 gaagcttttg | 132 | atggtgggg | | gga | gly | gaa | glu |
| Exon 2 | NtMRP4-2 ttggatggtg | 133 | ggcgtagtgct | 134 | ugg | trp | uga | stop |
| Exon 2 | NtMRP4-2 ttgtggcaaa | 135 | ttctctaatg | 136 | agu | ser | aau | asn |
| Exon 2 | NtMRP4-2 gttctctaat | 137 | gcaagtga | | aug | leu | aua | leu |
| Exon 2 | NtMRP4-2 gcaaagttct | 138 | taatggcaag | 139 | cua | leu | uua | leu |
| Exon 2 | NtMRP4-2 tattggcctg | | catatgaaac | 140 | gca | ala | aca | thr |
| Exon 2 | NtMRP4-2 caacaaatga | 141 | atgcttaatt | 142 | gag | glu | gaa | glu |
| Exon 2 | NtMRP4-2 cttcagcrgay | 143 | gtgccatgtcct | 144 | cgu | arg | ugu | cys |
| Exon 2 | NtMRP4-2 tgtccttcaat | 145 | cttctctgtt | 146 | ccu | pro | ucu | ser |
| Exon 2 | NtMRP4-2 ggcatgggaa | 147 | aacatttaa | 148 | gaa | glu | aaa | lys |

TABLE 2

|  | Root *N. rustica* | | Root TN90 | | Leaf *N. rustica* | | Leaf TN90 | |
|---|---|---|---|---|---|---|---|---|
|  | Low Cd | High Cd | Low Cd | High Cd | Low Cd | High Cd | Low Cd | High Cd |
| NtMRP3_exon1 | 5.9 | 4.9 | 7.5 | 7.7 | 5.6 | 5.8 | 7.5 | 7.9 |
| NtMRP3_exon2 | 1.6 | 1.7 | 7.0 | 7.1 | 2.2 | 2.0 | 5.5 | 6.5 |
| NtMRP3_exon2 | 6.1 | 5.6 | 9.6 | 9.6 | 4.1 | 4.5 | 9.0 | 9.6 |
| NtMRP3 exons 8&10 | 5.3 | 5.4 | 7.5 | 7.4 | 5.3 | 5.1 | 6.5 | 7.1 |
| NtMRP4 exon 1 | 6.4 | 6.4 | 5.1 | 4.5 | 7.6 | 8.2 | 7.6 | 7.3 |
| NtMRP4 3'UTR | 6.2 | 6.4 | 3.9 | 3.8 | 7.9 | 7.9 | 5.9 | 6.5 |
| NtMRP4 exon 1 | 7.5 | 7.7 | 5.9 | 5.4 | 9.3 | 9.1 | 9.1 | 9.4 |
| NtMRP4 exon 11 (last exon) | 6.2 | 6.1 | 5.0 | 4.8 | 7.6 | 7.6 | 7.2 | 7.2 |
| Ubiquitin-specific protease 12 (UBP12) exon 1 | 6.7 | 6.6 | 6.3 | 5.7 | 6.2 | 5.4 | 5.8 | 6.1 |
| Ubiquitin-specific protease 12 (UBP12) exon 2 | 6.5 | 6.9 | 6.0 | 6.0 | 6.3 | 6.6 | 5.9 | 5.7 |
| Beta-tubulin | 5.8 | 5.6 | 5.7 | 6.0 | 5.4 | 5.5 | 5.6 | 5.6 |
| Ribosomal protein S16 | 9.9 | 10.1 | 9.9 | 10.5 | 11.7 | 11.7 | 11.3 | 11.3 |

The invention claimed is:

1. A mutant, non-naturally occurring or transgenic tobacco plant, comprising an exogenous polynucleotide of at least 19 contiguous nucleotides in length having at least 90% sequence identity to a polynucleotide encoding a region of SEQ ID NO: 24, wherein the exogenous polynucleotide is configured to decrease expression of NtMRP polynucleotide or the activity of the protein encoded thereby by at least 50% and wherein the leaves of said plant have a reduction in cadmium content of at least 5% as compared to a control plant in which the expression of NtMRP or the activity of the protein encoded thereby has not decreased.

2. A method for reducing cadmium levels in at least a part of a tobacco plant, comprising the step of genetically manipulating the tobacco plant to comprise an exogenous polynucleotide of at least 19 contiguous nucleotides in length having at least 90% sequence identity to a polynucleotide encoding a region of SEQ ID NO: 24, wherein the exogenous polynucleotide is configured to decrease expression of a NtMRP polynucleotide or the activity of the protein encoded thereby by at least 50% as compared to a control plant in which the expression of the NtMRP polynucleotide or the activity of the protein encoded thereby has not decreased.

3. A mutant, non-naturally occurring or transgenic plant obtained by the method according to claim 2, wherein there is a reduction in cadmium content of at least about 5% in at least a part of the plant as compared to a control plant in which the expression of NtMRP polynucleotide or the activity of the protein encoded thereby has not decreased.

4. Plant material including biomass, seed or leaves comprising genetically transformed cells or tissue from the plant of claim 1, further comprising the exogenous polypeptide.

5. A tobacco product comprising plant material according to claim 4.

6. A tobacco product comprising a genetically transformed part of the plant of claim 1, further comprising the exogenous polypeptide.

7. The mutant, non-naturally occurring or transgenic tobacco plant of claim 1, comprising an expression vector comprising a promoter operably-linked to the exogenous polynucleotide, wherein induction of the expression vector causes expression of a NtMRP RNA interference (RNAi) polynucleotide and the reduction in cadmium concentration in the leaves of said plant as compared to the control plant.

8. The method of claim 2, comprising the step of inducing the expression of a NtMRP RNAi polynucleotide from an expression vector comprising a promoter operably-linked to the exogenous polynucleotide.

* * * * *